US007563770B2

(12) United States Patent
Larsen et al.

(10) Patent No.: US 7,563,770 B2
(45) Date of Patent: Jul. 21, 2009

(54) GLUCAGON-LIKE-PEPTIDE-2 (GLP-2) ANALOGUES

(75) Inventors: Bjarne Due Larsen, Roskilde (DK); Yvette Miata Petersen, Bagsvaerd (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 11/429,168

(22) Filed: May 4, 2006

(65) Prior Publication Data
US 2007/0231308 A1    Oct. 4, 2007

Related U.S. Application Data

(60) Provisional application No. 60/678,066, filed on May 4, 2005.

(51) Int. Cl.
*A61K 38/00* (2006.01)
*A01N 43/04* (2006.01)
*C07K 16/00* (2006.01)

(52) U.S. Cl. ............................. 514/12; 514/44; 530/308
(58) Field of Classification Search ........................ None
See application file for complete search history.

(56) References Cited

U.S. PATENT DOCUMENTS

| | | | |
|---|---|---|---|
| 5,789,379 | A | 8/1998 | Drucker et al. |
| 5,834,428 | A | 11/1998 | Drucker |
| 5,912,229 | A | 6/1999 | Thim et al. |
| 5,990,077 | A | 11/1999 | Drucker |
| 5,994,500 | A | 11/1999 | Drucker et al. |
| 6,051,557 | A | 4/2000 | Drucker |
| 6,184,201 | B1 | 2/2001 | Drucker et al. |
| 6,184,208 | B1 | 2/2001 | Deigin et al. |
| 6,297,214 | B1 | 10/2001 | Drucker |
| 6,586,399 | B1 | 7/2003 | Drucker |
| 6,770,620 | B2 | 8/2004 | Henriksen |
| 2002/0025933 | A1 | 2/2002 | Knudsen et al. |
| 2003/0040478 | A1 | 2/2003 | Drucker et al. |
| 2003/0109449 | A1 | 6/2003 | Drucker et al. |
| 2003/0158101 | A1 | 8/2003 | Drucker |
| 2003/0162703 | A1 | 8/2003 | Drucker et al. |
| 2003/0207809 | A1 | 11/2003 | Drucker |
| 2004/0052862 | A1 | 3/2004 | Henriksen et al. |
| 2004/0122210 | A1 | 6/2004 | Thim et al. |
| 2004/0127418 | A1 | 7/2004 | Knudsen et al. |
| 2005/0282749 | A1 | 12/2005 | Henriksen et al. |
| 2006/0105954 | A1 | 5/2006 | Drucker |

FOREIGN PATENT DOCUMENTS

| | | |
|---|---|---|
| WO | WO 96/32414 | 10/1996 |
| WO | WO 97/39031 | 10/1997 |
| WO | WO 99/46283 | 9/1999 |
| WO | WO 01/41779 | 6/2001 |
| WO | WO 02/066511 | 8/2002 |

OTHER PUBLICATIONS

Drucker et al., "Regulation of the Biological Activity of Glucagon-like Peptide 2 In Vivo by Dipeptidyl Peptidase IV" *Nature Biotechnology* 15:673-677 (1997).
International Search Report from PCT/GB2006/001633 dated Oct. 24, 2006.
U.S. Appl. No. 11/595,496, filed Nov. 9, 2006.
Benjamin et al., "Glucagon-like peptide-2 enhances intestinal epithelial barrier function of both transcellular and paracellular pathways in the mouse," *Gut* 47:112-119 (2000).
Booth et al., "Teduglutide ([Gly2]GLP-2) protects small intestinal stem cells from radiation damage," *Cell Prolif.* 37:385-400 (2004).
Boushey et al., "Glucagon-like peptide (GLP)-2 reduces chemotherapy-associated mortality and enhances cell survival in cells expressing a transfected GLP-2 receptor," *Cancer Res.* 61:687-693 (2001).
Cheeseman, "Upregulation of SGLT-1 transport activity in rat jejunum induced by GLP-2 infusion in vivo," *Am. J. Physiol* 273:R1965-R1971 (1997).
DaCambra et al., "Structural determinants for activity of glucagon-like peptide-2," *Biochemistry* 39:8888-8894 (2000).
Drucker et al., "Induction of intestinal epithelial proliferation by glucagon-like peptide 2," *Proc. Natl. Acad. Sci. USA* 93:7911-7916 (1996).

(Continued)

*Primary Examiner*—Robert Landsman
*Assistant Examiner*—Ian Dang
(74) *Attorney, Agent, or Firm*—Clark & Elbing LLP; Kristina Bieker-Brady

(57) ABSTRACT

GLP-2 analogues are disclosed which comprise one of more substitutions as compared to [hGly2]GLP-2 and which improved biological activity in vivo and/or improved chemical stability, e.g. as assessed in in vitro stability assays. More particularly, preferred GLP-2 analogues disclosed herein comprise substitutions at one or more of positions 8, 16, 24 and/or 28 of the wild-type GLP-2 sequence, optionally in combination with further substitutions at position 2 (as mentioned in the introduction) and one or more of positions 3, 5, 7, 10 and 11, and/or a deletion of one or more of amino acids 31 to 33 and/or the addition of a N-terminal or C-terminal stabilizing peptide sequence. The analogues are particularly useful for the prophylaxis or treatment of stomach and bowel-related disorders and for ameliorating side effects of chemotherapy.

2 Claims, 14 Drawing Sheets

OTHER PUBLICATIONS

Ferrone et al., "Teduglutide for the treatment of short bowel syndrome," *Ann. Pharmacother.* 40:1105-1109 (2006).

Guan et al., "GLP-2-mediated up-regulation of intestinal blood flow and glucose uptake is nitric oxide-dependent in TPN-fed piglets," *Gastroenterology* 125:136-147 (2003).

Jeppesen et al., "The use of hormonal growth factors in the treatment of patients with short-bowel syndrome," *Drugs* 66:581-589 (2006).

Sinclair et al., "Proglucagon-derived peptides: mechanisms of action and therapeutic potential," *Physiology* 20:357-365 (2005).

Tavares et al., "Enzymatic- and renal-dependent catabolism of the intestinotropic hormone glucagon-like peptide-2 in rats", *Am. J. Physiol. Ednocrinol. Metab.* 278:E134-E139 (2000).

Thulesen et al., "Glucagon-like peptide 2 (GLP-2) accelerates the growth of colonic neoplasms in mice," *Gut* 53:1145-1150 (2004).

Wojdemann et al., "Inhibition of sham feeding-stimulated human gastric acid secretion by glucagon-like peptide-2," *J. Clin. Endocrinol. Metab.* 84:2513-2517 (1999).

Yusta et al., "Enteroendocrine localization of GLP-2 receptor expression in humans and rodents," *Gastroenterology* 119:744-755 (2000).

A)

B)

A)

B)

A)

B)

A)

B)

A)

B)

A)

B)

A)

B)

GLUCAGON-LIKE-PEPTIDE-2 (GLP-2) ANALOGUES

CROSS-REFERENCE TO RELATED APPLICATIONS

This application claims benefit from U.S. Provisional Application No. 60/678,066, filed May 4, 2005, which is hereby incorporated by reference.

FIELD OF THE INVENTION

The present invention relates to glucagon-like-peptide-2 (GLP-2) analogues and their medical use, for example in the prophylaxis or treatment of stomach and bowel-related disorders and for ameliorating side effects of chemotherapy and radiation therapy.

BACKGROUND OF THE INVENTION

GLP-2 is a 33-amino-acid peptide released from the posttranslational processing of proglucagon in the enteroendocrine L cells of the intestine and in specific regions of the brainstem. It is co-secreted together with glucagon-like peptide 1 (GLP-1), oxyntomodulin and glicentin, in response to nutrient ingestion.

GLP-2 induces significant growth of the small intestinal mucosal epithelium via the stimulation of stem cell proliferation in the crypts and inhibition of apoptosis on the villi (Drucker et al. Proc Natl Acad Sci USA. 1996, 93:7911-6). GLP-2 also inhibits gastric emptying and gastric acid secretion (Wojdemann et al. J Clin Endocrinol Metab. 1999, 84:2513-7), enhances intestinal barrier function (Benjamin et al. Gut. 2000, 47:112-9.), stimulates intestinal hexose transport via the upregulation of glucose transporters (Cheeseman, Am J. Physiol. 1997, R1965-71), and increases intestinal blood flow (Guan et al. Gastroenterology. 2003, 125, 136-47).

GLP-2 binds to a single G protein-coupled receptor belonging to the class II glucagon secretin family (1). The GLP-2 receptor has only been localized in the small intestine, colon and stomach, sites that are known to be responsive to GLP-2 (Yusta et al. Gastroenterology. 2000, 119: 744-55). However, the target cell for GLP-2 receptor stimulation in the gastrointestinal tract remanins unclear and the downstream intracellular mediators coupled to the GLP-2 receptor are poorly understood.

The demonstrated specific and beneficial effects of GLP-2 in the small intestine has raised much interest as to the use of GLP-2 in the treatment of intestinal disease or injury (Sinclair and Drucker, Physiology 2005: 357-65). Furthermore GLP-2 has been shown to prevent or reduce mucosal epithelial damage in a wide number of preclinical models of gut injury, including chemotherapy-induced mucositis, ischemia-reperfusion injury, dextran sulfate-induced colitis and genetic models of inflammatory bowel disease (Sinclair and Drucker, Physiology 2005:357-65).

GLP-2 is secreted as a 33 amino acid peptide with the following sequence H-His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp-OH (SEQ ID NO:50). It is rapidly cleaved at the Alanine (A) in position 2 of the $NH_2$ terminus to the inactive human GLP-2 (3-33) by the enzyme DPP IV. This rapid enzymatic degradation of GLP-2(1-33), in addition to renal clearance result in a half life of about 7 minutes for the peptide (Tavares et al., Am. J. Physiol. Endocrinol. Metab. 278:E134-E139, 2000).

In U.S. Pat. No. 5,994,500 (Drucker et al.) describes antagonists of the GLP-2 and their effects on the growth of gastrointestinal tissue. It is suggested that the antagonists are formulated as pharmaceuticals to be used in the treatment of hyperplasia or to induce hypoplasia. In U.S. Pat. No. 5,994,500 the structure of mammalian GLP-2 has been altered by mutations, such as substitutions and deletions.

U.S. Pat. Nos. 6,184,208, 5,789,379, and 6,184,201 disclose GLP-2 analogues and their medical uses. The analogues are all obtained by substitutions and/or deletions of the human GLP-2.

DaCambra et al. (Biochemistry 2000, 39, 8888-8894) describe the structural determinants for activity of GLP-2. Examples of such determinants are Phe6 and Thr5, which are referred to as crucial for GLP-2 receptor binding and activation.

In WO 97/39031 the GLP-2 analogue, [Gly2]GLP-2 (SEQ ID NO:54) is disclosed. Here the alanine in position 2 has been replaced with glycine to make the peptide resistant to DPP IV cleavage. The replacement of alanine is shown to increase the stability and potency of the peptide. The patent application describes how the GLP-2 analogue may be used against diseases associated with inflammation and destruction of the intestinal epithelial mucosa. These include massive small intestine resection, inflammatory bowel disease, chemotherapy induced mucositis and ischemic injury.

WO 02/066511 describes GLP-2 analogues having an extended half life in vivo and their use as medicaments in the treatment of gastrointestinal disorders, such as inflammatory bowel diseases.

WO 01/41779 describes the use of h[Gly2]GLP-2 (SEQ ID NO:54) as a pretreatment for inhibiting chemotherapy induced apoptosis and promoting cell survival.

All references cited herein are expressly incorporated by reference in their entirety.

The use of GLP-2 or analogues of GLP-2 in the treatment of various diseases has been proposed by many scientists. However, there is still a need for improved and stable GLP-2 analogues.

SUMMARY OF THE INVENTION

Broadly, the present invention concerns GLP-2 analogues which comprise one of more substitutions as compared to wild-type GLP-2 and which may have the property of an improved biological activity in vivo and/or improved chemical stability, e.g. as assessed in in vitro stability assays. More particularly, preferred GLP-2 analogues of the present invention comprise substitutions at one or more of positions 8, 16, 24 and/or 28 of the wild-type GLP-2 sequence, optionally in combination with further substitutions at position 2 (as mentioned in the introduction) and one or more of positions 3, 5, 7, 10 and 11, and/or a deletion of one or more of amino acids corresponding to positions 31 to 33 of the wild-type GLP-2 sequence and/or the addition of a N-terminal or C-terminal stabilizing peptide sequence. As well as providing GLP-2 analogues that may have improved chemical stability and/or biological activity, the present invention also relates to providing compounds that have preferential intestinal growth promoting activity in the small intestine compared to the colon and vice versa, in particular by including modification at one or more of positions Asp3 and/or Ser 8 and/or Asn16 and/or Asn24 and/or Gln28 of wild-type GLP-2.

Accordingly, in one aspect, the present invention provides a GLP-2 analogue which is represented by general Formula I (SEQ ID NO:51):

R$^1$-Z$^1$-His-X2-X3-Gly-X5-X6-X7-X8-X9-X10-X11-X12-X13-X14-X15-X16-X17-Ala-X19-X20-X21-Phe-Ile-X24-Trp-Leu-Ile-X28-Thr-Lys-X31-X32-X33-Z$^2$-R$^2$ wherein:
R$^1$ is hydrogen, C$_{1-4}$ alkyl (e.g. methyl), acetyl, formyl, benzoyl or trifluoroacetyl
X2 is Gly, Ala or Sar
X3 is Glu or Asp
X5 is Ser or Thr
X6 is Phe or Pro
X7 is Ser or Thr
X8 is Asp or Ser
X9 is Glu or Asp
X10 is Met, Leu, Nle or an oxidatively stable Met-replacement amino acid
X11 is Asn, Ala, Lys or Ser
X12 is Thr or Lys
X13 is Ile, Glu or Gln
X14 is Leu, Met or Nle
X15 is Asp or Glu
X16 is Asn or Ala
X17 is Leu or Glu
X18 is Ala or Aib
X19 is Ala or Thr
X20 is Arg or Lys
X21 is Asp or Ile
X24 is Asn, Ala or Glu
X28 is Gln, Ala or Asn
X31 is Pro, Ile or deleted
X32 is Thr or deleted
X33 is Asp, Asn or deleted
R$^2$ is NH$_2$ or OH;
Z$^1$ and Z$^2$ are independently absent or a peptide sequence of 3-20 amino acid units selected from the group consisting of Ala, Leu, Ser, Thr, Tyr, Asn, Gln, Asp, Glu, Lys, Arg, His, Met and Orn; wherein the GLP-2 analogue comprises one or more of substitutions selected from X8 is Ser and/or X16 is Ala and/or X24 is Ala and/or X28 is Ala;

or a pharmaceutically acceptable salt or derivative thereof.

In a further embodiment, the present invention provides a GLP-2 analogue represented by general Formula II (SEQ ID NO:52):

R$^1$-Z$^1$-His-Gly-X3-Gly-X5-Phe-X7-X8-X9-X10-X11-X12-X13-X14-X15-X16-X17-Ala-X19-Arg-Asp-Phe-Ile-X24-Trp-Leu-Ile-X28-Thr-Lys-X31-X32-X33-Z$^2$-R$^2$ wherein:
R$^1$ is hydrogen, C$_{1-4}$ alkyl (e.g. methyl), acetyl, formyl, benzoyl or trifluoroacetyl
X3 is Glu or Asp
X5 is Ser or Thr
X7 is Ser or Thr
X8 is Asp or Ser
X9 is Glu or Asp
X10 is Met, Leu, Nle or an oxidatively stable Met-replacement amino acid
X11 is Asn, Ala, Lys or Ser
X12 is Thr or Lys
X13 is Ile, Glu or Gln
X14 is Leu, Met or Nle
X15 is Asp or Glu
X16 is Asn or Ala
X17 is Leu or Glu
X19 is Ala or Thr
X24 is Asn or Ala
X28 is Gln, Ala or Asn
X31 is Pro, Ile or deleted
X32 is Thr or deleted
X33 is Asp or deleted
R$^2$ is NH$_2$ or OH;
Z$^1$ and Z$^2$ are independently absent or a peptide sequence of 3-20 amino acid units selected from the group consisting of Ala, Leu, Ser, Thr, Tyr, Asn, Gln, Asp, Glu, Lys, Arg, His, Met and Orn; wherein the GLP-2 analogue comprises one or more of substitutions selected from X8 is Ser and/or X16 is Ala and/or X24 is Ala and/or X28 is Ala;

or a pharmaceutically acceptable salt or derivative thereof.

In a further embodiment, the present invention provides a GLP-2 analogue represented by general Formula III (SEQ ID NO:53):

R$^1$-Z$^1$-His-Gly-X3-Gly-X5-Phe-X7-X8-Glu-X10-X11-Thr-Ile-Leu-Asp-X16-Leu-Ala-Ala-Arg-Asp-Phe-Ile-X24-Trp-Leu-Ile-X28-Thr-Lys-X31-X32-X33-Z$^2$-R$^2$ wherein:
R$^1$ is hydrogen, C$_{1-4}$ alkyl (e.g. methyl), acetyl, formyl, benzoyl or trifluoroacetyl
X3 is Glu or Asp
X5 is Ser or Thr
X7 is Ser or Thr
X8 is Asp or Ser
X10 is Met, Leu, Nle, or an oxidatively stable Met-replacement amino acid
X11 is Asn, Ala, Lys or Ser
X24 is Asn or Ala
X28 is Gln or Ala
X31 is Pro or deleted
X32 is Thr or deleted
X33 is Asp or deleted
R$^2$ is NH$_2$ or OH;
Z$^1$ and Z$^2$ are independently absent or a peptide sequence of 3-20 amino acid units selected from the group consisting of Ala, Leu, Ser, Thr, Tyr, Asn, Gln, Asp, Glu, Lys, Arg, His, Met and Orn wherein the GLP-2 analogue comprises one or more of substitutions selected from X8 is Ser and/or X16 is Ala and/or X24 is Ala and/or X28 is Ala;

or a pharmaceutically acceptable salt or derivative thereof.
Where X16 is not Ala, it will be Asn.

In certain embodiments, when Z$^1$ is present R$^1$ may be H, and when Z$^2$ is present R$^2$ may be OH.

In some embodiments of the present invention, the GLP-2 analogue at least 60% amino acid sequence identity to wild-type GLP-2 (1-33) having the sequence set out in the introduction of the application (SEQ ID NO:50), more preferably at least 63% sequence identity, more preferably at least 66% sequence identity and still more preferably at least 69% sequence identity.

"Percent (%) amino acid sequence identity" with respect to the GLP-2 polypeptide sequences is defined as the percentage of amino acid residues in a candidate sequence that are identical with the amino acid residues in the wild-type GLP-2 sequence, after aligning the sequences and introducing gaps, if necessary, to achieve the maximum percent sequence identity, and not considering any conservative substitutions as part of the sequence identity. Sequence alignment can be carried out by the skilled person using techniques well known in the art for example using publicly available software such as BLAST, BLAST2 or Align software, see: Altschul et al (Methods in Enzymology, 266:460-480 (1996)) or Pearson et al (Genomics, 46, 24,36, 1997) for the Align program. The percentage sequence identities used herein and in accordance with the present invention are determined using these programe with their default settings. More generally, the skilled person can readily determine appropriate parameters for determining alignment, including any algorithms needed to achieve maximal alignment over the full length of the sequences being compared.

In some preferred embodiments, the GLP-2 peptide analogues represented by Formula I, II or III comprise substitutions at more than one of positions X8, X16, X24 and/or X28 and/or a combination of these substitutions with other substitutions, preferably those at positions X3, X5, X7, X10 and/or X11.

Examples of combinations of X8, X16, X24 and/or X28 substitutions that fall within Formulae I to III include:
Ser8, Ala16
Ser8, Ala24
Ser8, Ala28
Ala16, Ala24
Ala16, Ala28
Ala24, Ala28
Ser8, Ala16, Ala24
Ser8, Ala16, Ala28
Ser8, Ala24, Ala28
Ala16, Ala24, Ala28
Ser8, Ala16, Ala24, Ala28

Examples of substitutions at positions X3, X5, X7, X10 and/or X11 that fall within Formulae I to III and may be combined with a substitution at one or more of positions X8, X16, X24 and/or X28 include:
Glu3, Leu10, Ala11,24
Glu3, Thr5, Leu10, Ser11, Ala16,24,28
Glu3, Thr5, Leu10, Lys11, Ala16,24,28
Glu3, Thr5, Ser8, Leu 10, Lys11, Ala16,24,28
Glu3, Thr5, Ser8,11, Leu10, Ala16,24,28
Glu3, Thr5, Ser8,11, Leu10, Ala16,24,28
Glu3, Ser8,11, Leu10, Ala16,24,28
Glu3, Leu10, Ser 1, Ala16,24,28
Glu3, Leu10, Lys11, Ala16,24,28
Glu3, Thr5, Leu10, Ala11,16,24,28
Glu3, Thr5, Leu10, Ala11,16,24,28, Ile21
Glu3, Thr5, Ser8, Leu 10, Ala 11,16,24,28
Glu3, Ser8, Leu10, Ala11,16,24,28
Glu3, Leu10, Ala11,16,24,28
Thr7, Leu10, Ala11, 24
Thr7, Leu10, Lys11, Ala24
Thr7, Leu10, Ser11, Ala24
Thr7, Leu10, Ser8,11, Ala24
Thr7, Ser8, Leu10, Ala11,24
Thr7, Ser8, Leu10, Lys11, Ala24
Ser8, Leu10, Ala11,24
Leu10, Ala24
Leu10, Ala11, Ala24
Leu10, Ala11,24,28
Leu10, Ala11,16,24,28
Leu10, Lys11, Ala24
Leu10, Ser11, Ala24
Leu10, Ser8,11, Ala24 or a deletion at one or more of positions X31-X33 in combination with an above mentioned change at position 8, 16, 24 and/or 28.

Specific examples of the GLP-2 compounds of the present invention are set out in the detailed description below.

As well as providing GLP-2 analogues that may have improved chemical stability and biological activity, the present invention also relates to providing compounds that have preferential growth promoting activity in the small intestine compared to the colon and vice versa. In particular, the experiments described herein show that substitution at positions Asp3 and/or Ser 8 and/or Asn16 and/or Gln28 of wild-type GLP-2 provide a preferential increase of the small intestine weight when administered to test animals compared to the increase in colon mass. These findings mean that the exemplified compounds may be useful for treating conditions where it is advantageous to have an increased growth promoting effect in the small intestine, while having a lesser effect on the colon, and vice versa.

Thus, compounds that are preferred for causing growth of the small intestine typically comprise one or more substitutions at positions 3, 8, 16 and/or 28 of wild-type GLP-2. Such compounds may selectively cause growth of the small intestine rather than the colon. They may therefore be used for conditions affecting or related to the small intestine.

Preferably, such small intestine-selective compounds comprise substitutions at more than one of positions X3, X7, X16, X24, X28, X31, X32 and/or X33. Thus, the small-intestine-selective compounds may comprise more than one of the substitutions X3 is Glu, X7 is Ser, X16 is Ala, X24 is Ala, X28 is Ala, X31 is Ile, X32 is Thr and X33 is Asp. The amino acid residues in positions X31, X32 and X33 may optionally be deleted.

Exemplified compounds preferentially stimulating epithelial growth in the small intestine include 1809 (SEQ ID NO:1), 1818 (SEQ ID NO:8), 1819 (SEQ ID NO:9), 1820 (SEQ ID NO:10), 1826 (SEQ ID NO:16), 1827 (SEQ ID NO:17), 1844 (SEQ ID NO:32), 1845 (SEQ ID NO:33), 1846 (SEQ ID NO:34), 1848 (SEQ ID NO:36), 1849 (SEQ ID NO:37), 1850 (SEQ ID NO:38), 1851 (SEQ ID NO:39), 1852 (SEQ ID NO:40), 1853 (SEQ ID NO:41), 1855 (SEQ ID NO:42), 1857 (SEQ ID NO:45), 1858 (SEQ ID NO:46), 1859 (SEQ ID NO:47) (see Table 1).

On the other hand, compounds of the present invention that do not have these modifications, e.g. which comprise one or more substitutions at positions 10, 11 and/or 24, may be preferred for inducing preferential growth of the colon rather than the small intestine. They may therefore be used for treatment of conditions affecting or related to the colon.

Such colon-selective compounds may comprise more than one of the substitutions at positions X3, X8 and/or X24. For example, they may comprises more than one substitution selected from X3 is Asp, X8 is Asp and X24 is Ala. The amino acid residues in positions X31, X32 and X33 may optionally be deleted.

Exemplified compounds preferentially stimulating epithelial growth in the colon include 1830 (SEQ ID NO:20), 1831 (SEQ ID NO:21), 1835 (SEQ ID NO:25), 1836 (SEQ ID NO:26), 1839 (SEQ NO:27), 1840 (SEQ ID NO:28), 1841 (SEQ ID NO:29), and 1843 (SEQ ID NO:31).

Exemplified compounds without preferential growth in small intestine or colon: [Gly2]GLP-2 (i.e., reference molecule), 1559 (SEQ ID NO:54), 1821 (SEQ ID NO:11), 1822 (SEQ ID NO:12), 1823 (SEQ ID NO:13), 1825 (SEQ ID NO:15), 1828 (SEQ ID NO:18), 1829 (SEQ ID NO:19), 1832 (SEQ ID NO:22), 1833 (SEQ ID NO:23), 1834 (SEQ ID NO:24), 1842 (SEQ ID NO:30), 1854 (SEQ ID NO:42).

The compounds of the invention also have increased chemical stability, e.g. against acid hydrolysis, oxidation and deamidation. It is believed that substitutions at positions X3 and/or X33 may improve stability to acid hydrolysis. Substitution at position X10 may improve oxidative stability. Substitution at one or more positions X11, X16 and/or X24 may increase stability against deamidation. The GLP-2 analogue of the invention may therefore exhibit enhanced stability towards degradation in acidic solution, towards deamidation, and/or towards oxidative degradation, relative to Gly2-GLP-2. Preferably, the GLP-2 analogue maintains an observed purity of at least (40%, 50%, 60%, 70%, 80%, or 90%, 95%, or 99% relative to the initial purity in at least one of the degradation tests described in Example 7 below. Additionally or alternatively, it may maintain an observed purity of at least 60% relative to initial purity in a solution of HCl 0.1 M after 12 days. Additionally or alternatively it may maintain an observed purity of at least 70% relative to initial purity in a solution of NH4HCO3 0.1 M after 6 days.

In a further aspect, the present invention provides a composition comprising a GLP-2 analogue as defined herein, or a salt or derivative thereof, in admixture with a carrier. In preferred embodiments, the composition is a pharmaceutically acceptable composition and the carrier is a pharmaceutically acceptable carrier. The GLP-2 peptide analogue may be a pharmaceutically acceptable acid addition salt of the GLP-2 analogue.

In a further aspect, the present invention provides a GLP-2 analogue as defined herein, or a salt thereof, for use in therapy.

In a further aspect, the present invention provides use of a GLP-2 analogue, or a salt or derivative thereof for the preparation of a medicament for the treatment and/or prevention of stomach and bowel-related disorders, such as the treatment of neonatals with compromised intestine function, osteoporosis, and DPP-IV (dipeptidylpeptidase-IV) mediated conditions. By way of example, the stomach and bowel-related disorders include ulcers, gastritis, digestion disorders, malabsorption syndromes, short-gut syndrome, cul-de-sac syndrome, inflammatory bowel disease, celiac sprue (for example arising from gluten induced enteropathy or celiac disease), tropical sprue, hypogammaglobulinemic sprue, enteritis, regional enteritis (Crohn's disease), ulcerative colitis, irritable bowel syndrome associated with diarrhea, small intestine damage and short bowel syndrome.

Other conditions that may be treated with the GLP-2 analogues of the invention, or for which the GLP-2 analogues may be useful prophylactically or therapeutically, include radiation enteritis, infectious or post-infectious enteritis, and small intestinal damage due to toxic or other chemotherapeutic agents. This may require administration of the GLP-2 analogue prior to, concurrently with or following a course of chemotherapy or radiation therapy in order to reduce side effects of chemotherapy such as diarrhea, abdominal cramping and vomiting, and reduce the consequent structural and functional damage of the intestinal epithelium resulting from the chemotherapy or radiation therapy.

The invention therefore also provides a therapeutic kit comprising a cancer chemotherapy drug and a GLP-2 analogue of the present invention, each optionally in combination with a pharmaceutically acceptable carrier. The two therapeutic agents may be packaged separately (e.g. in separate vials) for separate administration, or may be provided in the same composition. Thus the invention further provides a pharmaceutical composition comprising a cancer chemotherapy drug and a GLP-2 analogue of the present invention in combination with a pharmaceutically acceptable carrier.

For patients having gastrointestinal mucosal neoplasia, or an increased risk of gastrointestinal mucosal neoplasia, it may be desirable to select a compound so as to reduce or abrogate the risk of reduced side effects such as stimulation or aggravation of gastrointestinal mucosal neoplasia. For example, when selecting a compound for treating a patient with colon neoplasia (whether benign or malignant), or at risk of developing colon neoplasia, it may be more appropriate to select a compound which is selective for the small intestine over the colon than a non-selective compound or a compound which is selective for the colon over the small intestine.

In other aspects, the present invention provides the use of the GLP-2 analogues for the preparation of a medicament for the treatment and/or prevention of malnutrition, for example conditions such as the wasting syndrome cachexia and anorexia.

In a further aspect, the present invention provides a nucleic acid molecule comprising a nucleic acid sequence encoding a GLP-2 analogue of as defined herein.

In further aspects, the present invention provides an expression vector comprising the above nucleic acid sequence, optionally in combination with sequences to direct its expression, and host cells transformed with the expression vectors. Preferably the host cells are capable of expressing and secreting the GLP-2 analogue. In a still further aspect, the present invention provides a method of producing the GLP-2 analogue, the method comprising culturing the host cells under conditions suitable for expressing the GLP-2 analogue and purifying the GLP-2 analogue thus produced.

The invention further provides a nucleic acid of the invention, an expression vector of the invention, or a host cell capable of expressing and secreting a GLP-2 analogue of the invention, for use in therapy. It will be understood that the nucleic acid, expression vector and host cells may be used for treatment of any of the disorders described herein which may be treated with the GLP-2 analogues themselves. References to a therapeutic composition comprising a GLP-2 analogue of the invention, or administration of a GLP-2 analogue of the invention, should therefore be construed to encompass administration of a nucleic acid, expression vector or host cell of the invention except where the context demands otherwise.

In a further aspect, the present invention provides a method of treating a stomach and bowel-related disorder in a patient in need thereof by administering an effective amount a GLP-2 analogue as defined herein, or a salt or derivative thereof, or a nucleic acid, expression vector or host cell of the invention. Examples of stomach and bowel-related disorders are provided above.

In a further aspect, the present invention provides a method of treating or preventing a side effect of chemotherapy or radiation therapy in a patient in need thereof, the method comprising administering an effective amount a GLP-2 analogue as defined herein, or a salt or derivative thereof, or a nucleic acid, expression vector or host cell of the invention.

In a further aspect, the present invention provides a method of treating or preventing malnutrition, for example conditions such as the wasting syndrome cachexia and anorexia, in a patient in need thereof, the method comprising administering an effective amount a GLP-2 analogue as defined herein, or a salt or derivative thereof, or a nucleic acid, expression vector or host cell of the invention.

Embodiments of the present invention will now be described in more detail by way of examples and not limitation with reference to the accompanying figures.

Results demonstrated that within the dose range 5-405 nmol/kg, the dose-response relationships of the small intestine selective compounds 1857 (SEQ ID NO:45), 1820 (SEQ ID NO:10), and 1849 (SEQ ID NO:37) were significantly different from the non-selective reference compound [Gly2] GLP-2 (SEQ ID NO:54) ($p<0.05$ in two-way ANOVA) and all three compounds demonstrated increased maximal small intestinal sensitivity relative to [Gly2]GLP-2 (SEQ ID NO:54). Values are means±SEM. *:$P<0.05$ relative to the equimolar dose of [Gly2]GLP-2 (SEQ ID NO:54).

Figure 1:
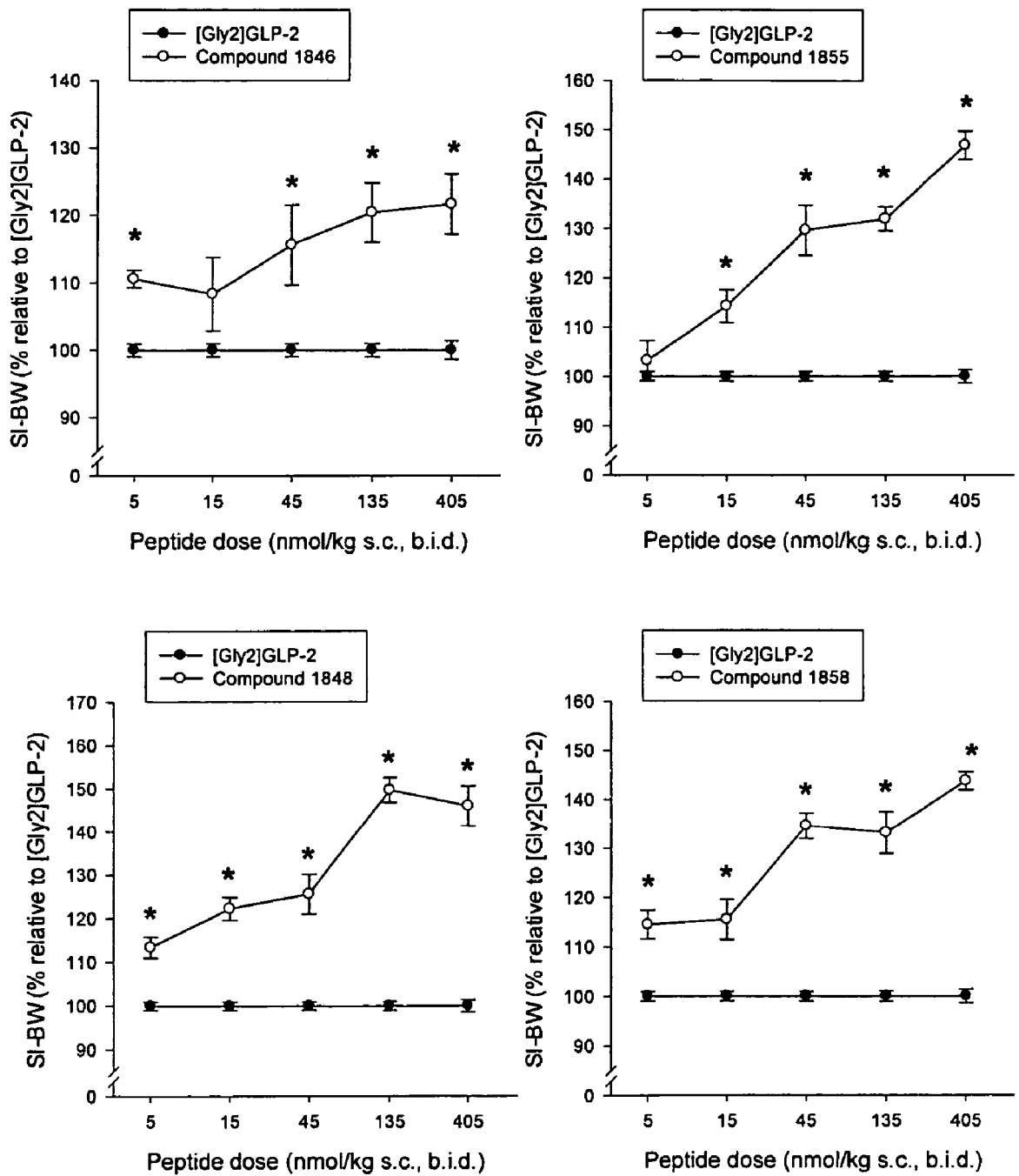
FIG. 1 is a set of graphs showing full dose-response data of four small intestine selective compounds (compound nos. 1846 (SEQ ID NO:34), 1855 (SEQ ID NO:43), 1848 (SEQ ID NO:36), and 1858 (SEQ ID NO:46) on small intestinal (SI) mass in C57BL mice. Compounds were administered by subcutaneous injection b.i.d. for three days at the following doses: 0 (vehicle), 5, 15, 45, 135, 405 nmol/kg (n=6/dose group). Responses at each dose level were compared with responses obtained at the same dose level in pair-treated mice treated with the non-selective reference compound [Gly2] GLP-2 (SEQ ID NO:54). To correct for changes in body weight (BW), SI mass was expressed relative to BW (SI-BW ratio) and the growth response at each dose level was normalized to the response observed with the non-selective reference compound [Gly2]GLP-2 (SEQ ID NO:54). Results demonstrated that within the dose range 5-405 nmol/kg, the dose-response relationships of the small intestine selective compounds 1846 (SEQ ID NO:34), 1855 (SEQ ID NO:43), 1848 (SEQ ID NO:36), and 1858 (SEQ ID NO:46) were significantly different from the non-selective reference compound [Gly2]GLP-2 (SEQ ID NO:54) ($p<0.05$ in two-way ANOVA) and all four compounds stimulated small intestinal growth with maximal responses that were significant greater than [Gly2]GLP-2 (SEQ ID NO:54). Values are means±SEM. *:$P<0.05$ relative to the equimolar dose of [Gly2]GLP-2 (SEQ ID NO:54).
Figure 2:
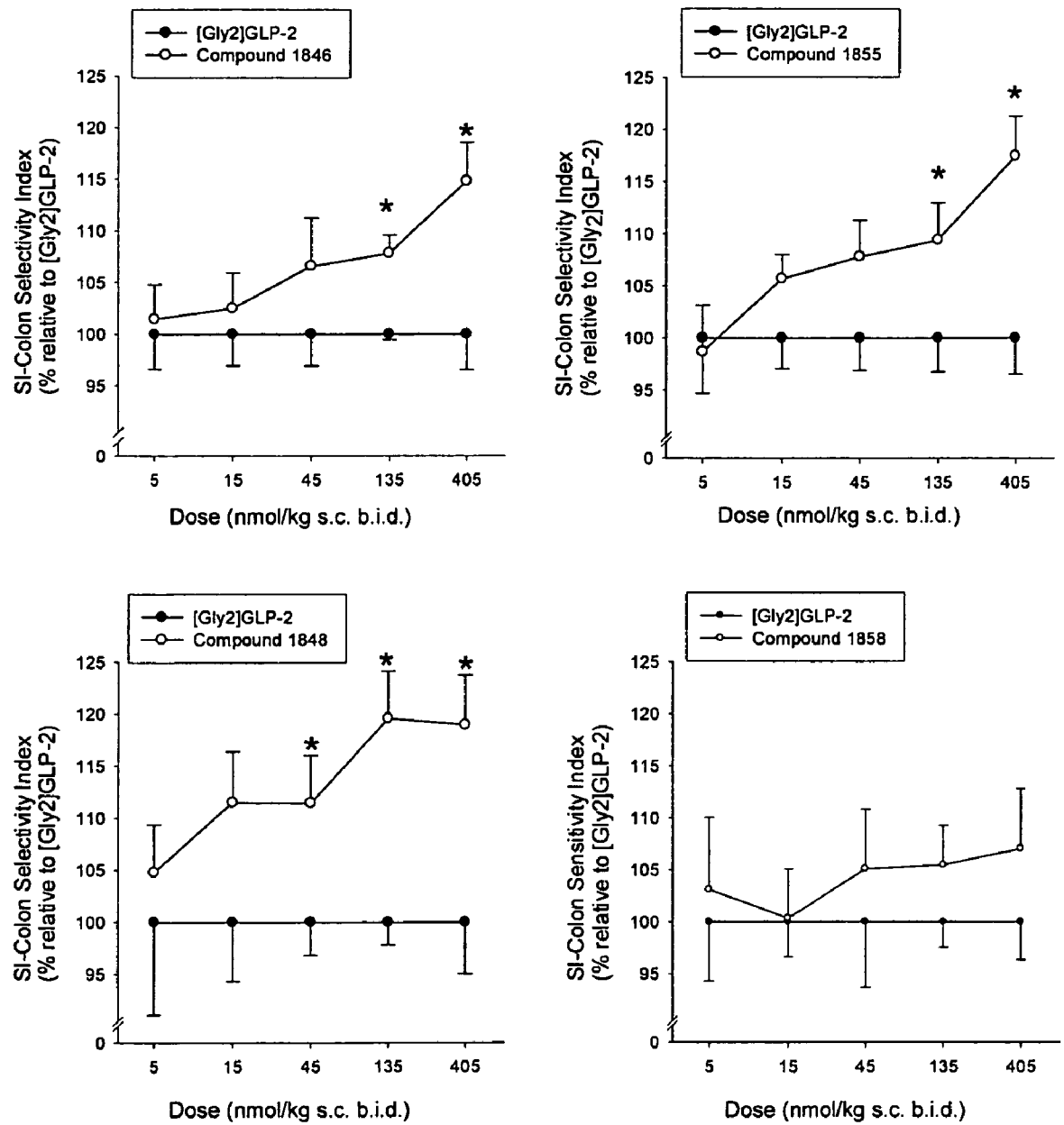
FIG. 2 is a set of graphs showing full dose-response data of four small intestine selective compounds (compound nos. 1846 (SEQ ID NO:34), 1855 (SEQ ID NO:43), 1848 (SEQ ID NO:36), 1858 (SEQ ID NO:46)) on the Small Intestine (SI)-to-Colon Sensitivity Index mice relative to the non-selective reference compound [Gly2]GLP-2 (SEQ ID NO:54). Compounds were administered by subcutaneous injection b.i.d. for three days in C57BL mice at the following doses: 0 (vehicle), 5, 15, 45, 135, 405 nmol/kg (n=6/dose group). Responses at each dose level were compared with responses obtained at the same dose level in pair-treated mice treated with the non-selective reference compound [Gly2]GLP-2 (SEQ ID NO:54). The SI-Colon Sensitivity Index was calculated as SI-mass relative to colon mass and the Sensitivity Index at each dose level was normalized to the response observed with the non-selective reference compound [Gly2]GLP-2 (SEQ ID NO:54). Results demonstrated that within the dose range 5-405 nmol/kg, the dose-response relationships of the small intestine selective compounds 1857 (SEQ ID NO:45) and 1820 (SEQ ID NO:10) were significantly different from the non-selective reference compound [Gly2] GLP-2 (SEQ ID NO:54) ($p<0.05$ in two-way ANOVA) and compounds 1846 (SEQ ID NO:34), 1855 (SEQ ID NO:43), and 1848 (SEQ ID NO:36) demonstrated increased maximal small intestinal sensitivity relative to [Gly2]GLP-2. Values are means±SEM. *:$P<0.05$ relative to the equimolar dose of [Gly2]GLP-2.
Figure 3:
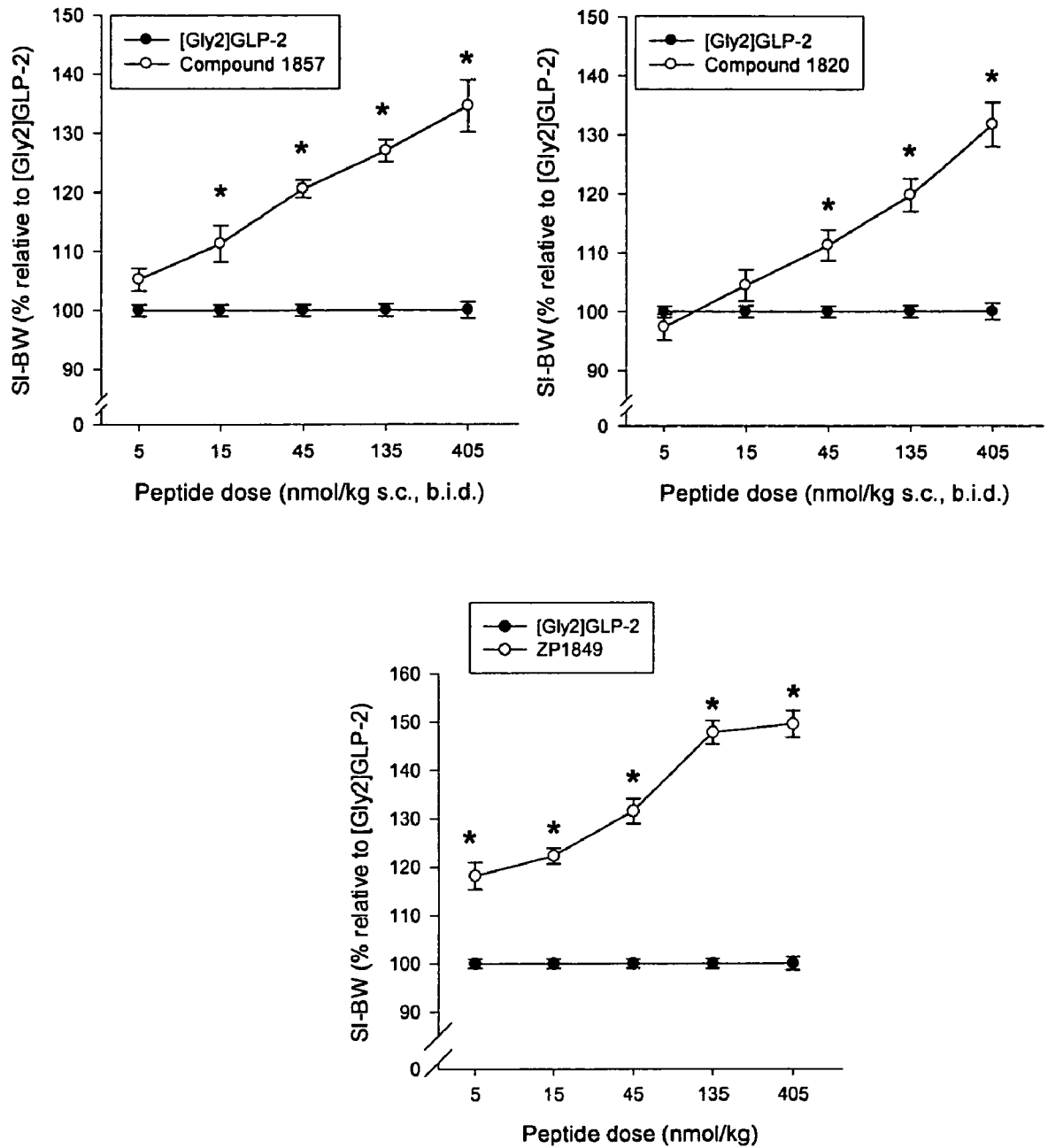
FIG. 3 is a set of graphs showing full dose-response data of two small intestine selective compounds (compound nos. 1857 (SEQ ID NO:45), 1849 (SEQ ID NO:37), and 1820 (SEQ ID NO:10) on small intestinal (SI) mass in C57BL mice. Compounds were administered by subcutaneous injection b.i.d. for three days at the following doses: 0 (vehicle), 5, 15, 45, 135, 405 nmol/kg (n=6/dose group). Responses at each dose level were compared with responses obtained at the same dose level in pair-treated mice treated with the non-selective reference compound [Gly2]GLP-2. To correct for changes in body weight (BW), SI mass was expressed relative to BW (SI-BW ratio) and the growth response at each dose level was normalized to the response observed with the non-selective reference compound [Gly2]GLP-2 (SEQ ID NO:54). Results demonstrated that within the dose range 5-405 nmol/kg, the dose-response relationships of the small intestine selective compounds 1857 (SEQ ID NO:45), 1849 (SEQ ID NO:37), and 1820 (SEQ ID NO:10) were significantly different from the non-selective reference compound [Gly2]GLP-2 (SEQ ID NO:54) ($p<0.05$ in two-way ANOVA) and both compounds stimulated small intestinal growth with maximal responses that were significant greater than [Gly2] GLP-2 (SEQ ID NO:54). Values are means±SEM. *:$P<0.05$ relative to the equimolar dose of [Gly2]GLP-2 (SEQ ID NO:54).
Figure 4:
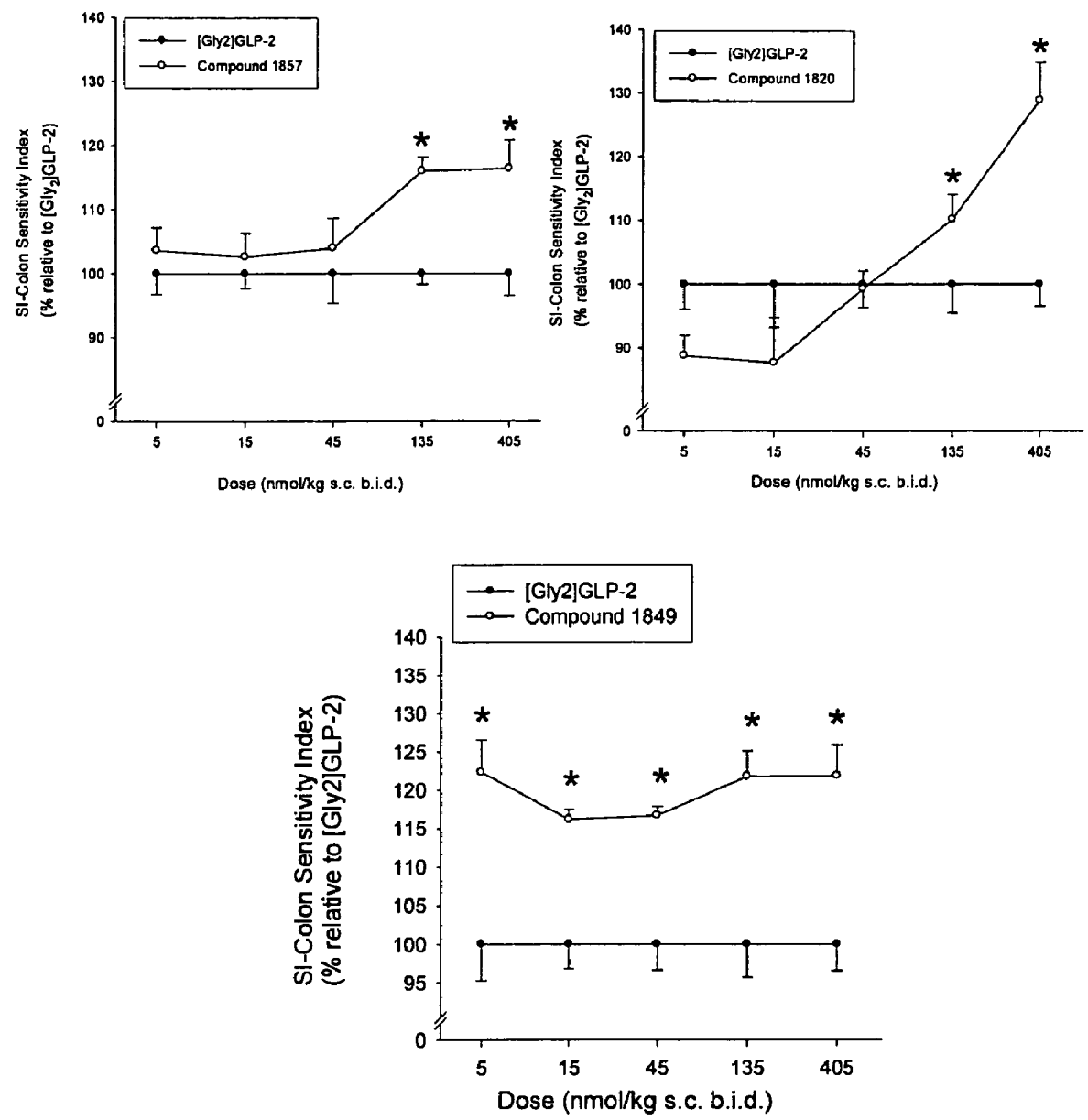
FIG. 4 is a set of graphs showing full dose-response data of three small intestine selective compounds (compound nos. 1857 (SEQ ID NO:45), 1820 (SEQ ID NO:10), and 1849 (SEQ ID NO:37)) on the Small Intestine (SI)-to-Colon Sensitivity Index mice relative to the non-selective reference compound [Gly2]GLP-2 (SEQ ID NO:54). Compounds were administered by subcutaneous injection b.i.d. for three days in C57BL mice at the following doses: 0 (vehicle), 5, 15, 45, 135, 405 nmol/kg (n=6/dose group). Responses at each dose level were compared with responses obtained at the same dose level in pair-treated mice treated with the non-selective reference compound [Gly2]GLP-2 (SEQ ID NO:54). The SI-Colon Sensitivity Index was calculated as SI-mass relative to colon mass and the Sensitivity Index at each dose level was normalized to the response observed with the non-selective reference compound [Gly2]GLP-2 (SEQ ID NO:54).
Figure 5:
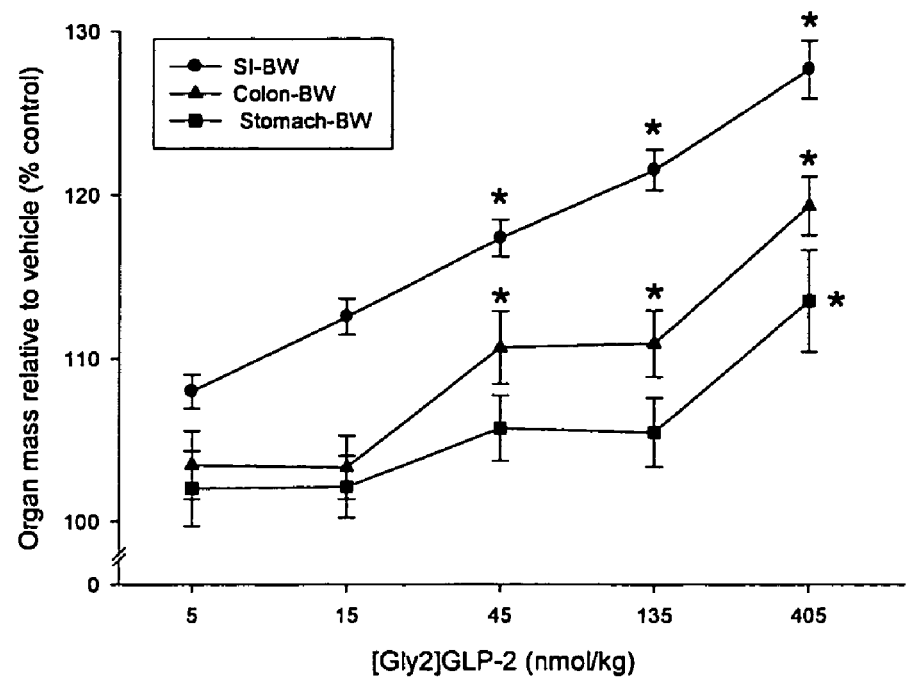
Figure 5:
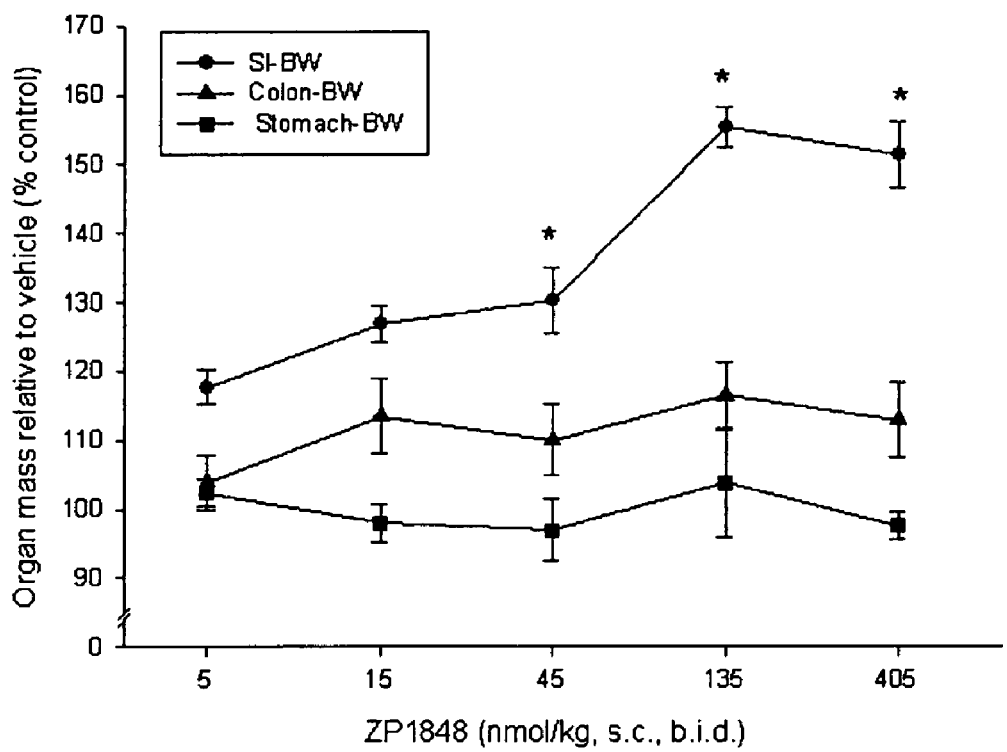

FIG. 5 shows examples of full dose-response data of a non-selective compound ([Gly2]GLP-2 (SEQ ID NO:54)), and a small intestine selective compound (Compound 1848 (SEQ ID NO:36)), on small intestine, colon and stomach mass. Compounds were administered by subcutaneous injection b.i.d. for three days in C57BL mice at the following doses: 0 (vehicle), 5, 15, 45, 135, 405 nmol/kg (n=6/dose group). Results demonstrated that within the dose range 5-405 nmol/kg, [Gly2]GLP-2 (SEQ ID NO:54) produced dose-dependent growth stimulation in small intestine, colon and stomach, while Compound 1848 (SEQ ID NO:36) only produced dose-dependent growth stimulation in the small intestine. Values are means±SEM. *:$P<0.05$ relative to the vehicle.

Figure 6:
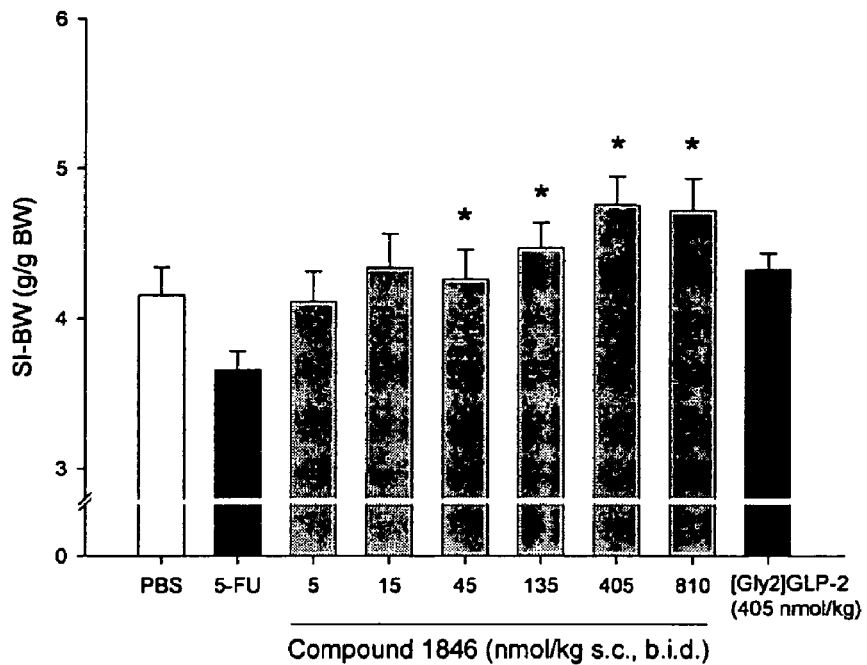
Figure 6:
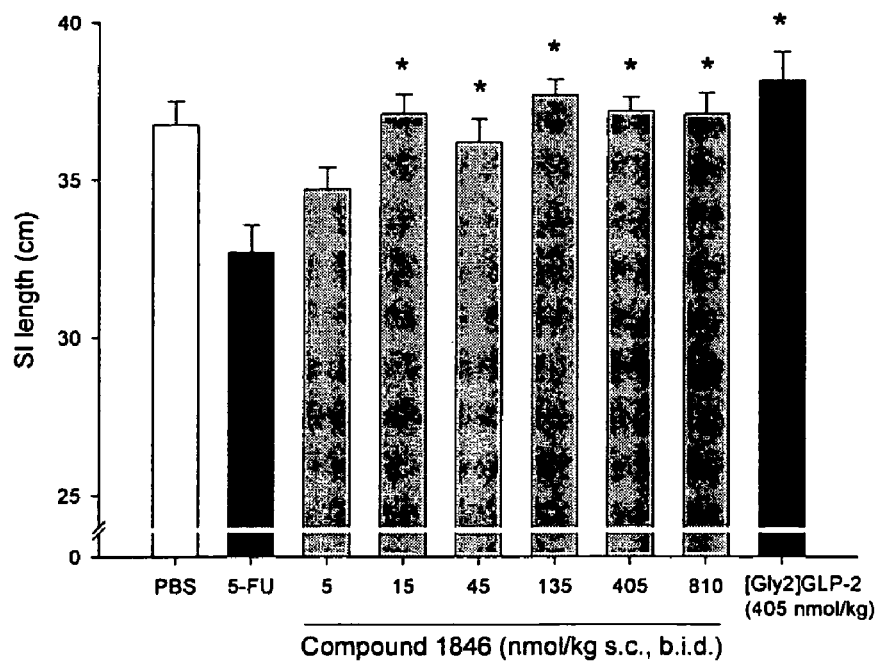

FIG. 6 is a set of graphs showing the effect of compound 1846 (SEQ ID NO:34) (5, 15, 45, 135, 405 and 810 nmol/kg, s.c., b.i.d.; n=6/dose group) on A) small intestine-to-body weight ratio (SI-BW), and B) small intestinal length (SI length) in mice treated with the cytostatic drug 5-Fluorouracil (5-FU). Compound 1846 (SEQ ID NO:34) was administered for 3 days prior to and for 4 days together with 5-FU, 50 mg/kg, i.p. daily. For reference, [Gly2]GLP-2 (SEQ ID NO:54) (405 nmol/kg) was given to one group of animals. Results from control animals treated with vehicle (PBS) or 5-FU alone are also shown. Compound 1846 (SEQ ID NO:34) prevented 5-FU-induced small intestine atrophy (reduced organ mass and shortening) in C57BL mice. Values are means±SEM. *$P<0.05$, relative to 5-FU.

Figure 7:
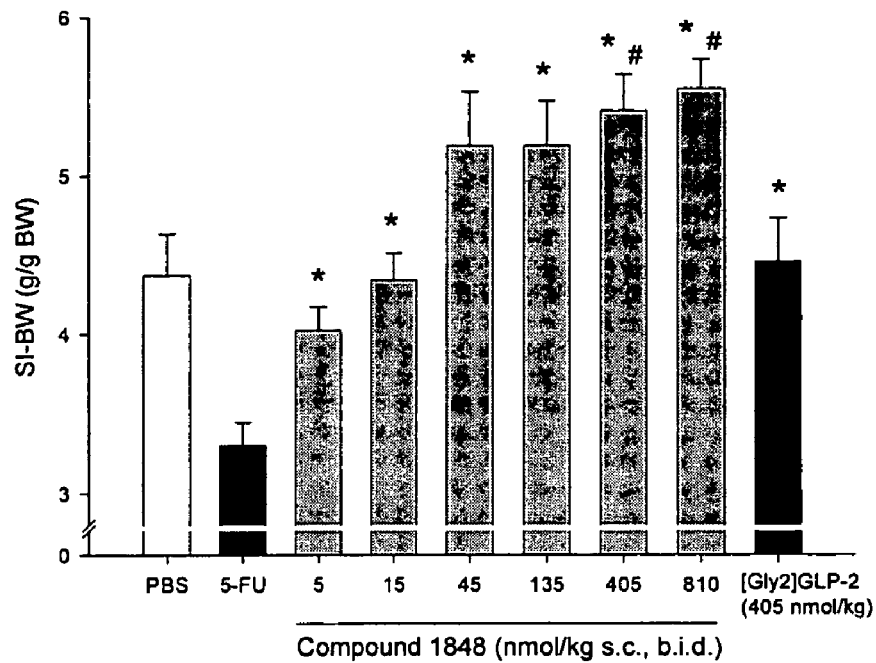
Figure 7:
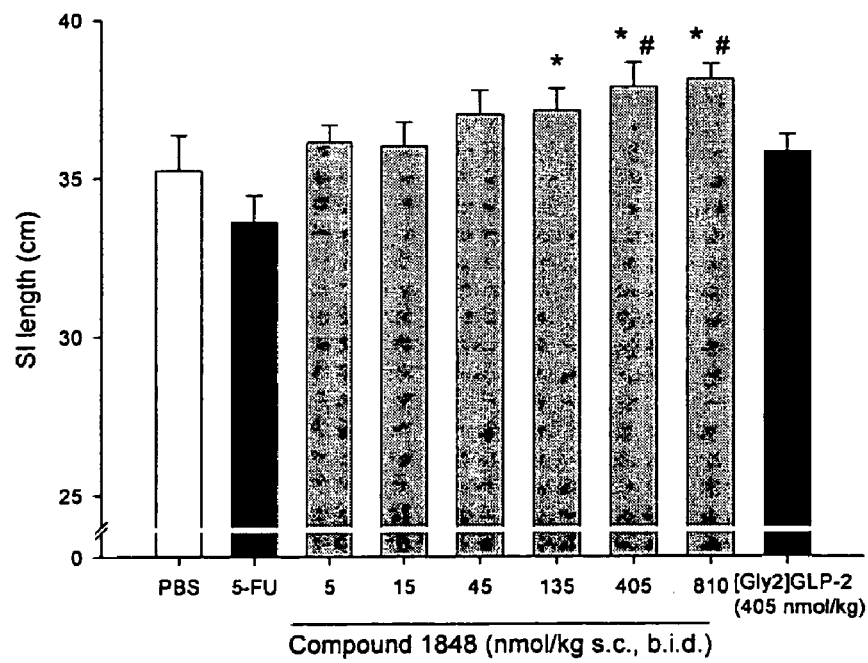

FIG. 7 is a set of graphs showing the effect of compound 1848 (SEQ ID NO:36) (5, 15, 45, 135, 405 and 810 nmol/kg, s.c., b.i.d.; n=6/dose group) on A) small intestine-to-body weight ratio (SI-BW), and B) small intestinal length (SI length) in mice treated with the cytostatic drug 5-Fluorouracil (5-FU). Compound 1848 (SEQ ID NO:36) was administered for 3 days prior to and for 4 days together with 5-FU, 50 mg/kg, i.p. daily. For reference, [Gly2]GLP-2 (SEQ ID NO:54) (405 nmol/kg) was given to one group of animals. Results from control animals treated with vehicle (PBS) or 5-FU alone are also shown. Compound 1848 (SEQ ID NO:36) prevented 5-FU-induced small intestine atrophy (reduced organ mass and shortening) in C57BL mice and high doses of compound 1848 (SEQ ID NO:36) were more efficacious than [Gly2]GLP-2. Values are means±SEM. *P<0.05, relative to 5-FU. #P<0.05, relative to [Gly2]GLP-2.

Figure 8:
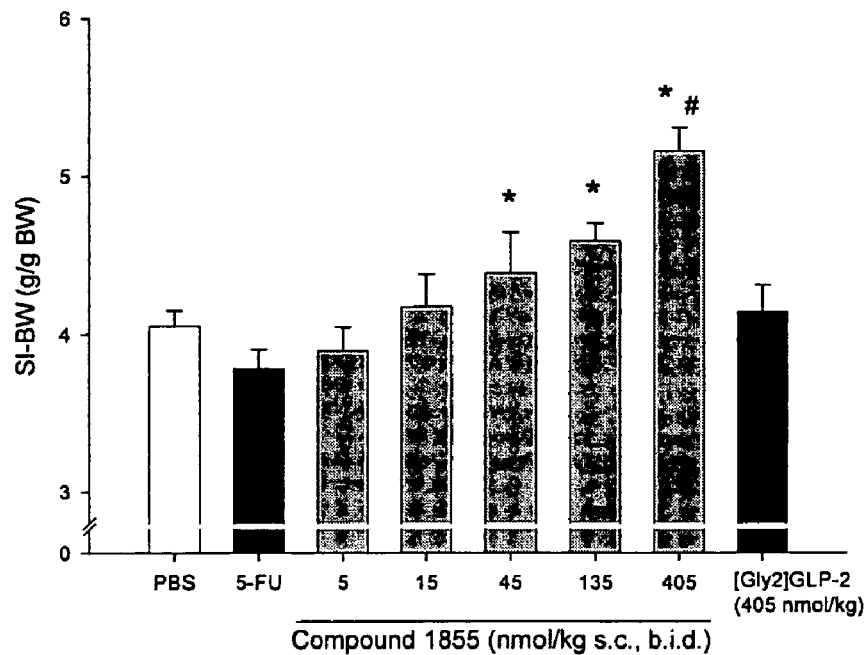
Figure 8:
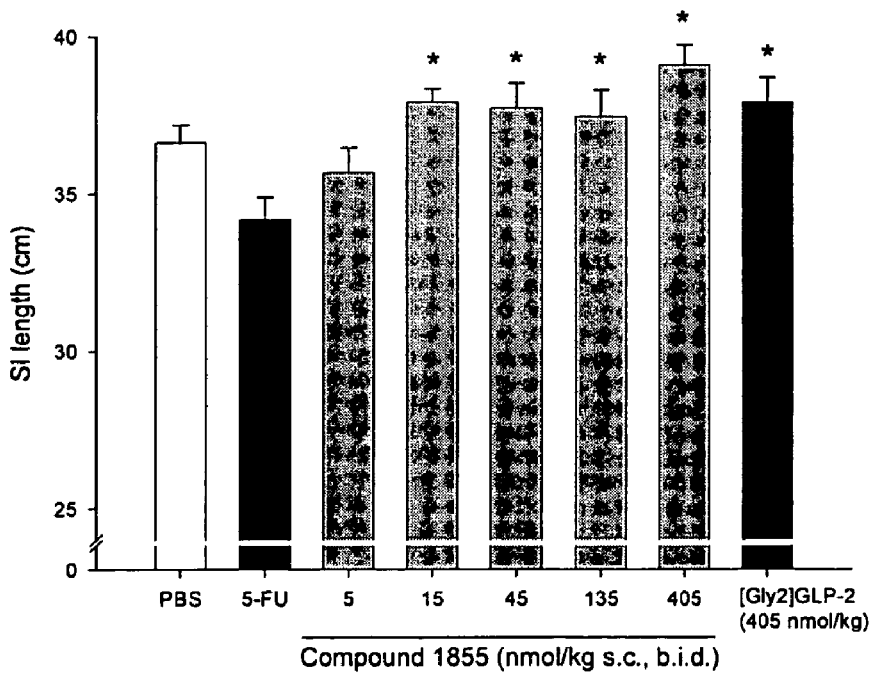

FIG. 8 is a set of graphs showing the effect of compound 1855 (SEQ ID NO:43) (5, 15, 45, 135, and 405 nmol/kg, s.c., b.i.d.; n=6/dose group) on A) small intestine-to-body weight ratio (SI-BW), and B) small intestinal length (SI length) in mice treated with the cytostatic drug 5-Fluorouracil (5-FU). Compound 1855 (SEQ ID NO:43) was administered for 3 days prior to and for 4 days together with 5-FU, 50 mg/kg, i.p. daily. For reference, [Gly2]GLP-2 (405 nmol/kg) was given to one group of animals. Results from control animals treated with vehicle (PBS) or 5-FU alone are also shown. Compound 1855 (SEQ ID NO:43) prevented 5-FU-induced small intestine atrophy (reduced organ mass and shortening) in C57BL mice and the highest dose of compound 1855 (SEQ ID NO:43) was more efficacious than the equimolar dose of [Gly2]GLP-2 (SEQ ID NO:54). Values are means±SEM. *P<0.05, relative to 5-FU. #P<0.05, relative to [Gly2]GLP-2 (SEQ ID NO:54).

Figure 9:
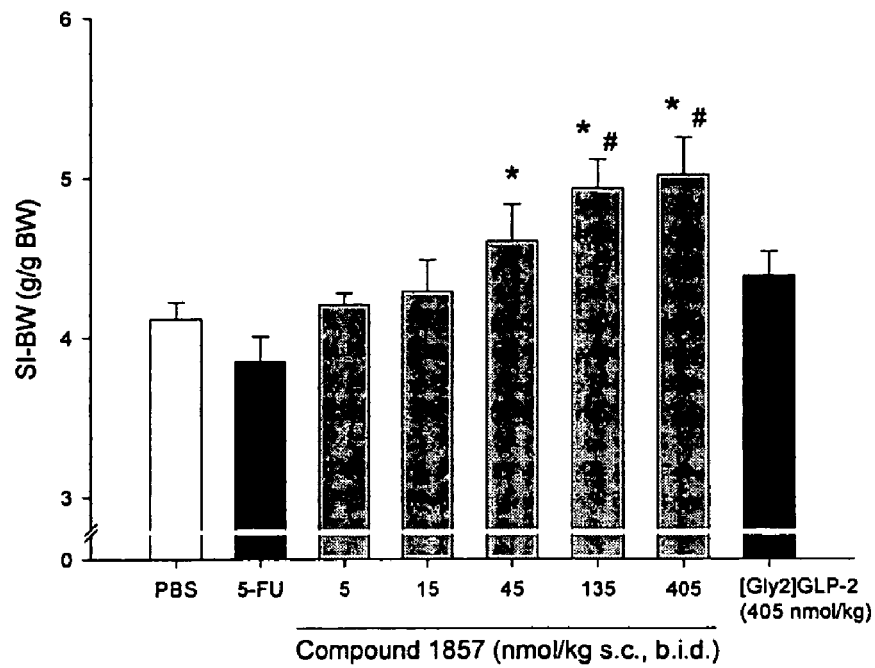
Figure 9:
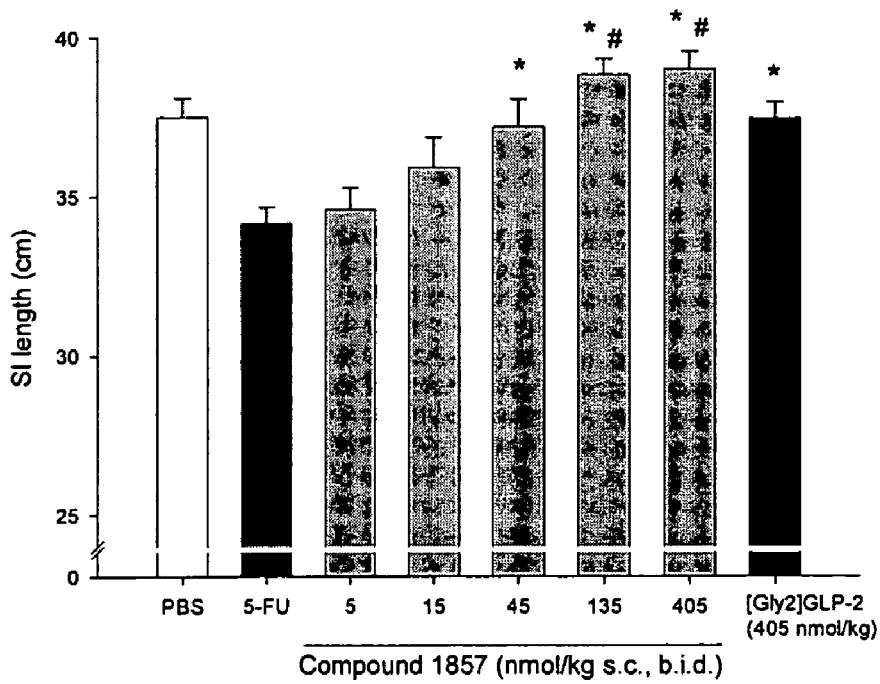

FIG. 9 is a set of graphs showing the effect of compound 1857 (SEQ ID NO:45) (5, 15, 45, 135, and 405 nmol/kg, s.c., b.i.d.; n=6/dose group) on A) small intestine-to-body weight ratio (SI-BW), and B) small intestinal length (SI length) in mice treated with the cytostatic drug 5-Fluorouracil (5-FU). Compound 1857 (SEQ ID NO:45) was administered for 3 days prior to and for 4 days together with 5-FU, 50 mg/kg, i.p. daily. For reference, [Gly2]GLP-2 (SEQ ID NO:54) (405 nmol/kg) was given to one group of animals. Results from control animals treated with vehicle (PBS) or 5-FU alone are also shown. Compound 1857 (SEQ ID NO:45) prevented 5-FU-induced small intestine atrophy (reduced organ mass and shortening) in C57BL mice and the highest doses of compound 1855 (SEQ ID NO:43) were more efficacious than a high dose of [Gly2]GLP-2 (SEQ ID NO:54). Values are means±SEM. *P<0.05, relative to 5-FU. #P<0.05, relative to [Gly2]GLP-2 (SEQ ID NO:54).

Figure 10:
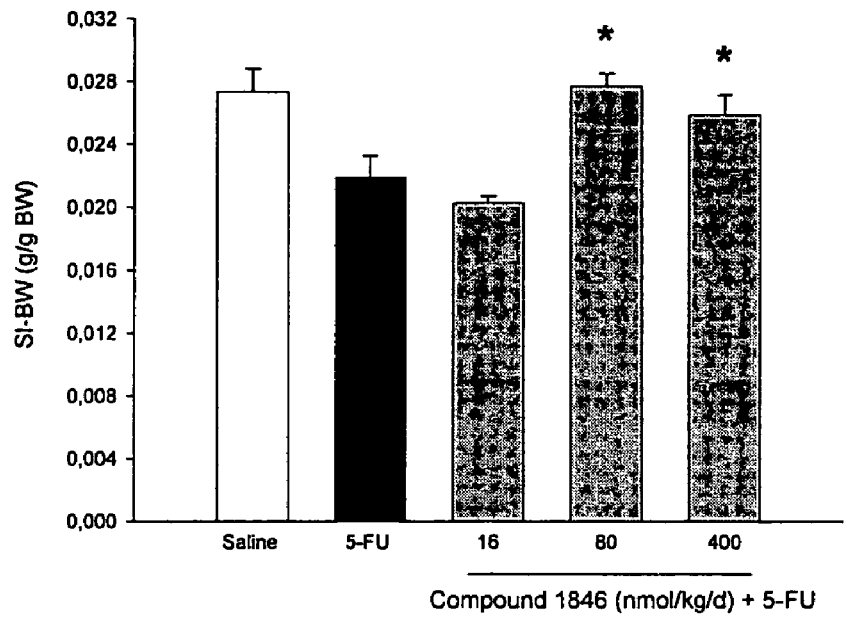
Figure 10:
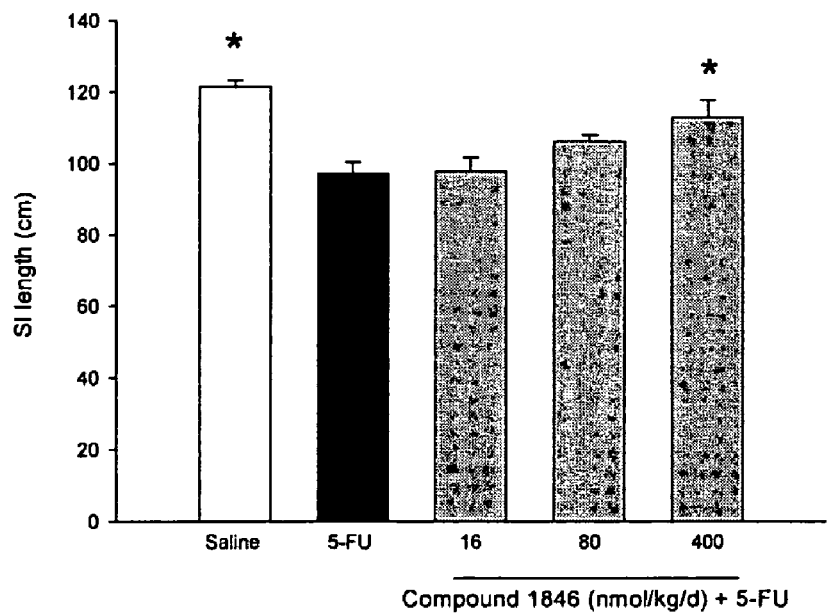

FIG. 10 is a set of graphs showing effects of compound 1846 (SEQ ID NO:34) (16, 80 and 400 nmol/kg/d; s.c., n=6/dose group) in male Spague-Dawley rats treated with the cytostatic drug 5-Fluorouracil (5-FU). Compound 1846 (SEQ ID NO:34) was administered for 3 days prior to and for 4 days together with 5-FU (75 mg/kg, i.p. daily). Results were compared with responses in control animals treated with vehicle (saline) or 5-FU alone. Saline and 5-FU controls are also shown. Compound 1846 (SEQ ID NO:34) prevented 5-FU-induced small intestine atrophy (reduced small intestinal mass and intestinal shortening) in rats. Values are means±SEM. *P<0.05, relative to 5-FU alone.

Figure 11:
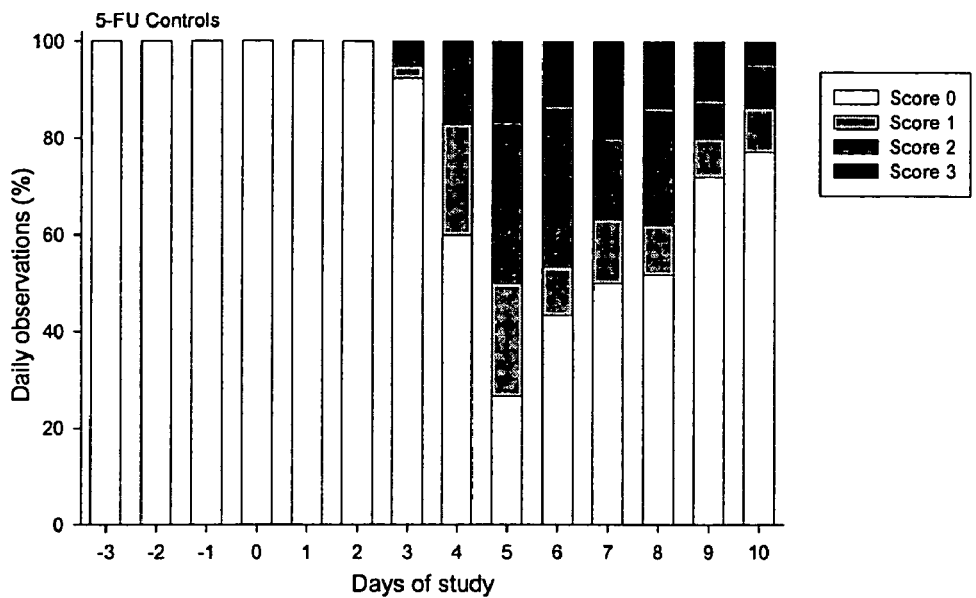
Figure 11:
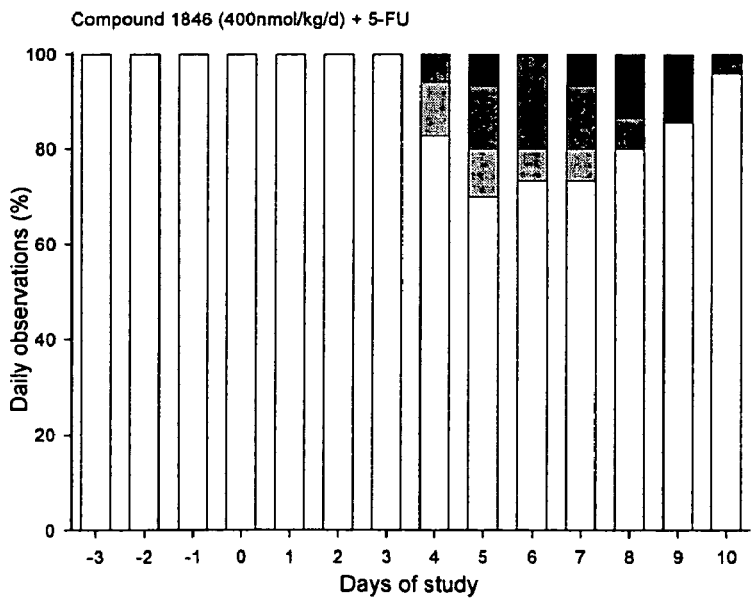

FIG. 11 is a set of graphs showing the therapeutic effect of compound 1846 (SEQ ID NO:34) on diarrhea induced by treatment with the cytostatic drug 5-fluorouracil (5-FU). Rats were treated with 5-FU for 4 days with 75 mg/kg once daily (days 1-4); (n=40 rats). Half of the animals received additional treatment with compound 1846 (SEQ ID NO:34) (400 nmol/kg s.c. once daily) during the last 3 days prior to (days −3 to −1) and during 4 days of 5-FU treatment (days 0 to 3). Rats were observed twice daily (morning and evening) to determine whether the animal had diarrhea and the severity of the diarrhea was scored according to this scale: (0) no diarrhea; (1) mild—fecal staining around the anus; (2) moderate—fecal staining on the hind limbs and tail; and (3) severe—fecal staining on the front limbs and abdomen. On day 5, about 70% of Sprague Dawley rats that received 5-FU alone had developed diarrhea (FIG. 11A) while only 30% of the rats that were co-treated with compound 1846 (SEQ ID NO:34) developed diarrhea (FIG. 11B). These results indicate that compound 1846 (SEQ ID NO:34) effectively prevents injury of the small intestine and thus the development of diarrhea during cytostatic treatment with 5-FU.

Figure 12:
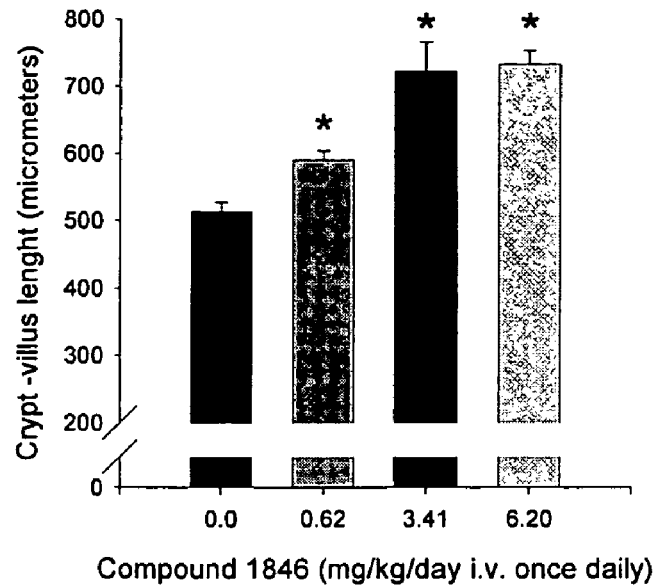
Figure 12:
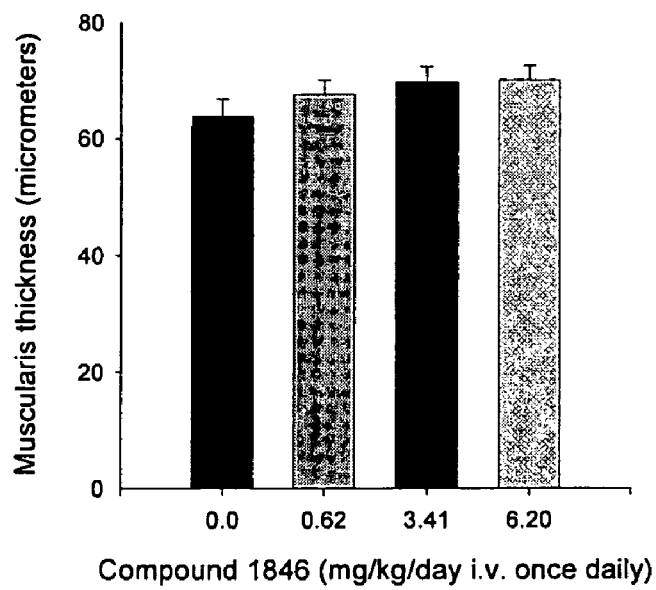

FIG. 12 is a set of graphs showing the effect of compound 1846 (SEQ ID NO:34) on epithelial crypt-villus height (FIG. 12A) and muscular thickness (FIG. 12B) in the jejunum (i.e., mid section of the small intestine). Sprague Dawley rats were treated intravenously with compound 1846 (SEQ ID NO:34) (0.62, 3.41 or 6.2 mg/kg once daily) for 5 days (n=6/dose group). Then the animals were sacrificed and small intestinal biopsies (1 cm) were collected 25 cm distal from the pyloric sphincter. The biopsies were fixed, embedded in paraffin, sectioned and stained with haematoxylin and eosin. Stained sections were examined under a microscope and crypt depth, villus height, crypt-villus length and muscularis thickness measured. As illustrated compound 1846 (SEQ ID NO:34) produced dose-dependent increases in crypt-villus length in intestinal epithelium from the jejunum, but had no effect on the muscular thickness of the jejunum. These results suggest that compound 1846 (SEQ ID NO:34) primarily exerts its proliferative actions in the small intestine through stimulation of small epithelial growth. Values are means±SEM. *P<0.05, relative to vehicle controls (0 mg/kg/d).

Figure 13:
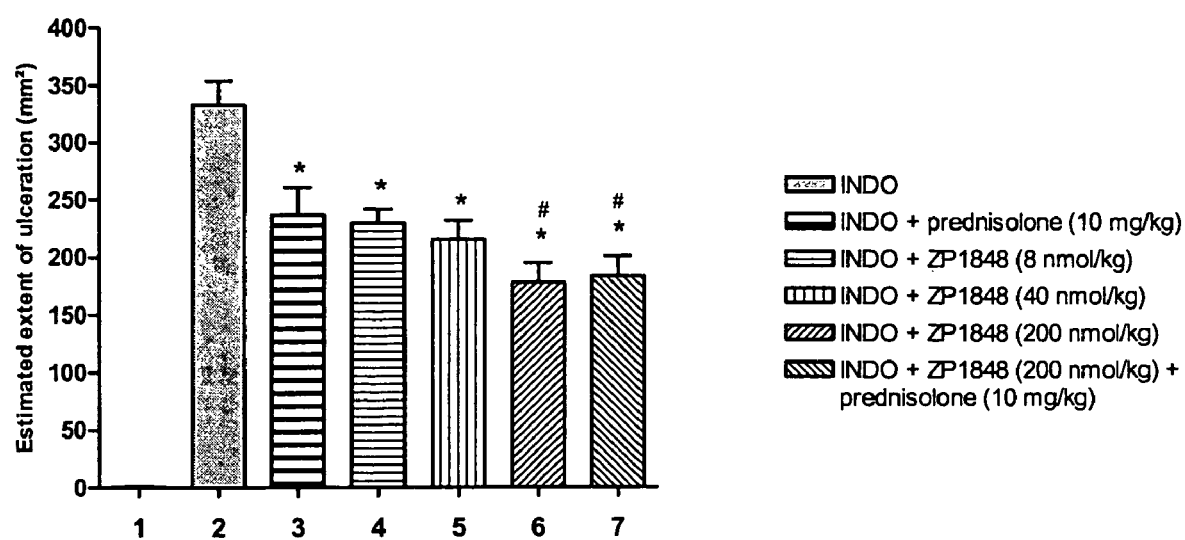

FIG. 13 is a graph illustrating the effect of compound 1848 (SEQ ID NO:36) on small intestinal ulcers induced by indomethacin. Male Sprague Dawley rats were treated with vehicle (saline; group 1) or indomethacin (7 mg/kg s.c., once daily for two days; groups 2-7). Indomethacin was given alone (group 2) or in combination with prednisolone (10 mg/kg s.c.; group 3) or with 8, 40, or 200 nmol/kg compound 1848 (SEQ ID NO:36) s.c. once daily (groups 4-6). Finally, one group of rats was treated with combination treatment of prednisolone (10 mg/kg s.c.) and compound 1848 (SEQ ID NO:36), 200 nmol/kg s.c. once daily (group 7). Treatment with compound 1848 (SEQ ID NO:36) was initiated 4 days prior to indomethacin and continued during the two days of indomethacin treatment. On day 3, rats were sacrificed and upon necropsy, the small intestine was gently flushed with 10% formalin and filled with formalin for a period of 5 minutes, after which the intestine was cut open along the antimesenteric margin and suspended on a polypropylene plate. Any remaining intestinal contents were carefully removed with a pair of tweezers. After fixation for another 24 hours at room temperature, the tissue was rinsed in Milli-Q water and surface-stained for 20 minutes with Alcian Green 3BX (Chroma) prepared as a 0.5% solution in 1% acetic acid (Bie & Berntsen). After removal of excess staining solution with Milli-Q water the tissue preparation was transferred to 70% alcohol and analyzed using a stereomicroscope at low magnification (×7). Starting at the pylorus, the small intestine was scanned and the shape (circular vs. linear) and size (circular ulcers: diameter, linear ulcers: length×width) of all ulcers was measured using a standard ruler (resolution: 0.5 mm). An ulcer was defined as an area, which lacked epithelial surface. In healing ulcers only the area that still lacked epithelial surface was regarded an ulcer even if the villus structure was still missing in a larger area. All analysis was performed in a blinded manner. As illustrated in FIG. 13, indomethacin caused a strong induction of small intestinal ulcers (total small intestinal ulceration=333±21 $mm^2$). Treatment with prednisolone caused a significant reduction in the extent of ulceration by app. 29%. Treatment with compound 1848 (SEQ ID NO:36) prevented indomethacin-induced ulceration in a dose-dependent fashion and at the highest dose the total ulceration was reduced by almost 50% (178±17 mm²). This maximal response to compound 1846 (SEQ ID NO:34) was greater than the effect of prednisolone and addition of prednisolone in combination with high dose compound 1848 (SEQ ID NO:36) did not produced any additional effect. These results indicate that compound 1848 (SEQ ID NO:36) effectively prevents indomethacin-induced ulceration in the small intestine. Values are means±SEM. *P<0.05 vs. indomethacin (group 2). #P<0.05 vs. prednisolone (group 3).

Figure 14:
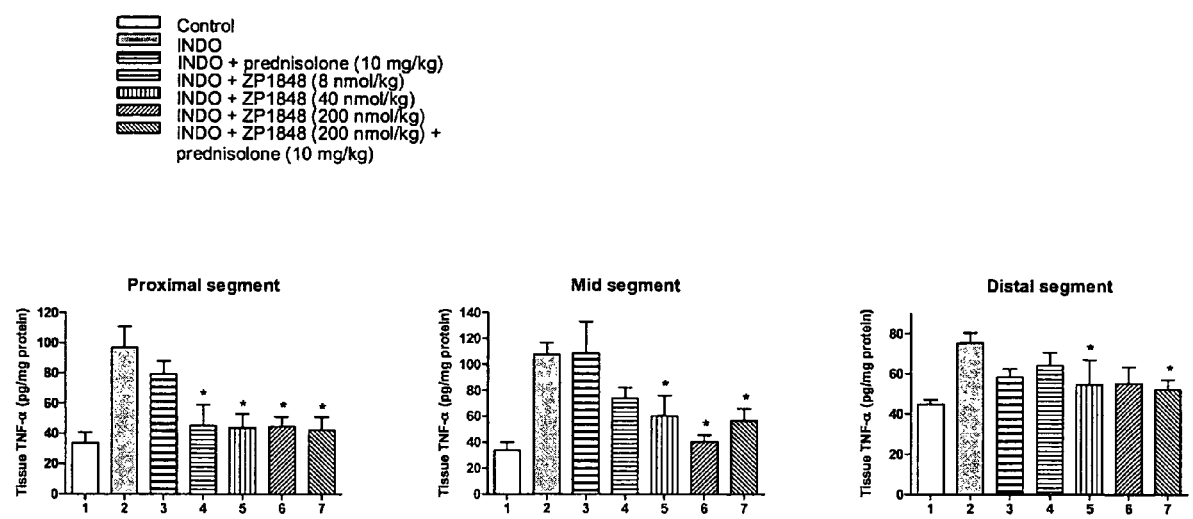

FIG. 14 is a set of graphs showing the effect of compound 1848 (SEQ ID NO:36) on small intestinal content of TNF-alpha in rats with indomethacin-induced inflammation in the small intestine. Male Sprague Dawley rats were treated with vehicle (saline; group 1) or indomethacin (7 mg/kg s.c., once daily for two days; groups 2-7). Indomethacin was given alone (group 2) or in combination with prednisolone (10 mg/kg s.c.; group 3) or with 8, 40, or 200 nmol/kg compound 1848 (SEQ ID NO:36) s.c. once daily (groups 4-6). Finally, one group of rats was treated with combination treatment of prednisolone (10 mg/kg s.c.) and compound 1848 (SEQ ID NO:36), 200 nmol/kg s.c. once daily (group 7). Treatment with compound 1848 (SEQ ID NO:36) was initiated 4 days prior to indomethacin and continued during the two days of indomethacin treatment. On day 3, rats were sacrificed and upon necropsy, the small intestine Upon necropsy the small intestine was divided into three segments of equal length corresponding to 1) duodenum and proximal jejunum, 2) mid and distal jejunum and 3) ileum. Samples were immediately snap-frozen in liquid $N_2$ and stored at −80° C. until analysis. Homogenization and extraction of cellular protein from small intestinal segments was performed according to the following procedure: Tissue segments were weighed and added a volume of 1.5 ml per gram tissue ice-cold (4° C.) extraction buffer (10 mM Tris-HCl (Sigma) and 1 mM EDTA (J.T. Baker), (pH 7.6) with 0.05% sodium azide (Fluka), 1% Tween-80 (Fluka), 2 mM phenylmethylsulfonyl fluoride (PMSF, Fluka) and 1 µg/ml of each of the protease inhibitors aprotinin, leupeptin and pepstatin A (Roche Diagnostics)). The tissue was cut into small bits with a pair of scissors and homogenized three times for 20 seconds (IKA UltraTurrax T25 homogenizer, Janke & Kunkel) at 9500 rpm with intermittent cooling on ice for 30 seconds. The homogenate was centrifuged at 20.000×g for 30 minutes at 4° C., the supernatant was collected and stored at −20° C. until analysis for TNF-α small intestinal protein extractions were analyzed for TNF-α using a commercially available ELISA kit according to the manufacturer's instructions (Rat Tumor Necrosis Factor-α UltraSensitive ELISA kit, Biosource International Inc.). The assay has a detection limit of 0.7 pg/ml. Protein extractions were analyzed for total protein content using a commercially available assay (DC protein assay, Bio-Rad Laboratories Ltd.). Small intestinal tissue levels of TNF-α were expressed relative to total protein. Compound 1848 (SEQ ID NO:36) significantly decreased small intestinal tissue levels of the proinflammatory cytokine TNF-α and this effect was most marked in the proximal segment (first ⅓$^{rd}$ of small intestine). Compound 1848 (SEQ ID NO:36) was more efficacious than prednisolone in the proximal and mid segments (second ⅓$^{rd}$ of small intestine). Interestingly, compound 1848 (SEQ ID NO:36) suppressed inflammation in the small intestine more effectively than prednisone, and prednisone had no additive effect when given in combination with compound 1848 (SEQ ID NO:36). These results suggest that compound 1848 (SEQ ID NO:36) has a marked anti-inflammatory potential on diseases processes that affect the small intestine. Values are means±SEM. *P<0.05 vs. indomethacin (group 2).

DETAILED DESCRIPTION OF THE INVENTION

Definitions

Unless specified otherwise, the following definitions are provided for specific terms, which are used in the above written description.

Throughout the description and claims the conventional one-letter and three-letter codes for natural amino acids are used as well as generally accepted three letter codes for other α-amino acids, such as sarcosin (Sar), norleucine (Nle) and α-aminoisobutyric acid (Aib). All amino acid residues in peptides of the invention are preferably of the L-configuration, However, D-configuration amino acids may also be present.

Preferred compounds of the present invention have at least one GLP-2 biological activity, in particular in causing growth of the intestine. This can be assessed in in vivo assays, for example as described in the examples, in which the mass of the intestine, or a portion thereof is determined after a test animal has been treated or exposed to a GLP-2 analogue.

The GLP-2 analogues of the present invention have one or more amino acid substitutions, deletions, inversions, or additions compared with native GLP-2 and as defined above. This definition also includes the synonym terms GLP-2 mimetics and/or GLP-2 agonists. Further, the analogue of the present invention may additionally have chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine 1-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Preferably herein lower alkyl is $C_1$-$C_4$ alkyl. Furthermore, one or more side groups, or terminal groups, may be protected by protective groups known to the ordinarily-skilled peptide chemist. The α-carbon of an amino acid may be mono- or di-methylated.

Where they are present, oxidatively stable Met-replacement amino acid means one which is selected among the group consisting of Met(O) (methionine sulfoxide), Met(O)$_2$ (methionine sulfone), Val, Ile, Asn, Glx (Glu or Gln), Tyr, Phe, Trp and preferably Leu, Nle, Ala, Ser, and Gly.

By a peptide with "enhanced stability" is meant a peptide (e.g., a GLP-2 peptide described herein) having a increased resistance to degradation (e.g., at least 5%, 10%, 25%, 50%, 60%, 70%, 80%, 90%, 95%, or 99%) less as compared a reference peptide (e.g., Gly2-GLP-2 (SEQ ID NO:54)) under a given set of conditions over a given time period (e.g., at least 1, 6, or 12, or 1, 2, 3, 5, 6, 8, 10, 12, 15, 20, 30, 45, or 60 days). Alternatively or additionally, stability may be assayed by comparing the percent purity in a sample subjected to a set of conditions a compared to the same sample not subjected to the set of conditions. Any conditions described herein or known in the art may be used to test enhanced stability. In particular embodiments, stability is tested under acidic conditions (e.g., at least 0.01, 0.1, 0.2, 0.4, 0.5, 1.0, 2.0, or 5.0 M HCl), basic conditions (e.g., at least 0.01, 0.1, 0.2, 0.4, 0.5M 1.0, 2.0, or 5.0 M NaOH), oxidative stress (e.g., at least 0.01% 0.05%, 0.1%, 0.2%, 0.5%, 1.0%, 1.5%, 2.0%, 5%, or 10%, 20%, or 30% $H_2O_2$), or deamindation conditions (e.g., at least 0.01, 0.1, 0.2, 0.4, 0.5, 1.0, 2.0, or 5.0 M $NH_4HCO_3$). Conditions also include (either alone or incombination with the conditions listed increased temperature (e.g., at 30, 35, 37, 40, 45, 50, 60, 70, 80, 100, 150° C.). Exemplary conditions are described in Table 9 below.

It should be understood that the peptides of the invention might also be provided in the form of a salt or other derivative. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

Other derivatives of the GLP-2 analogues of the invention include coordination complexes with metal ions such as $Mn^{2+}$ and $Zn^{2+}$, esters such as in vivo hydrolysable esters, free acids or bases, hydrates, prodrugs or lipids. Esters can be formed between hydroxyl or carboxylic acid groups present in the compound and an appropriate carboxylic acid or alcohol reaction partner, using techniques well known in the art. Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. Examples of prodrugs include the use of protecting groups which may be removed in situ releasing active compound or serve to inhibit clearance of the drug in vivo.

When present, $Z^1$ and $Z^2$ each independently represent a peptide sequence of 3-20 or 4-20 amino acid residues, e.g. in the range of 4-15, more preferably in the range of 4-10 in particular in the range of 4-7 amino acid residues, e.g., of 4, 5, 6 or 7 amino acid residues, such as 6 amino acid residues. Each of the amino acid residues in the peptide sequences Z may independently be selected from Ala, Leu, Ser, Thr, Tyr, Asn, Gln, Asp, Glu, Lys, Arg, His, Met, Orn. Preferably, the amino acid residues are selected from Ser, Thr, Tyr, Asn, Gln, Asp, Glu, Lys, Arg, His, Orn, and Met, as well as amino acids falling within formula I as defined in WO01/04156, e.g., Dbu (2,4 diaminobutyric acid) or Dpr (2,3-diaminopropanoic acid), more preferably from Glu, Lys, and Met, especially Lys. The above-mentioned amino acids may have either D- or L-configuration, but preferably the above-mentioned amino acids have an L-configuration. Particularly preferred sequences Z are sequences of four, five or six consecutive lysine residues, and particularly six consecutive lysine residues. Exemplary sequences Z are shown in WO 01/04156.

In certain embodiments, $Z^1$ is absent. In such cases, $Z^2$ may be either present or absent.

The present invention includes the following peptides further described in the experimental section below.

```
Reference GLP-2 analogue
1559 H-[Gly2]hGLP-2-OH
```

```
                             -continued
H-HGDGSFSDEMNTILDNLAARDFINWLIQTKITD-   (SEQ ID NO:54)
OH Examples of GLP-2 analogues of the
present invention
1809 [Gly2, Glu3, Thr5, Leu10,
Ala11, 16, 24, 28]hGLP-2-(Lys)6-NH2
HGEGTFSDELATILDALAARDFIAWLIATKITDK6-   (SEQ ID NO:1)
NH2

1810 [Gly2, Glu3, Thr5, Leu10,
Ala11, 16, 24, 28, Ile21]hGLP-2
(1-30)-(Lys)6-NH2
HGEGTFSDELATILDALAARIFIAWLIATK6-NH2    (SEQ ID NO:2)

1811 [Gly2, Pro6, Leu10, Ala11, 16,
24, 28]hGLP-2-NH2
HGDGSPSDELATILDALAARDFIAWLIATKITD-     (SEQ ID NO:3)
NH2

1812 [Gly2, Glu3, Leu10, Ala11, 24]
hGLP-2-NH2
HGEGSFSDELATILDNLAARDFIAWLIQTKITD-     (SEQ ID NO:4)
NH2

1813 [Gly2, Leu10, Ala11, 16, 24,
28]hGLP-2-NH2
H-HGDGSFSDELATILDALAARDFIAWLIATKITD-   (SEQ ID NO:5)
NH2

1814 [Gly2, Leu10, Ala11, 24, 28]
hGLP-2-NH2
H-HGDGSFSDELATILDNLAARDFIAWLIATKITD-   (SEQ ID NO:6)
NH2

1815 [Gly2, Glu3, Leu10, Ala11, 16,
24, 28]hGLP-2-NH2
H-HGEGSFSDELATILDALAARDFIAWLIATKITD-   (SEQ ID NO:7)
NH2

1818 [Gly2, Ser8, Leu10, Ala11, 24]
hGLP-2(1-30)-K6-NH2
H-HGDGSFSSELATILDNLAARDFIAWLIQTK6-     (SEQ ID NO:8)
NH2

1819 [Gly2, Leu10, Ser11, Ala24]
hGLP-2(1-30)-K6-NH2
H-HGDGSFSDELSTILDNLAARDFIAWLIQTK6-     (SEQ ID NO:9)
NH2

1820 [Gly2, Thr7, Ser8, Leu10,
Ala11, 24]hGLP-2(1-30)-K6-NH2
H-HGDGSFTSELATILDNLAARDFIAWLIQTK6-     (SEQ ID NO:10)
NH2

1821 [Gly2, Leu10, Lys11, Ala24]
hGLP-2(1-30)-K6-NH2
H-HGDGSFSDELKTILDNLAARDFIAWLIQTK6-     (SEQ ID NO:11)
NH2

1822 [Gly2, Thr7, Leu10, Lys11,
Ala24]hGLP-2(1-30)-K6-NH2
H-HGDGSFTDELKTILDNLAARDFIAWLIQTK6-     (SEQ ID NO:12)
NH2

1823 [Gly2, Thr7, Ser8, Leu10,
Lys11, Ala24]hGLP-2(1-30)-K6-NH2
H-HGDGSFTSELKTILDNLAARDFIAWLIQTK6-     (SEQ ID NO:13)
NH2

1824 [Gly2, Thr7, Leu10, Ala11, 24]
hGLP-2(1-30)-K6-NH2
H-HGDGSFTDELATILDNLAARDFIAWLIQTK6-     (SEQ ID NO:14)
NH2

1825 [Gly2, Ser8, Leu10, Ala11,
24]hGLP-2(1-30)-NH2
H-HGDGSFSSELATILDNLAARDFIAWLIQTK-NH2   (SEQ ID NO:15)

1826 [Gly2, Leu10, Ala24]hGLP-2-K6-
```

-continued

1826 [Gly2, Leu10, Ala11, 24]hGLP-2(1-30)-K₆-NH₂
H-HGDGSFSDELNTILDNLAARDFIAWLIQTKITD (SEQ ID NO:16)
K₆-NH₂

1827 [Gly2, Thr7, Leu10, Ser11, Ala24]hGLP-2(1-30)-K₆-NH₂
H-HGDGSFTDELSTILDNLAARDFIAWLIQTK₆- (SEQ ID NO:17)
NH₂

1828 [Gly2, Thr7, Leu10, Ser8, 11, Ala24]hGLP-2(1-30)-K₆-NH₂
H-HGDGSFTSELSTILDNLAARDFIAWLIQTK₆- (SEQ ID NO:18)
NH₂

1829 [Gly2, Leu10, Ser8, 11, Ala24]hGLP-2(1-30)-K₆-NH₂
H-HGDGSFSSELSTILDNLAARDFIAWLIQTK₆- (SEQ ID NO:19)
NH₂

1830 [Gly2, Leu10, Ser11, Ala24]hGLP-2(1-30)-NH₂
H-HGDGSFSDELSTILDNLAARDFIAWLIQTK-NH₂ (SEQ ID NO:20)

1831 [Gly2, Thr7, Leu10, Ser11, Ala24]hGLP-2(1-30)-NH₂
H-HGDGSFTDELSTILDNLAARDFIAWLIQTK-NH₂ (SEQ ID NO:21)

1832 [Gly2, Thr7, Leu10, Ser8, 11, Ala24]hGLP-2(1-30)-NH₂
H-HGDGSFTSELSTILDNLAARDFIAWLIQTK-NH₂ (SEQ ID NO:22)

1833 [Gly2, Leu10, Ser8, 11, Ala24]hGLP-2(1-30)-NH₂
H-HGDGSFSSELSTILDNLAARDFIAWLIQTK-NH₂ (SEQ ID NO:23)

1834 [Gly2, Thr7, Ser8, Leu10, Ala11, 24]hGLP-2(1-30)-NH₂
H-HGDGSFTSELATILDNLAARDFIAWLIQTK-NH₂ (SEQ ID NO:24)

1835 [Gly2, Leu10, Lys11, Ala24]hGLP-2(1-30)-NH₂
H-HGDGSFSDELKTILDNLAARDFIAWLIQTK-NH₂ (SEQ ID NO:25)

1836 [Gly2, Thr7, Leu10, Lys11, Ala24]hGLP-2(1-30)-NH₂
H-HGDGSFTDELKTILDNLAARDFIAWLIQTK-NH₂ (SEQ ID NO:26)

1839 [Leu10, Ala11, Ala24]hGLP-2(1-33)-K₆-NH₂
H-HGDGSFSDELATILDNLAARDFIAWLIQTKITD (SEQ ID NO:27)
K₆-NH₂

1840 [Leu10, Ala11, Ala24]hGLP-2(1-33)-NH₂
H-HGDGSFSDELATILDNLAARDFIAWLIQTKITD- (SEQ ID NO:28)
NH₂

1841 [Leu10, Ala11, Ala24]hGLP-2(1-30)-NH₂
H-HGDGSFSDELATILDNLAARDFIAWLIQTK-NH₂ (SEQ ID NO:29)

1842 [Thr7, Ser8, Leu10, Lys11, Ala24]hGLP-2(1-30)-NH₂
H-HGDGSFTSELKTILDNLAARDFIAWLIQTK-NH₂ (SEQ ID NO:30)

1843 [Thr7, Leu10, Ala11, Ala24]hGLP-2(1-30)-NH₂
H-HGDGSFTDELATILDNLAARDFIAWLIQTK-NH₂ (SEQ ID NO:31)

1844 [Gly2, Glu3, Thr5, Ser8, 11, Leu10, Ala16, 24]hGLP-2(1-33)-(Lys)₆-NH₂
H-HGEGTFSSELSTILDALAARDFIAWLIATKITD (SEQ ID NO:32)
K₆-NH₂

1845 [Gly2, Glu3, Thr5, Leu10, Ser11, Ala16, 24, 28]hGLP-2(1-33)-(Lys)₆-NH₂
H-HGEGTFSDELSTILDALAARDFIAWLIATKITD (SEQ ID NO:33)
K₆-NH₂

1846 [Gly2, Glu3, Ser8, 11, Leu10, Ala16, 24, 28]hGLP-2(1-33)-(Lys)₆-NH₂
H-HGEGSFSSELSTILDALAARDFIAWLIATKITD (SEQ ID NO:34)
K₆NH₂

1847 [Gly2, Glu3, Leu10, Ser11, Ala16, 24, 28]hGLP-2(1-33)-(Lys)₆-NH₂
H-HGEGSFSDELSTILDALAARDFIAWLIATKITD (SEQ ID NO:35)
K₆-NH₂

1848 [Gly2, Glu3, Thr5, Ser8, Leu10, Ala11, 16, 24, 28]hGLP-2(1-33)-(Lys)₆-NH₂
H-HGEGTFSSELATILDALAARDFIAWLIATKITD (SEQ ID NO:36)
K₆-NH₂

1849 [Gly2, Glu3, Ser8, Leu10, Ala11, 16, 24, 28]hGLP-2(1-33)-(Lys)₆-NH₂
H-HGEGSFSSELATILDALAARDFIAWLIATKITD (SEQ ID NO:37)
K₆-NH₂

1850 [Gly2, Glu3, Leu10, Lys11, Ala16, 24, 28]hGLP-2(1-33)-(Lys)₆-NH₂
H-HGEGSFSDELKTILDALAARDFIAWLIATKITD (SEQ ID NO:38)
K₆-NH₂

1851 [Gly2, Glu3, Thr5, Leu10, Lys11, Ala16, 24, 28]hGLP-2(1-33)-(Lys)₆-NH₂
H-HGEGTFSDELKTILDALAARDFIAWLIATKITD (SEQ ID NO:39)
K₆-NH₂

1852 [Gly2, Glu3, Thr5, Ser8, Leu10, Lys11, Ala16, 24, 28]hGLP-2(1-33)-NH₂
H-HGEGTFSSELKTILDALAARDFIAWLIATKITD (SEQ ID NO:40)
K₆-NH₂

1853 [Gly2, Glu3, Thr5, Ser8, 11, Leu10, Ala16, 24, 28]hGLP-2(1-33)-NH₂
H-HGEGTFSSELSTILDALAARDFIAWLIATKITD- (SEQ ID NO:41)
NH₂

1854 [Gly2, Glu3, Thr5, Leu10, Ser11, Ala16, 24, 28]hGLP-2(1-33)-NH₂
H-HGEGTFSDELSTILDALAARDFIAWLIATKITD- (SEQ ID NO:42)
NH₂

1855 [Gly2, Glu3, Thr5, Ser8, Leu10, Ala11, 16, 24, 28]hGLP-2(1-33)-NH₂
H-HGEGTFSSELATILDALAARDFIAWLIATKITD- (SEQ ID NO:43)
NH₂

1856 [Gly2, Glu3, Ser8, 11, Leu10, Ala16, 24, 28]hGLP-2(1-33)-NH₂
H-HGEGSFSDELSTILDALAARDFIAWLIATKITD- (SEQ ID NO:44)
NH₂

1857 [Gly2, Glu3, Leu10, Ser11, Ala16, 24, 28]hGLP-2(1-33)-NH₂
H-HGEGTFSSELATILDALAARDFIAWLIATKITD- (SEQ ID NO:45)
NH₂

1858 (Gly2, Glu3, Ser8, Leu10, Ala11, 16, 24, 28]hGLP-2(1-33)-NH₂
H-HGEGSFSSELATILDALAARDFIAWLIATKITD- (SEQ ID NO:46)
NH₂

1859 [Gly2, Glu3, Leu10, Lys11, Ala16, 24, 28]hGLP-2(1-33)-NH₂
H-HGEGSFSDELKTILDALAARDFIAWLIATKITD- (SEQ ID NO:47)
NH₂

```
-continued
1860 [Gly2, Glu3, Thr5, Leu10,
Lys11, Ala16, 24, 28]hGLP-2(1-33)-
NH2
H-HGEGTFSDELKTILDALAARDFIAWLIATKITD-    (SEQ ID NO:48)
NH2

1861 (Gly2, Glu3, Thr5, Ser8, Leu10,
Lys11, Ala16, 24, 28]hGLP-2(1-33)-
NH2
HGEGTFSSELKTILDALAARDFIAWLIATKITD       (SEQ ID NO:49)
```

Particularly preferred compounds of the present invention include compounds 1834 (SEQ ID NO:24), 1846 (SEQ ID NO:34), 1847 (SEQ ID NO:35), 1848 (SEQ ID NO:36), 1849 (SEQ ID NO:37), 1855 (SEQ ID NO:43), 1857 (SEQ ID NO:45), and 1858 (SEQ ID NO:46).

```
1834 H-HGDGSFTSELATILDNLAARDFIAWLIQTK-NH2        (SEQ ID NO:24)

1846 H-HGEGSFSSELSTILDALAARDFIAWLIATKITDK6NH2    (SEQ ID NO:34)

1847 H-HGEGSFSDELSTILDALAARDFIAWLIATKITDK6-NH2   (SEQ ID NO:35)

1848 H-HGEGTFSSELATILDALAARDFIAWLIATKITDK6-NH2   (SEQ ID NO:36)

1849 H-HGEGSFSSELATILDALAARDFIAWLIATKITDK6-NH2   (SEQ ID NO:37)

1855 H-HGEGSFSSELSTILDALAARDFIAWLIATKITD-NH2     (SEQ ID NO:43)

1857 H-HGEGTFSSELATILDALAARDFIAWLIATKITD-NH2     (SEQ ID NO:45)

1858 H-HGEGSFSSELATILDALAARDFIAWLIATKITD-NH2     (SEQ ID NO:46)
```

Stability Studies

The skilled person will be able to design appropriate methods (e.g. quantitative methods) for detection of degradation products of GLP-2 analogues, e.g. based on those described below. Degradation may occur as oxidation, hydrolysis and deamidation, depending on the identity and position of the amino acids in any given GLP-2 analogue, and conditions as pH, solution and temperature. The compounds can be ranked according to chemical stability, when the compounds are incubated under stressed conditions (i.e. conditions likely to cause degradation) and subsequently analysed for content of remaining intact peptide. In addition, the knowledge gained about major degradation products obtained under stressed conditions will be important for any later analytical method development.

Quantitative Assays to Detect GLP Analogues

The skilled person will also be capable of designing methods (e.g. quantitative methods) for detection of GLP analogues in complex environments or solutions (e.g. plasma, urine, tissue homogenates, cell homogenates, saliva or similar) to investigate the absorption, distribution, metabolism and excretion of the GLP analogues after administration to mammals or as part of functional studies of in vitro cell systems.

In one embodiment, a quantitative assay can be based on antibodies raised against the GLP analogues or fragments thereof. The antibodies obtained from the immunized animals can be used for quantitative assays. In one example a direct sandwich ELISA can be prepared using a first antibody with affinity of one part of the molecule immobilized in a multi-well plate. The sample is then applied to the wells and the GLP analogue is captured by the first antibody. The captured GLP analogue is then recognized by a second antibody with affinity for another part of the GLP analogue. The second antibody can be labeled with an enzyme (horseradish peroxidase, alkaline phosphatase or beta-galactosidase) or a radioisotope. The amount of captured GLP analogue can then be detected by addition of a colorimetric substrate or direct counting of radio-emission or by scintillation. Alternatively, the amount of captured GLP analogue can be detected indirectly by addition of a labeled antibody with affinity for the second antibody. The concentration in the sample can be estimated from the response obtained from an external standard curve containing known amounts of GLP analogue. Alternatively, the antibodies can be used to prepare a direct competitive immuno assay, where an antibody specific for the GLP analogue is immobilized on a multi-well plate and the sample incubated in the wells with a predefined fixed concentration of labeled GLP analogue. The label can be an enzyme, a fluorophore, a radioisotope or biotin and detected using, for example, substrates (e.g. colorimetric, fluorometric or chemiluminescent) specific for the enzymes, scintillation or avidin linked to an enzyme followed by detection as described above. The amount of bound labeled GLP analogue can be detected by an appropriate method and the concentration of GLP analogue present in the sample derived from the response obtained from an external standard curve as described above.

In another embodiment, a quantitative assay can be based on liquid chromatography tandem mass spectroscopy methodology. In such a set up, the response from a fragment specific for the GLP analogue to be studied is monitored upon fragmentation of the parent compound induced by collision with an inert gas (He or Ar). Prior to fragmentation the sample components can be separated by reversed phase chromatography or the sample can be injected directly in the mass spectrometer. If suitable the sample can be subjected to pre-treatment (i.e., addition of protease inhibitors, protein precipitation, solid phase extraction, immuno-affinity extraction, etc. The concentration of GLP analogue present in the sample derived from the response obtained from an external standard curve as described above, potentially after correction of the response using an internal standard similar to the GLP analogue to be studied.

Generation of Specific Antibodies

Specific antibodies against the GLP analogues or fragments thereof can be induced in mammals and purified from the serum. The GLP analogues or fragments can either be used directly with an adjuvant to immunize rabbits, mice or other mammals, or the GLP analogues or fragments thereof can be chemically linked to a carrier molecule (i.e., keyhole limpet hemocyanin, ovalbumin, albumin etc.) and injected with an adjuvant. The injections can be repeated with 2-4 weeks intervals for extended periods to improve the affinity and selectivity of the antibodies. Polyclonal antibodies can be harvested directly from the serum. To obtain monoclonal antibodies, B cells isolated from immunized animals, preferably mice, should be fused with tumor cells to form antibody producing hybridomas. Screening and selection of the appropriate clones and antibodies can be performed using either immobilized GLP analogues or peptides thereof followed by detection with labeled anti-antibodies. Alternatively the screening and selection could be based on immobilized antibodies followed by detection with labeled GLP analogues or fragments thereof. In all cases, the label could be a radioisotope, an enzyme, a fluorophore or biotin and detected using, for example, substrates (e.g. colorimetric, fluorometric or chemiluminiscent) specific for the enzymes, scintillation or avidin linked to an enzyme followed by detection as described.

Synthesis of GLP-2 Analogues

It is preferred to synthesize the analogues of the invention by means of solid phase or liquid phase peptide synthesis. In this context, reference is given to WO 98/11125 and, amongst many others, Fields, G B et al., 2002, "Principles and practice of solid-phase peptide synthesis". In: Synthetic Peptides (2nd Edition) and the Examples herein.

Thus the GLP-2 analogues may be synthesized in a number of ways including for example, a method which comprises:

(a) synthesizing the peptide by means of solid phase or liquid phase peptide synthesis and recovering the synthetic peptide thus obtained; or (b) when the peptide is constituted by naturally occurring amino acids, expressing a nucleic acid construct that encodes the peptide in a host cell and recovering the expression product from the host cell culture; or (c) when the peptide is constituted by naturally occurring amino acids, effecting cell-free in vitro expression of a nucleic acid construct that encodes the peptide and recovering the expression product; or a combination of methods of (a), (b), and (c) to obtain fragments of the peptide, subsequently ligating the fragments to obtain the peptide, and recovering the peptide.

Thus, for some analogues of the invention it may be advantageous to exploit genetic engineering techniques. This may be the case when the peptide is sufficiently large (or produced as a fusion construct) and when the peptide only includes naturally occurring amino acids that can be translated from RNA in living organisms.

For the purpose of recombinant gene technology nucleic acid fragments encoding the peptides of the invention are important chemical products. Hence, a further aspect of the present invention provides a nucleic acid molecule comprising a nucleic acid sequence encoding a GLP-2 analogue of the invention, where the peptide preferably is comprised by naturally occurring amino acids. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) of the invention are capable of autonomous replication, thereby enabling high copy-numbers for the purposes of high-level expression or high-level replication for subsequent cloning.

The general outline of a vector of the invention comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma) of or a leader peptide for multiple use e.g. combined secretion, purification tag and enzymatic trimming to correct peptide or integration into the membrane of the polypeptide fragment, the nucleic acid fragment encoding the peptide of the invention, and optionally a nucleic acid sequence encoding a terminator. When operating with expression vectors in producer strains or cell-lines it is for the purposes of genetic stability of the transformed cell preferred that the vector when introduced into a host cell is integrated in the host cell genome.

The vectors of the invention are used to transform host cells to produce the modified peptide of the invention. Such transformed cells, which are also part of the invention, can be cultured cells or cell lines used for propagation of the nucleic acid fragments and vectors of the invention, or used for recombinant production of the peptides of the invention.

Preferred transformed cells of the invention are microorganisms such as bacteria (such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (such as *Saccharomyces cerevisiae*), and protozoans. Alternatively, the transformed cells are derived from a multicellular organism, i.e. it may be fungal cell, an insect cell, a plant cell, or a mammalian cell. Also cells derived from a human being are interesting, cf. the discussion of cell lines and vectors below. For the purposes of cloning and/or optimised expression it is preferred that the transformed cell is capable of replicating the nucleic acid fragment of the invention. Cells expressing the nucleic fragment are preferred useful embodiments of the invention; they can be used for small-scale or large-scale preparation of the peptides of the invention.

When producing the peptide of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment encoding the peptide. Preferably, this stable cell line secretes or carries the peptide of the invention, thereby facilitating purification thereof.

In general, plasmid vectors containing replicon and control sequences, which are derived from species compatible with the host cell, are used in connection with the hosts. The vector ordinarily carries a replication site, as well as marking sequences, which are capable of providing phenotypic selection in transformed cells. For example, *E. coli* is typically transformed using pBR322 (but numerous other useful plasmids exist) a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain promoters, which can be used by the prokaryotic microorganism for expression.

Those promoters most commonly used in prokaryotic recombinant DNA construction include the β-lactamase (penicillinase) and lactose promoter systems (Chang et al., 1978; Itakura et al., 1977; Goeddel et al., 1979) and a tryptophan (trp) promoter system (Goeddel et al., 1979; EP 0 036 776 A). While these are the most commonly used, other microbial promoters have been discovered and utilized, and details concerning their nucleotide sequences have been published, enabling a skilled worker to ligate them functionally with plasmid vectors (Siebwenlist et al., 1980).

In addition to prokaryotes, eukaryotic microbes, such as yeast cultures may also be used, and also here the promoter should be capable of driving expression. *Saccharomyces cerevisiae*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Spodoptera frugiperda* (SF) cells (commercially available as complete expression systems from i.a. Protein Sciences, 1000 Research Parkway, Meriden, Conn. 06450, U.S.A. and from Invitrogen), the *D. melanogaster* cell line $S_2$ available from Invitrogen, PO Box 2312, 9704 CH Groningen, The Netherlands, and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment, which also contains the SV40 viral origin of replication (Fiers et al., 1978). Smaller or larger SV40 fragments may also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV) or may be provided by the host cell chromosomal replication mechanism. If the vector is integrated into the host cell chromosome, the latter is often sufficient.

In order to obtain satisfactory yields in a recombinant production process, it may be advantageous to prepare the analogues as fusion proteins, either by fusing the peptide to a fusion partner that can serve as an affinity tag (for ease of purification) and/or by having multiple repeats of the peptide. These methods require presence of a suitable cleavage site for a peptidase, but the skilled person will know how to tailor the underlying genetic constructs.

After recombinant preparation, the peptides of the invention can be purified by methods generally known in the art, including multi-step chromatography (e.g., ion-exchange, size-exclusion, and affinity chromatographic techniques).

Alternatively, peptides comprised of naturally occurring amino acids can be prepared in vitro in cell free systems. This is especially expedient in cases where the peptides could be toxic for putative host cells. Thus, the present invention also contemplates use of cell-free in vitro translation/expression in order to prepare the peptides of the invention. In this context, reference is made to commercially available in vitro translation kits, materials, and technical documentation from e.g., Ambion Inc., 2130 Woodward, Austin, Tex. 78744-1832, USA.

Finally, the available methods can of course be combined so as to prepare e.g. semi-synthetic analogues. In such a set up, peptide fragments are prepared using at least 2 separate steps or methods, followed by ligation of the fragments to obtain the final peptide product.

Pharmaceutical Compositions and Administration

The GLP-2 analogues of the present invention, or salts or derivatives thereof, may be formulated as pharmaceutical compositions prepared for storage or administration, and which comprise a therapeutically effective amount of a GLP-2 peptide of the present invention, or a salt or derivative thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy so as to deliver the peptide to the large intestine, but will depend on such factors as weight, diet, concurrent medication and other factors, well known those skilled in the medical arts.

It is within the invention to provide a pharmaceutical composition, wherein the GLP-2 analogue, or a salt thereof is present in an amount effective to treat or prevent stomach and bowel-related disorders.

Pharmaceutically acceptable salts of the compounds of the invention having an acidic moiety can be formed using organic and inorganic bases. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di- or trihydroxy lower alkylamine (e.g., mono-, di- or triethanolamine). Internal salts also may be formed. Similarly, when a compound of the present invention contains a basic moiety, salts can be formed using organic and inorganic acids. For example, salts can be formed from the following acids: acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, and camphorsulfonic as well as other known pharmaceutically acceptable acids. Amino acid addition salts can also be formed with amino acids such as lysine, glycine, or phenylalanine.

As is apparent to one skilled in the medical art, a "therapeutically effective amount" of the peptides or pharmaceutical compositions of the present invention will vary depending upon the age, weight and mammalian species treated, the particular compounds employed, the particular mode of administration and the desired effects and the therapeutic indication. Because these factors and their relationship to determining this amount are well known in the medical arts, the determination of therapeutically effective dosage levels, the amount necessary to achieve the desired result of preventing and/or treating the intestine and stomach related diseases described herein, as well as other medical indications disclosed herein, will be within the ambit of the skilled person.

As used herein, "a therapeutically effective amount" is one which reduces symptoms of a given condition or pathology, and preferably which normalizes physiological responses in an individual with the condition or pathology. Reduction of symptoms or normalization of physiological responses can be determined using methods routine in the art and may vary with a given condition or pathology. In one aspect, a therapeutically effective amount of one or more GLP-2 analogues or pharmaceutical composition comprising the one or more GLP-2 analogues is an amount which restores a measurable physiological parameter to substantially the same value (preferably to within +30%, more preferably to within +20%, and still more preferably, to within 10% of the value) of the parameter in an individual without the condition or pathology.

In one embodiment of the invention administration of the compounds or pharmaceutical composition of the present invention is commenced at lower dosage levels, with dosage levels being increased until the desired effect of preventing/treating the relevant medical indication, such as intestine and stomach related diseases is achieved. This would define a therapeutically effective amount. For the peptides of the present invention, alone or as part of a pharmaceutical composition, such doses may be between about 0.01 mg/kg and 100 mg/kg body weight, such as between about 0.01 mg/kg and 10 mg/kg body weight, for example between 10-100 μg/kg body weight.

For therapeutic use, the chosen GLP-2 analogue is formulated with a carrier that is pharmaceutically acceptable and is appropriate for delivering the peptide by the chosen route of administration. For the purpose of the present invention, peripheral parenteral routes include intravenous, intramuscular, subcutaneous, and intra peritoneal routes of administration. Certain compounds used in the present invention may also be amenable to administration by the oral, rectal, nasal, or lower respiratory routes. These are so-called non-parenteral routes. The present pharmaceutical composition comprises a GLP-2 analogue of the invention, or a salt or derivative thereof and a pharmaceutically acceptable carrier. Suitable pharmaceutically acceptable carriers are those used conventionally with peptide-based drugs, such as diluents, excipients and the like. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris(hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. Preferred buffer ranges are pH 4-8, pH 6.5-8, more preferably pH 7-7.5. Preservatives, such as para, meta, and ortho-cresol, methyl- and propylparaben, phenol, benzyl alcohol, sodium benzoate, benzoic acid, benzyl-benzoate, sorbic acid, propanoic acid, esters of p-hydroxybenzoic acid may be provided in the pharmaceutical composition. Stabilizers, preventing oxidation, deamidation, isomerisation, racemisation, cyclisation, peptide hydrolysis, such as e.g. ascorbic acid, methionine, tryptophane, EDTA, asparagine, lysine, arginine, glutamine and glycine may be provided in the pharmaceutical composition. Stabilizers, preventing aggregation, fibrillation and precipitation, such as Sodium dodecyl sulphate, polyethylene glycol, carboxymethyl cellulose, cyclodextrine may be provided in the pharmaceutical composition. Organic modifiers for solubilization or preventing aggregation, such as ethanol, acetic acid or acetate and salts thereof may be provided in the pharmaceutical composition. Isotonicity makers such as salts e.g. sodium chloride or most preferred carbohydrates e.g. dextrose, mannitol, lactose, trehalose, sucrose or mixtures thereof may be provided in the pharmaceutical composition.

Detergents, such as Tween 20, Tween 80, SDS, Poloxamers e.g. Pluronic F-68, Pluronic F-127, may be provided in the pharmaceutical composition. Dyes and even flavoring agents may be provided in the pharmaceutical composition. In another embodiment, a pharmaceutically acceptable acid addition salt of the GLP-2 peptide analogue is provided for. Suspending agents may be used.

Organic modifiers, such as ethanol, tertiary-buthanol, 2-propanol, ethanol, glycerol, Polyethylene glycol may be provided in the pharmaceutical formulation for lyophilization of a lyophilized product. Bulking agents and isotonicity makers such as salt e.g. sodium chloride, carbohydrates e.g. dextrose, mannitol, lactose, trehalose, sucrose or mixtures thereof, aminoacids e.g. glycine, glutamate, or excipients such as cystein, lecithin or human serum albumin, or mixtures thereof may be provided in the pharmaceutical composition for lyophilization.

The pharmaceutical compositions of the present invention may be formulated and used as tablets, capsules or elixirs for oral administration; suppositories for rectal administration; preferably sterile solutions or sterile powder or suspensions for injectable administration; and the like. The dose and method of administration can be tailored to achieve optimal efficacy but will depend on such factors as weight, diet, concurrent medication and other factors, which those skilled in the medical arts will recognize.

When administration is to be parenteral, such as intravenous and subcutaneous, e.g., on a daily basis, injectable pharmaceutical compositions can be prepared in conventional forms, either as aqueous solutions or suspensions; lyophilized, solid forms suitable for reconstitution immediately before use or suspension in liquid prior to injection, or as emulsions.

Diluents for reconstitution of the lyophilized product may be a suitable buffer from the list above, water, saline, dextrose, mannitol, lactose, trehalose, sucrose, lecithin, albumin, sodium glutamate, cysteine hydrochloride; or water for injection with addition of detergents, such as Tween 20, Tween 80, poloxamers e.g. pluronic F-68 or pluronic F-127, polyethylene glycol, and or with addition of preservatives such as para-, meta-, and ortho-cresol, methyl- and propylparaben, phenol, benzyl alcohol, sodium benzoate, benzoic acid, benzyl-benzoate, sorbic acid, propanoic acid, esters of p-hydroxybenzoic acid, and or with addition of an organic modifier such as ethanol, acitic acid, citric acid, lactic acid or salts thereof.

In addition, if desired, the injectable pharmaceutical compositions may contain minor amounts of non-toxic auxiliary substances, such as wetting agents, or pH buffering agents. Absorption enhancing preparations (e.g., liposomes, detergents and organic acids) may be utilized.

In one embodiment of the invention, the compounds are formulated for administration by infusion, e.g., when used as liquid nutritional supplements for patients on total parenteral nutrition therapy (for example neonatals, or patients suffering from cachexia or anorexia), or by injection, for example subcutaneously, intraperitoneal or intravenously, and are accordingly utilized as aqueous solutions in sterile and pyrogen-free form and optionally buffered to physiologically tolerable pH, e.g., a slightly acidic or physiological pH. Formulation for intramuscular administration may be based on solutions or suspensions in plant oil, e.g. canola oil, corn oil or soy bean oil. These oil based formulations may be stabilized by antioxidants e.g. BHA (butylated hydroxianisole) and BHT (butylated hydroxytoluene).

Thus, the present peptide compounds may be administered in a vehicle, such as distilled water or in saline, phosphate buffered saline, 5% dextrose solutions or oils. The solubility of the GLP-2 analogue may be enhanced, if desired, by incorporating a solubility enhancer, such as detergents and emulsifiers.

The aqueous carrier or vehicle can be supplemented for use as injectables with an amount of gelatin that serves to depot the GLP-2 analogue at or near the site of injection, for its slow release to the desired site of action. Alternative gelling agents, such as hyaluronic acid, may also be useful as depot agents.

In one embodiment of the present invention the formulation comprises a. L-histidine dissolved in water to obtain final concentrations of from 0.5 mM to 300 mM, preferably from 3 to 200 mM, most preferably from 20 to 100 mM;

b. mannitol to obtain up to 350 mM, preferably from 30 to 300 mM, most preferably from 100 mM to 230 mM; and c. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In another embodiment of the present invention the formulation comprises a. L-histidine dissolved in water to obtain final concentrations of from 0.5 mM to 300 mM, preferably from 3 to 200 mM, most preferably from 20 to 100 mM L-histidine;

b. L-Arginine to obtain up to 200 mM, preferably from 0.5 to 100 mM, most preferably from 5 to 50 mM;

c. mannitol to obtain up to 350 mM, preferably from 30 to 300 mM, most preferably from 100 mM to 230 mM; and d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In still another embodiment of the present invention the formulation comprises a. L-histidine dissolved in water to obtain final concentrations of up to 200 mM, preferably from 3 to 100 mM, most preferably from 5 to 50 mM L-histidine;

b. L-Arginine to obtain up to 200 mM, preferably from 0.5 to 100 mM, most preferably from 5 to 50 mM;

c. mannitol to obtain up to 350 mM, preferably from 30 to 300 mM, most preferably from 100 mM to 230 mM; and d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In yet another embodiment of the present invention the formulation comprises a. L-histidine dissolved in water to obtain final concentrations of from 0.5 to 300 mM, preferably from 3 to 200 mM, most preferably from 20 to 100 mM L-histidine;

b. L-Arginine to obtain up to 200 mM, preferably from 0.5 to 100 mM, most preferably from 5 to 50 mM;

c. mannitol to obtain up to 350 mM, preferably from 30 to 300 mM, most preferably from 100 mM to 230 mM; and d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL. pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In yet another embodiment of the present invention the formulation comprises
a. L-histidine dissolved in water to obtain final concentrations of from up to 200 mM, preferably from 3 to 100 mM, most preferably from 5 to 50 mM L-histidine;
b. L-Arginine to obtain up to 200 mM, preferably from 0.5 to 100 mM, most preferably from 5 to 50 mM;
c. mannitol to obtain up to 350 mM, preferably from 30 to 300 mM, most preferably from 100 mM to 230 mM; and
d. acetic acid to obtain up to 200 mM, preferably from 0.05 to 100 mM, most preferably from 0.5 to 50 mM into solution.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product.

In yet another embodiment of the present invention the formulation comprises
a. N-acetate dissolved in water to obtain final concentrations of from up to 200 mM, preferably from 0.5 to 100 mM, most preferably from 5 to 50 mM L-histidine;
b. mannitol to obtain up to 350 mM, preferably from 30 to 300 mM, most preferably from 100 mM to 230 mM.

Appropriate amount of therapeutic compound is added to obtain concentrations of from 1 to 100 mg/mL, preferably from 5 to 50 mg/mL, most preferably from 10 to 30 mg/mL.

pH are adjusted to final pH at from 4 to 8, preferably from 6.5 to 7.5, most preferably from 6.7 to 7.3. The resulting solution is adjusted to target weight, sterile filtered and dispensed into appropriate aliquots in vials for pharmaceutical use. The formulation is further processed according to a liquid product or to a lyophilised product The GLP-2 analogues of the invention may also be formulated as a slow release implantation device for extended and sustained administration of the GLP-2 peptide analogue. Such sustained release formulations may be in the form of a patch positioned externally on the body. Examples of sustained release formulations include composites of biocompatible polymers, such as poly(lactic acid), poly(lactic-co-glycolic acid), methylcellulose, hyaluronic acid, sialic acid, silicate, collagen, liposomes and the like. Sustained release formulations may be of particular interest when it is desirable to provide a high local concentration of a GLP-2 analogue of the invention.

The GLP-2 analogue may be utilized in the form of a sterile-filled vial or ampoule containing an intestinotrophic amount of the peptide, in either unit dose or multi-dose amounts. The vial or ampoule may contain the GLP-2 analogue and the desired carrier, as an administration ready formulation. Alternatively, the vial or ampoule may contain the GLP-2 peptide in a form, such as a lyophilized form, suitable for reconstitution in a suitable carrier, such as sterile water or phosphate-buffered saline.

As an alternative to injectable formulations, the GLP-2 analogue may be formulated for administration by other routes. Oral dosage forms, such as tablets, capsules and the like, can be formulated in accordance with standard pharmaceutical practice. According to the present invention, the GLP-2 analogue is administered to treat individuals that would benefit from growth of small bowel tissue.

Nasal dosage forms can be formulated with addition of enhancers, such as Chitosan or detergents such as Tween 20, Tween 80, Poloxamers, e.g., Pluronic F-68, Pluronic F-127; Brij 35, Brij 72, cremophor EL.

The peptide compounds of the present invention may be used alone, or in combination with compounds having an anti-inflammatory effect. Without being bound by theory, it is envisioned that such combination treatment may enforce the beneficial treatment effects of the present peptide analogues.

The therapeutic dosing and regimen most appropriate for patient treatment will of course vary with the disease or condition to be treated, and according to the patient's weight and other parameters. Without wishing to be bound by any particular theory, it is expected that doses, in the μg/kg range, and shorter or longer duration or frequency of treatment may produce therapeutically useful results, such as a statistically significant increase particularly in small bowel mass. In some instances, the therapeutic regimen may include the administration of maintenance doses appropriate for preventing tissue regression that occurs following cessation of initial treatment. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

A human dose of a GLP-2 peptide according to the invention may in one embodiment be from about 10 μg/kg body weight/day to about 10 mg/kg/day, preferably from about 50 μg/kg/day to about 5 mg/kg/day, and most preferably about 100 μg/kg/day to 1 mg/kg/day.

Medical Conditions

The peptides of the present invention are useful as a pharmaceutical agent for preventing or treating an individual suffering from gastro-intestinal disorders, including the upper gastrointestinal tract of the oesophagus by administering an effective amount of a GLP-2 analogue, or a salt thereof as described herein. The stomach and intestinal-related disorders include ulcers of any aetiology (e.g., peptid ulcers, drug-induced ulcers, ulcers related to infections or other pathogens), digestion disorders, malabsorption syndromes, short-bowel syndrome, cul-de-sac syndrome, inflammatory bowel disease, celiac sprue (for example arising from gluten induced enteropathy or celiac disease), tropical sprue, hypogammaglobulinemic sprue, enteritis, ulcerative colitis, small intestine damage and Chemotherapy Induced diarrhea/mucositis (CID).

As mentioned above in general, individuals who would benefit from increased small intestinal mass and consequent and/or maintainance of normal small intestine mucosal structure and function are candidates for treatment with the present GLP-2 analogues. Particular conditions that may be treated with GLP-2 analogue include the various forms of sprue including celiac sprue which results from a toxic reaction to alpha-gliadin from heat and may be a result of gluten-induced enteropathy or celiac disease, and is marked by a significant loss of villae of the small bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the GLP-2 analogue treatment may be monitored by enteric biopsy to examine the villus morphology, by biochemical assessment of nutrient absorption, by patient weight gain, or by amelioration of the symptoms associated with these conditions.

Other conditions that may be treated with the GLP-2 analogues of the invention, or for which the GLP-2 analogues may be useful prophylactically, include in addition to the above mentioned radiation enteritis, infectious or post-infectious enteritis, and small intestinal damage due to cancer-chemotherapeutic or toxic agents.

The GLP-2 analogues may also be used for the treatment of malnutrition, for example cachexia and anorexia.

A particular embodiment the invention is concerned with using the present peptides for the prevention and/or treatment of intestinal damage and dysfunction. Such damage and dysfunction is a well-known side effect of cancer-chemotherapy treatment. Chemotherapy administration is frequently associated with unwanted side effects related to the gastronintestinal system such as mucositis, diarrhoea, bacterial translocation, malabsorption, abdominal cramping, gastrointestinal bleeding and vomiting. These side effects are clinical consequences of the structural and functional damage of the intestinal epithelium and frequently make it necessary to decrease the dose and frequency of chemotherapy. Administration of the present GLP-2 peptide agonists may enhance trophic effect in the intestinal crypts and rapidly provide new cells to replace the damaged intestinal epithelium following chemotherapy. The ultimate goal achieved by administering the present peptides is to reduce the morbidity related to gastrointestinal damage of patients undergoing chemotherapy treatment while creating the most optimal chemotherapy regime for the treatment of cancer. Concomitant prophylactic or therapeutic treatment may be provided in accordance with the present invention to patients undergoing or about to undergo radiation therapy.

The stem cells of the small intestinal mucosa are particularly susceptible to the cytotoxic effects of chemotherapy due to their rapid rate of proliferation (Keefe et al., Gut 2000; 47: 632-7). Chemotherapy-induced damage to the small intestinal mucosa is clinically often referred to as gastrointestinal mucositis and is characterized by absorptive and barrier impairments of the small intestine. For example, it has been shown that, the broadly used chemotherapeutic agents, 5-FU, irinotecan and methothrexate increase apoptosis leading to villus atrophy and crypt hypoplasia in the small intestine of rodents (Keefe et al., Gut 47: 632-7, 2000; Gibson et al., J Gastroenterol Hepatol. Sep; 18(9):1095-1100, 2003; Tamaki et al., J Int Med Res. 31(1):6-16, 2003). Chemotherapeutic agents have been shown to increase apoptosis in intestinal crypts at 24 hours after administration and subsequently to decrease villus area, crypt length, mitotic count per crypt, and enterocyte height three days after chemotherapy in humans (Keefe et al., Gut 2000; 47: 632-7). Thus, structural changes within the small intestine directly lead to intestinal dysfunction and in some cases diarrhea.

Gastrointestinal mucositis after cancer chemotherapy is an increasing problem that is essentially untreatable once established, although it gradually remits. Studies conducted with the commonly used cytostatic cancer drugs 5-FU and irinotecan have demonstrated that effective chemotherapy with these drugs predominantly affects structural integrity and function of the small intestine while the colon is less sensitive and mainly responds with increased mucus formation (Gibson et al., J Gastroenterol Hepatol. Sep; 18(9):1095-1100, 2003; Tamaki et al., J Int Med Res. 31(1):6-16, 2003).

The novel GLP-2 analogues of the present invention may be useful in the prevention and/or treatment of gastrointestinal injury and side effects of chemotherapeutic agents. This potentially important therapeutic application may apply to currently used chemotherapeutic agents such as but not limited to: 5-FU, Altretamine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Liposomal doxorubicin, Leucovorin, Lomustine, Melphalan, Mercaptopurine, Mesna, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, Vinorelbine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Liposomal doxorubicin, Leucovorin, Lomustine, Melphalan, Mercaptopurine, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, and Vinorelbine.

It is envisioned that the present peptides may be employed in a method of treating neo-natals by administering an effective amount of a GLP-2 analogue, or a salt thereof. Complications with feeding neonatals due to the lack of development of the intestine may be overcome by using the present peptide agonists.

In another embodiment the invention describes a method of treating DPP-IV (dipeptidylpeptidase-IV) mediated conditions by administering to a patient in need thereof an effective amount of a GLP-2 analogue, or a salt thereof. Such diseases include conditions in which the DPP-IV enzyme is over expressed.

The pharmaceutical composition may in one embodiment be formulated to cause slow release of said GLP-2 analogue, or a salt or derivative thereof as described above.

It is envisaged that the present peptides may be employed in a method of treating neo-natals by administering an effective amount of a GLP-2 analogue, or a salt thereof. Complications with feeding neonatals due to the lack of development of the intestine may be overcome by using the present peptide agonists.

In another embodiment the invention describes a method of treating DPP-IV (dipeptidylpeptidase-IV) mediated conditions by administering to a patient in need thereof an effective amount of a GLP-2 analogue, or a salt thereof. Such diseases include conditions in which the DPP-IV enzyme is over expressed.

EXAMPLES

The following examples are provided to illustrate preferred aspects of the invention and are not intended to limit the scope of the invention.

General Peptide Synthesis

Apparatus and Synthetic Strategy

Peptides were synthesized batchwise in a polyethylene vessel equipped with a polypropylene filter for filtration using 9-fluorenylmethyloxycarbonyl (Fmoc) as N-α-amino protecting group and suitable common protection groups for side-chain functionalities.

Solvents

Solvent DMF (N,N-dimethylformamide, Riedel de-Häen, Germany) was purified by passing through a column packed with a strong cation exchange resin (Lewatit S 100 MB/H strong acid, Bayer AG Leverkusen, Germany) and analyzed for free amines prior to use by addition of 3,4-dihydro-3-hydroxy-4-oxo-1,2,3-benzotriazine (Dhbt-OH) giving rise to a yellow color (Dhbt-O-anion) if free amines are present. Solvent DCM (dichloromethane, analytical grade, Riedel de-Häen, Germany) was used directly without purification. Acetonitril (HPLC-grade, Lab-Scan, Dublin Ireland) was used directly without purification.

Amino Acids

Fmoc-protected amino acids were purchased from Advanced ChemTech (ACT) in suitable side-chain protected forms.

Coupling Reagents

Coupling reagent diisopropylcarbodiimide (DIC) was purchased from Riedel de-Häen, Germany.

Solid Supports

Peptides were synthesized on TentaGel S resins 0.22-0.31 mmol/g. TentaGel S-Ram, TentaGel S RAM-Lys(Boc)Fmoc (Rapp polymere, Germany) were used in cases where a C-terminal amidated peptide was preferred, while TentaGel S PHB, TentaGel S PHB Lys(Boc)Fmoc were used when a C-terminal free carboxylic acid was preferred.

Catalysts and Other Reagents

Diisopropylethylamine (DIEA) was purchased from Aldrich, Germany, piperidine and pyridine from Riedel-de Häen, Frankfurt, Germany. Ethandithiol was purchased from Riedel-de Häen, Frankfurt, Germany. 3,4-dihydro-3-hydroxy-4-oxo-1,2,3-benzotriazine (Dhbt-OH), 1-hydroxybenzotriazole (HOBt) (HOAt) were obtained from Fluka, Switzerland. Acetic anhydride was obtained from Fluka.

Coupling Procedures

The amino acids were coupled as in situ generated HObt or HOAt esters made from appropriate N-a-protected amino acids and HObt or HOAt by means of DIC in DMF. Acylations were checked by the ninhydrin test performed at 80° C. in order to prevent Fmoc deprotection during the test (Larsen, B. D. and Holm, A., Int. J. Peptide Protein Res. 43, 1994, 1-9).

Deprotection of the N-α-Amino Protecting Group (Fmoc).

Deprotection of the Fmoc group was performed by treatment with 20% piperidine in DMF (1×5 and 1×10 min.), followed by wash with DMF (5×15 ml, 5 min. each) until no yellow color could be detected after addition of Dhbt-OH to the drained DMF.

Coupling of HOBt-Esters 3 eq. N-α-amino protected amino acid was dissolved in DMF together with 3 eq. HObt and 3 eq DIC and then added to the resin.

Cleavage of Peptide from Resin with Acid

Peptides were cleaved from the resins by treatment with 95% trifluoroacetic acid (TFA, Riedel-de Häen, Frankfurt, Germany)-water v/v or with 95% TFA and 5% ethanditiol v/v at r.t. for 2 h. The filtered resins were washed with 95% TFA-water and filtrates and washings evaporated under reduced pressure. The residue washed with ether and freeze dried from acetic acid-water. The crude freeze dried product was analyzed by high-performance liquid chromatography (HPLC) and identified by mass spectrometry (MS).

Batchwise Peptide Synthesis on TentaGel Resin (PEG-PS)

TentaGel resin (1 g, 0.23-0.24 mmol/g) was placed in a polyethylene vessel equipped with a polypropylene filter for filtration. The resin was swelled in DMF (15 ml), and treated with 20% piperidine in DMF in order to remove the initial Fmoc group either on the linker TentaGel S RAM or on the first amino acid on the resin TentaGel S RAM-Lys(Boc) Fmoc. The resin was drained and washed with DMF until no yellow color could be detected after addition of Dhbt-OH to the drained DMF. The amino acids according to the sequence were coupled as preformed Fmoc-protected HObt esters (3 eq.) as described above. The couplings were continued for 2 h, unless otherwise specified.

The resin was drained and washed with DMF (5×15 ml, 5 min each) in order to remove excess reagent. All acylations were checked by the ninhydrin test as described above. After completed synthesis the peptide-resin washed with DMF (3×15 ml, 5 min each), DCM (3×15 ml, 1 min each) and finally diethyl ether (3×15 ml, 1 min each) and dried in vacuo. The peptide was cleaved from the resin as described earlier and the crude peptide product was analysed and purified as described below HPLC Conditions Gradient HPLC analysis was done using a Hewlett Packard HP 1100 HPLC system consisting of a HP 1100 Quaternary Pump, a HP 1100 Autosampler a HP 1100 Column Thermostat and HP 1100 Multiple Wavelength Detector. Hewlett Packard Chemstation for LC software (rev. A.06.01) was used for instrument control and data acquisition. The following columns and HPLC buffer system was used:

Column: VYDAC 238TP5415, C-18, 5 mm, 300 Å 150×4.6 mm.

Buffers: A: 0.1% TFA in MQV; B: 0.085% TFA, 10% MQV, 90% MeCN.

Gradient: 0-1.5 min. 0% B
1.5-25 min 50% B
25-30 min 100% B
30-35 min 100% B
35-40 min 0% B Flow 1, ml/min, oven temperature 40° C., UV detection: I=215 nm.

HPLC Purification of the Crude Peptide

The crude peptide products were purified PerSeptive Biosystems VISION Workstation. VISION 3.0 software was used for instrument control and data acquisition. The following column and HPLC buffer system was used:

Column: Kromasil KR 100 Å, 10 mm C-8, 250×50.8 mm.

Buffer system: Buffers: A: 0.1% TFA in MQV; B: 0.085% TFA, 10% MQV, 90% MeCN.

Gradient: 0-37 min. 0-40% B

Flow 35 ml/min, UV detection: I=215 nm and 280 nm.

Mass Spectroscopy

The peptides were dissolved in super gradient methanol (Labscan, Dublin, Ireland), milli-Q water (Millipore, Bedford, Mass.) and formic acid (Merck, Damstadt, Germany) (50:50:0.1 v/v/v) to give concentrations between 1 and 10 mg/ml. The peptide solutions (20 ml) were analysed in positive polarity mode by ESI-TOF-MS using a LCT mass spectrometer (Micromass, Manchester, UK) accuracy of +/−0.1 m/z.

General Synthetic Procedure

In all syntheses dry TentaGel-S-Ram resin (1 g, 0.22-0.31 mmol/g) was placed in a polyethylene vessel equipped with a polypropylene filter for filtration. The resin was swelled in DMF (15 ml), and treated with 20% piperidine in DMF to secure the presence of non-protonated amino groups on the resin. The resin was drained and washed with DMF until no yellow colour could be detected after addition of Dhbt-OH to the drained DMF. The amino acids according to the sequence were coupled as preformed Fmoc-protected HOBt esters (3 eq.) as described above. The couplings were continued for 2 h, unless otherwise specified. The resin was drained and washed with DMF (5×15 ml, 5 min each) in order to remove excess reagent. All acylations were checked by the ninhydrin test performed at 80° C. After completed synthesis the peptide-resin washed with DMF (3×15 ml, 5 min each), DCM (3×15 ml, 1 min each) and finally diethyl ether (3×15 ml, 1 min each) and dried in vacuo. The peptide was then cleaved from the resin as described above and freeze dried. After purification using preparative HPLC as described above, the peptide product was collected and the identity of the peptide was confirmed by ES-MS. This procedure was used for the synthesis of all peptides exemplified further below.

Compounds Synthesised

Using the above techniques compounds 1809 to 1861 (SEQ ID NOS:1-49) and reference compound 1559 (H-[Gly2]hGLP-2-OH) (SEQ ID NO:54) were synthesised using the methods described above (Table 1).

TABLE 1

Compounds synthesized

| Compound # | Sequence | Mw calc | Mw found | purity % | Yield* |
|---|---|---|---|---|---|
| 1559 (SEQ ID NO:54) | H-HGDGSFSDEMNTILDNLAARDFINWLIQTKITD-NH2 | 3749.80 | 3749.16 | 95 | 5.4 |
| 1809 (SEQ ID NO:1) | H-HGEGTFSDELATILDALAARDFIAWLIATKITDKKKKKK-NH2 | 4341.42 | 4341.62 | 96 | 46.5 |
| 1810 (SEQ ID NO:2) | H-HGEGTFSDELATILDALAARIFIAWLIATKKKKKKK-NH2 | 4010.32 | 4010.63 | 91 | 20 |
| 1811 (SEQ ID NO:3) | H-HGDGSPSDELATILDALAARDFIAWLIATKITD-NH2 | 3494.8 | 3494.13 | 94 | 44.7 |
| 1812 (SEQ ID NO:4) | H-HGEGSFSDELATILDNLAARDFIAWLIQTKITD-NH2 | 3658.86 | 3658.3 | 91 | 8 |
| 1813 (SEQ ID NO:5) | H-HGDGSFSDELATILDALAARDFIAWLIATKITD-NH2 | 3544.82 | 3545 | 95 | 15.9 |
| 1814 (SEQ ID NO:6) | H-HGDGSFSDELATILDNLAARDFIAWLIATKITD-NH2 | 3587.83 | 3588 | 92 | 31 |
| 1815 (SEQ ID NO:7) | H-HGEGSFSDELATILDALAARDFIAWLIATKITD-NH2 | 3558.84 | 3559 | 95 | 33 |
| 1818 (SEQ ID NO:8) | H-HGDGSFSSELATILDNLAARDFIAWLIQTKKKKKKK-NH2 | 4056.26 | 4056.25 | 92 | 68.3 |
| 1819 (SEQ ID NO:9) | H-HGDGSFSDELSTILDNLAARDFIAWLIQTKKKKKKK-NH2 | 4100.25 | 4100.13 | 92 | 38.7 |
| 1820 (SEQ ID NO:10) | H-HGDGSFTSELATILDNLAARDFIAWLIQTKKKKKKK-NH2 | 4070.28 | 4070.38 | 94 | 63.3 |
| 1821 (SEQ ID NO:11) | H-HGDGSFSDELKTILDNLAARDFIAWLIQTKKKKKKK-NH2 | 4141.32 | 4141.5 | 93 | 57.3 |
| 1822 (SEQ ID NO:12) | H-HGDGSFTDELKTILDNLAARDFIAWLIQTKKKKKKK-NH2 | 4155.33 | 4155.13 | 94 | 72 |
| 1823 (SEQ ID NO:13) | H-HGDGSFTSELKTILDNLAARDFIAWLIQTKKKKKKK-NH2 | 4127.34 | 4127.9 | 95 | 100.3 |
| 1824 (SEQ ID NO:14) | H-HGDGSFTDELATILDNLAARDFIAWLIQTKKKKKKK-NH2 | 4098.27 | 4098.25 | 95 | 33.9 |
| 1825 (SEQ ID NO:15) | H-HGDGSFSSELATILDNLAARDFIAWLIQTK-NH2 | 3287.69 | 3287.75 | 92 | 82.0 |
| 1826 (SEQ ID NO:16) | H-HGDGSFSDELNTILDNLAARDFIAWLIQTKITDKKKKKK-NH2 | 4456.42 | 4456.38 | 93 | 68.9 |
| 1827 (SEQ ID NO:17) | H-HGDGSFTDELSTILDNLAARDFIAWLIQTKKKKKKK-NH2 | 4114.27 | 4114.63 | 93 | 20.2 |
| 1828 (SEQ ID NO:18) | H-HGDGSFTSELSTILDNLAARDFIAWLIQTKKKKKKK-NH2 | 4086.27 | 4086.63 | 94 | 84.5 |
| 1829 (SEQ ID NO:19) | H-HGDGSFSSELSTILDNLAARDFIAWLIQTKKKKKKK-NH2 | 4072.26 | 4072.5 | 95 | 51.8 |
| 1830 (SEQ ID NO:20) | H-HGDGSFSDELSTILDNLAARDFIAWLIQTK-NH2 | 3331.68 | 3331.88 | 94 | 26.4 |
| 1831 (SEQ ID NO:21) | H-HGDGSFTDELSTILDNLAARDFIAWLIQTK-NH2 | 3345.7 | 3345.38 | 94 | 46.0 |
| 1832 (SEQ ID NO:22) | H-HGDGSFTSELSTILDNLAARDFIAWLIQTK-NH2 | 3317.7 | 3117.88 | 94 | 17.5 |
| 1833 (SEQ ID NO:23) | H-HGDGSFSSELSTILDNLAARDFIAWLIQTK-NH2 | 3303.69 | 3304.13 | 97 | 34.5 |
| 1834 (SEQ ID NO:24) | H-HGDGSFTSELATILDNLAARDFIAWLIQTK-NH2 | 3301.71 | 3301.75 | 94 | 16.0 |
| 1835 (SEQ ID NO:25) | H-HGDGSFSDELKTILDNLAARDFIAWLIQTK-NH2 | 3372.75 | 3373.13 | 94 | 89.7 |

TABLE 1-continued

Compounds synthesized

| Compound # | Sequence | Mw calc | Mw found | purity % | Yield* |
|---|---|---|---|---|---|
| 1836 (SEQ ID NO:26) | H-HGDGSFTDELKTILDNIAARDFIAWLIQTK-NH2 | 3386.76 | 3386.88 | 92 | 26.0 |
| 1839 (SEQ ID NO:27) | H-HGDGSFSDELATILDNLAARDFIAWLIQTKITDKKKKKK-NH2 | 4413.42 | 4413.88 | 92 | 18.2 |
| 1840 (SEQ ID NO:28) | H-HGDGSFSDELATILDNLAARDFIAWLIQTKITD-NH2 | 3644.85 | 3644.88 | 95 | 21.3 |
| 1841 (SEQ ID NO:29) | H-HGDGSFSDELATILDNLAARDFIAWLIQTK-NH2 | 3315.69 | 3315.88 | 91 | 73.6 |
| 1842 (SEQ ID NO:30) | H-HGDGSFTSELKTILDNLAARDFIAWLIQTK-NH2 | 3358.77 | 3358.88 | 97 | 26.3 |
| 1843 (SEQ ID NO:31) | H-HGDGSFTDELATILDNLAARDFIAWLIQTK-NH2 | 3329.7 | 3329.88 | 90 | 23.6 |
| 1844 (SEQ ID NO:32) | H-HGEGTFSSELSTILDALAARDFIAWLIATKITDKKKKKK-NH2 | 4329.42 | 4329.63 | 90 | 46.0 |
| 1845 (SEQ ID NO:33) | H-HGEGTFSDELSTILDALAARDFIAWLIATKITDKKKKKK-NH2 | 4357.42 | 4357.38 | 93 | 52.5 |
| 1846 (SEQ ID NO:34) | H-HGEGSFSSELSTILDALAARDFIAWLIATKITDKKKKKK-NH2 | 4315.41 | 4315.38 | 90 | 28.8 |
| 1847 (SEQ ID NO:35) | H-HGEGSFSDELSTILDALAARDFIAWLIATKITDKKKKKK-NH2 | 4343.4 | 4343.5 | 90 | 59.4 |
| 1848 (SEQ ID NO:36) | H-HGEGTFSSELATILDALAARDFIAWLIATKITDKKKKKK-NH2 | 4313.43 | 4313.63 | 90 | 230.0 |
| 1849 (SEQ ID NO:37) | H-HGEGSFSSELATILDALAARDFIAWLIATKITDKKKKKK-NH2 | 4299.41 | 4299.5 | 97 | 68.0 |
| 1850 (SEQ ID NO:38) | H-HGEGSFSDELKTILDALAARDFIAWLIATKITDKKKKKK-NH2 | 4384.46 | 4384.63 | 93 | 38.0 |
| 1851 (SEQ ID NO:39) | H-HGEGTFSDELKTILDALAARDFIAWLIATKITDKKKKKK-NH2 | 4398.48 | 4398.38 | 95 | 90.6 |
| 1852 (SEQ ID NO:40) | H-HGEGTFSSELKTILDALAARDFIAWLIATKITDKKKKKK-NH2 | 4370.48 | 4370.63 | 95 | 63.2 |
| 1853 (SEQ ID NO:41) | H-HGEGTFSSELSTILDALAARDFIAWLIATKITD-NH2 | 3560.85 | 3560.13 | 97 | 18.0 |
| 1854 (SEQ ID NO:42) | H-HGEGTFSDELSTILDALAARDFIAWLIATKITD-NH2 | 3588.85 | 3589.13 | 96 | 12.5 |
| 1855 (SEQ ID NO:43) | H-HGEGSFSSELSTILDALAARDFIAWLIATKITD-NH2 | 3546.84 | 3547 | 96 | 27.3 |
| 1856 (SEQ ID NO:44) | H-HGEGSFSDELSTILDALAARDFIAWLIATKITD-NH2 | 3574.83 | 3575 | 96 | 18.0 |
| 1857 (SEQ ID NO:45) | H-HGEGTFSSELATILDALAARDFIAWLIATKITD-NH2 | 3544.86 | 3544.88 | 94 | 39.3 |
| 1858 (SEQ ID NO:46) | H-HGEGSFSSELATILDALAARDFIAWLIATKITD-NH2 | 3530.84 | 3530.88 | 90 | 43.3 |
| 1859 (SEQ ID NO:47) | H-HGEGSFSDELKTILDALAARDFIAWLIATKITD-NH2 | 3615.89 | 3615.13 | 90 | 11.4 |
| 1860 (SEQ ID NO:48) | H-HGEGTFSDELKTILDALAARDFIAWLIATKITD-NH2 | 3629.91 | 3629.13 | 92 | 13.9 |
| 1861 (SEQ ID NO:49) | H-HGEGTFSSELKTILDALAARDFIAWLIATKITD-NH2 | 3601.91 | 3601.13 | 99 | 16.2 |

*Yield; yield/g resin

Example 1

Synthesis of Compound 1846 (SEQ ID NO:34)

H-His-Gly-Glu-Gly-Ser-Phe-Ser-Ser-Glu-Leu-Ser-Thr-Ile-Leu-Asp-Ala-Leu-Ala-Ala-Arg-Asp-Phe-Ile-Ala-Trp-Leu-Ile-Ala-Thr-Lys-Ile-Thr-Asp-Lys-Lys-Lys-Lys-Lys-Lys-NH$_2$ (SEQ ID NO:34) on TentaGel S RAM-Lys(Boc)Fmoc.

Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, 28.8 mg peptide product was collected with a purity better than 90% and the identity of the peptide was confirmed by MS (found M 4315.38, calculated M 4315.41).

Example 2

Synthesis of Compound 1848 (SEQ ID NO:36)

H-His-Gly-Glu-Gly-Thr-Phe-Ser-Ser-Glu-Leu-Ala-Thr-Ile-Leu-Asp-Ala-Leu-Ala-Ala-Arg-Asp-Phe-Ile-Ala-Trp-Leu-Ile-Ala-Thr-Lys-Ile-Thr-Asp-Lys-Lys-Lys-Lys-Lys-Lys-NH$_2$ (SEQ ID NO:36) on TentaGel S RAM-Lys(Boc)Fmoc.

Dry TentaGel S RAM-Lys(Boc)Fmoc (0.24 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, 230 mg peptide product was collected with a purity better than 90% and the identity of the peptide was confirmed by MS (found M 4313.63, calculated M 4313.43).

Example 3

Synthesis of Compound 1855 (SEQ ID NO:43)

H-His-Gly-Glu-Gly-Ser-Phe-Ser-Ser-Glu-Leu-Ser-Thr-Ile-Leu-Asp-Ala-Leu-Ala-Ala-Arg-Asp-Phe-Ile-Ala-Trp-Leu-Ile-Ala-Thr-Lys-Ile-Thr-Asp-NH$_2$ (SEQ ID NO:43) on TentaGel S RAM-Asp(OtBu)Fmoc.

Dry TentaGel S RAM-Asp(OtBu)Fmoc (0.2 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, 27.3 mg peptide product was collected with a purity better than 96% and the identity of the peptide was confirmed by MS (found M 3547, calculated M 3546.84).

Example 4

Synthesis of Compound 1857 (SEQ ID NO:45)

H-His-Gly-Glu-Gly-Thr-Phe-Ser-Ser-Glu-Leu-Ala-Thr-Ile-Leu-Asp-Ala-Leu-Ala-Ala-Arg-Asp-Phe-Ile-Ala-Trp-Leu-Ile-Ala-Thr-Lys-Ile-Thr-Asp-NH$_2$ (SEQ ID NO:45) on TentaGel S RAM-Asp(OtBu)Fmoc.

Dry TentaGel S RAM-Asp(OtBu)Fmoc (0.2 mmol/g, 1 g) was placed in a polyethylene vessel equipped with a polypropylene filter for filtration and treated as described under "batchwise peptide synthesis on TentaGel resin" until finishing the coupling of the N-terminal Histidine. All couplings were continued over night. The acylations were checked as earlier described. After completed synthesis and deprotection of the N-terminal Fmoc group the peptide was cleaved from the resin as described above. After purification using preparative HPLC as earlier described, 39.3 mg peptide product was collected with a purity better than 94% and the identity of the peptide was confirmed by MS (found M 3544.88, calculated M 3544.86).

Example 5

Synthesis of Compound 1846 A (SEQ ID NO:34) (Acetate Salt)

Counter ion exchange from trifluoroacetate to acetate of Compound 1846 (SEQ ID NO:34). The purified synthetic peptide product of compound 1846 (SEQ ID NO:34) is isolated as a trifluoroacetate salt, due to the presence of trifluoroacetic acid (0.1% v/v) in the HPLC buffers used for the purification of the crude synthetic peptide product.

In order to exchange the counter ion trifluoroacetate with acetate, a solution of the peptide was passed through a column packed with strong base ion exchange resin on the acetate (Dowex 1×8). 365 mg Compound 1 is dissolved in 40 ml water. The solution is passed through a column containing 40 ml strong base ion exchange resin on the acetate (Dowex 1×8; capacity 1.33 meq/ml resin). The resin is then washed with 4×30 ml water and the eluate is collected and lyophilized resulting in 312 mg acetate salt with a purity according to HPLC analysis of 97%.

Example 6

Synthesis of Compound 1848 (SEQ ID No:36) C (Chloride Salt)

Counter ion exchange from trifluoroacetate (Tfa) to chloride (Cl—) of Compound 1848 (SEQ ID NO:36).

100 mg Compound 1 was dissolved in 50 ml 0.1M hydrochloric acid and the resulting solution was lyophilized. The remanence was dissolved in 50 ml water and lyophilized again resulting in 80 mg of the chloride salt with a purity according to HPLC of 93%.

Example 7

Chemical Stability Testing

The GLP-2 analogues were dissolved in purified water and subsequently diluted in solutions containing HCl, NaOH, H$_2$O$_2$ or NH$_4$HCO$_3$. The solutions were incubated at 40° C. to produce hydrolysis, deamidation and oxidation products. The samples were analyzed by RP-HPLC and the percentage of remaining intact compound was determined as a measure for the relative stability. The major degradation products were tentatively identified by LC-MS. The peptides used are listed in Table 3.

TABLE 2

GLP-2 analogues tested and compared for chemical stability.

| Compound No. | Batch No. | Monoisotopic MW (g/mol) | Peptide Content (%) | Purity RP-HPLC (%) |
|---|---|---|---|---|
| ZP1559 (SEQ ID NO:54) | 70.30 AB and K 1A | 3749.80 | 90 | 96 |
| ZP1820 (SEQ ID NO:10) | 78.65 1A | 4070.28 | 80 | 94 |
| ZP1834 (SEQ ID NO:24) | 78.90 1A | 3301.71 | 88 | 94 |
| ZP1846 (SEQ ID NO:34) | 107.07 1A | 4315.41 | 80 | 90 |
| ZP1848 (SEQ ID NO:36) | 91.58 1A | 4313.43 | 80 | 90 |
| ZP1849 (SEQ ID NO:37) | 91.60 1A | 4299.41 | 79 | 97 |
| ZP1855 (SEQ ID NO:43) | 88.49 1A-2-1A | 3546.84 | 89 | 96 |
| ZP1857 (SEQ ID NO:45) | 108.01 X-1A | 3544.86 | 89 | 94 |
| ZP1858 (SEQ ID NO:46) | 108.05 1A | 3530.84 | 89 | 90 |

Compound ZP1559 (SEQ ID NO:54), Gly$^2$-GLP-2, was used as a reference for the other GLP-2 analogues tested. In the GLP-2 analogues, positions where the sequence differs from the reference compound ZP1559 (SEQ ID NO:54) are shown in bold font. The sequences are listed in Table 3.

The compounds are listed as pairs according to their sequences and with and without C-terminal -$K_6$ extension.

TABLE 3

Sequences of Gly²-GLP-2 and GLP-2 analogues.

| Compound | Sequence |
|---|---|
| ZP1559 (SEQ ID NO:54) | HGDGS FSDEM NTILD NLAAR DFINW LIQTK ITD-OH |
| ZP1820 (SEQ ID NO:10) | HGDGS FTSEL ATILD NLAAR DFIAW LIQTK $K_6$-$NH_2$ |
| ZP1834 (SEQ ID NO:24) | HGDGS FTSEL ATILD NLAAR DFIAW LIQTK -$NH_2$ |
| ZP1846 (SEQ ID NO:34) | HGEGS FSSEL STILD ALAAR DFIAW LIATK ITD $K_6$-$NH_2$ |
| ZP1855 (SEQ ID NO:43) | HGEGS FSSEL STILD ALAAR DFIAW LIATK ITD-$NH_2$ |
| ZP1848 (SEQ ID NO:36) | HGEGT FSSEL ATILD ALAAR DFIAW LIATK ITD $K_6$-$NH_2$ |
| ZP1857 (SEQ ID NO:45) | HGEGT FSSEL ATILD ALAAR DFIAW LIATK ITD-$NH_2$ |
| ZP1849 (SEQ ID NO:37) | HGEGS FSSEL ATILD ALAAR DFIAW LIATK ITD $K_6$-$NH_2$ |
| ZP1858 (SEQ ID NO:46) | HGEGS FSSEL ATILD ALAAR DFIAW LIATK ITD-$NH_2$ |

Chemicals used in the experiment are listed in Table 4.

TABLE 4

Chemicals and reagents used for the analytical procedures.

| Substance | Quality | Supplier | Product |
|---|---|---|---|
| Acetonitrile (MeCN) | HPLC grade | Riedel-deHaen | 34851 |
| Trifluoroacetic Acid (TFA) | 99.9% | Pierce | 28904 |
| Formic Acid (FA) | 98-100% | Merck | 1.00264.1000 |
| Hydrochloric acid HCl | "Baker Analyzed" | J. T. Baker | 7088 |
| Sodium Hydroxide NaOH | "Baker Analyzed" | J. T. Baker | 7098 |
| Hydrogen Peroxide $H_2O_2$ | 30% w/w | Sigma-Aldrich | H1009 |
| $NH_4HCO_3$ | 99.0% | AnalaR | 103025E |

The water was first de-mineralized to a resistance of $\geq 18$ MΩcm and then passed through a Milli-Q system (Millipore, Bedford, USA). The Milli-Q purified water (MQW) was finally tapped through a 0.22-µm sterile filter (Millipak 40 Gamma Gold, Millipore).

The GLP-2 analogues tested and the reference Gly2-GLP-2, ZP1559 (SEQ ID NO:54), were dissolved in water and subsequently diluted into solutions containing HCl, NaOH, $H_2O_2$ or $NH_4HCO_3$.

The samples were incubated at 40° C. to generate hydrolysis, deamidation and oxidation products, respectively. The compounds were analysed by RP-HPLC for purity of the original main peak and by LC-MS for confirmation of the identity by mass of the main peak and major degradation products.

Preparation of Stress Solutions:

| | |
|---|---|
| 0.2 M HCl: | 4 mL MQW and 1 mL of 1 M HCl. |
| 0.02 M NaOH: | 4 mL MQW and 1 mL of 0.1 M NaOH. |
| 0.2 M $NH_4HCO_3$, pH 8: | 0.79 g $NH_4HCO_3$ was dissolved in 50 mL MQW. |
| 1% $H_2O_2$: | 5.8 mL MQW and 0.2 mL of 30% $H_2O_2$. |

Sample Solutions:

The GLP-2 analogues were first dissolved in MQW to a concentration of 4 mg/mL and then further diluted in the stress solutions at a 1:1 ratio (e.g. 125 µL plus 125 µL). The final concentrations were 2 mg/mL of the GLP-2 analogues for stress conditions with 0.1 M HCl, 0.01 M NaOH, 0.1 M $NH_4HCO_3$ and 0.5% $H_2O_2$, respectively.

The solutions were incubated at 40° C. in the dark and then diluted in Eluent A to a concentration of 0.5 mg/mL (addition of 750 µL) prior to analyses by RP-HPLC and by LC-MS.

TABLE 5

Conditions for stress test.

| | Solution | | | |
|---|---|---|---|---|
| | 0.1 M HCl | 0.01M NaOH | 0.1 M $NH_4HCO_3$ | 0.5% $H_2O_2$ |
| Temperature (° C.) | 40 | 40 | 40 | 40 |
| Storage (days) | 12 | 3 | 6 | 3 |

RP-HPLC

The RP-HPLC analyses were performed on an Agilent Series 1100 HPLC system under control of the ChemStation (Revision A.08.03 [847]) software from Agilent Technologies, Inc. The raw data and the results of the peak integration were deposited on the ChemStore C/S server by the use of Agilent Technologies Revision B01.03 software.

TABLE 6

The RP-HPLC method.

| | |
|---|---|
| Method file name | P2204071.M |
| Column | Vydac 218MS52, 5 µm, 300 Å, 2.1 × 250 mm |
| Gradient (time; % B) | 0; 5, 2; 5, 7; 15, 25; 30, 45; 40, 65; 50, 70; 100, 73; 100, 75; 5, 90; 5 |
| Eluent A | 0.05% TFA, 0.05% FA in MQW |
| Eluent B | 0.05% TFA, 0.05% FA in MeCN |
| Flow Rate | 0.200 mL/min |
| Injection Volume | 20 µL |
| Column Temperature | 25° C. |
| Auto Sampler Temp. | 4° C. |
| UV detection | 220 nm |

LC-MS

Analytical LC-MS analyses were performed on an Agilent Technologies 1100 HPLC instrument consisting of an on-line degasser, quaternary gradient pump, an auto sampler, a column oven, an UV detector. The HPLC instrument was interfaced with a Micromass LCT (ESI-TOF) mass spectrometer under control of Masslynx 3.5 software, from MicroMass, UK.

TABLE 7

The LC-MS method

| | |
|---|---|
| Method file name | P22_04_071_003.M |

TABLE 7-continued

The LC-MS method

| | |
|---|---|
| Column | Vydac 218MS52, 5 µm, 300 Å, 2.1 × 250 mm |
| Gradient (time; % B) | 0; 5, 2; 5, 7; 15, 25; 30, 45; 40, 65; 50, 70; 100, 73; 100, 75; 5, 90; 5 |
| Eluent A | 0.05% TFA, 0.05% FA in MQW |
| Eluent B | 0.05% TFA, 0.05% FA in MeCN |
| Flow Rate | 0.200 mL/min |
| Injection Volume | 30 µL |
| Column Temperature | 25° C. |
| Auto Sampler Temp. | 4° C. |
| UV detection | 220 nm |

TABLE 8

The MS set-up according to SOP 22-3003.

| | |
|---|---|
| Cone voltage | 30 V |
| Capillary voltage | 3.1 kV |
| Nitrogen nebuliser gas flow | 100 L/hr |
| Desolvation gas flow | 500 L/hr |
| Desolvation temperature | 250° C. |
| Source block temperature | 100° C. |

The results are shown in Table 9 as the compound purity measured by RP-HPLC after incubation under stress conditions. This purity is a measure for the remaining intact compound after incubation in stress solutions, relative to the purity measured a T=0. These results do not take into account possible hidden degradation products not observed by this analytical RP-HPLC method.

Major degradation products in the stress test samples were tentatively identified by the LC-MS method. Any isomers to the parent compounds and minor degradation products were not observed by this analytical LC-MS method. Tentative identifications are listed in Tables 11 to 15.

The GLP-2 analogues tested are listed as pairs according to theirs sequences with and without the C-terminal -$K_6$ extension.

TABLE 9

Observed purity of test compounds after incubation under stress conditions.

| GLP-2 analogues | Sequence +/− C-terminal $K_6$ | Purity HCl 0.1 M 12 days (%) | Purity $H_2O_2$ 0.5 % 3 days (%) | Purity $NH_4HCO_3$ 0.1 M 6 days (%) |
|---|---|---|---|---|
| ZP1559 (SEQ ID NO:54) | Reference | 57 | <5 | 66 |
| ZP1820 (SEQ ID NO:10) | $K_6$ | 45 | 62 | 85 |
| ZP1834 (SEQ ID NO:24) | − | 38 | 53 | 91 |
| ZP1846 (SEQ ID NO:34) | $K_6$ | 70 | 64 | 82 |
| ZP1855 (SEQ ID NO:43) | − | 85 | 14 | 97 |
| ZP1848 (SEQ ID NO:36) | $K_6$ | 63 | 68 | 93 |
| ZP1857 (SEQ ID NO:45) | − | 86 | 59 | 96 |
| ZP1849 (SEQ ID NO:37) | $K_6$ | 64 | 78 | 86 |
| ZP1858 (SEQ ID NO:46) | − | 88 | 60 | 91 |

The results for the compounds incubated in NaOH are not listed, because no difference in the stability could be observed. The degradation products and the main peak all have the same mass by LC-MS analysis; these compounds were probably racemized over time. The results in Table 9 show that the GLP-2 analogues tested in general are more chemically stable than the Gly2-GLP-2 reference, ZP1559 (SEQ ID NO:54).

During acid hydrolysis the GLP-2 analogues tested are more stable than the Gly$^2$-GLP-2 reference, ZP1559 (SEQ ID NO:54), except for the ZP1820 (SEQ ID NO:10) and ZP1834 (SEQ ID NO:24). This is mainly due to the amino acid Asp in position 3. Glu rather than Asp may minimize the cleavage between amino acid 3 and 4 Asp-Gly. The other ZP GLP-2 analogues tested do have approximately the same stability and with a tendency of slightly higher stability for the compounds without C-terminal -$K_6$, ZP1855 (SEQ ID NO:43), ZP1857 (SEQ ID NO:45), and ZP1858 (SEQ ID NO:46). This difference is explained by the amino acid in position 33 Asp. In the compound without C-terminal -$K_6$, this amino acid is C-terminal and a cleavage between amino acid 32 and 33 Tyr-Asp occurs slower than for a cleavage between amino acid 33 and 34 Asp-Lys. The difference in the stability is due to the Asp and not to the C-terminal -$K_6$.

Under the conditions of accelerated oxidation ($H_2O_2$, se also Table 10 and 13), the GLP-2 analogues tested are much more stable than the Gly$^2$-GLP-2 reference, ZP1559 (SEQ ID NO:54). This is probably due to oxidation of Met in position 10 in ZP1559 (SEQ ID NO:54). An exception is ZP1855 (SEQ ID NO:47), which shows an unexplainable low stability. This could be specific for the batch of ZP1855 (SEQ ID NO:47) and further studies will be needed to explain this.

The stability under conditions promoting deamidation ($NH_4HCO_3$), the GLP-2 analogues tested are more stable than the Gly2-GLP-2 reference, ZP1559 (SEQ ID NO:54). This is probably due to several deamidation sites in ZP1559 (SEQ ID NO:54), Asn in position 11, 16 and 24, which are not present in the sequences for the GLP-2 analogues tested.

Tentative Identification of Major Degradation Products by LC-MS

TABLE 10

Major cleavage sites in ZP GLP-2 analogues and the reference ZP1559 (SEQ ID NO:54).

| | |
|---|---|
| ZP1559HGD↓GS FSDEM N↓TILD NLAAR DFINW LIQTK ITD-OH | (SEQ ID NO:54) |
| ZP1820HGD↓GS FTSEL ATILD NLAAR DFIAW LIQTK $K_6$-$NH_2$ | (SEQ ID NO:10) |

TABLE 10-continued

Major cleavage sites in ZP GLP-2 analogues and the reference ZP1559 (SEQ ID NO:54).

ZP1834 HGD↓GS FTSEL ATILD NLAAR DFIAW LIQTK -NH$_2$ (SEQ ID NO:24)

ZP1846 HGEGS FSSEL STILD ALAAR DFIAW LIATK ITD↓K$_6$-NH$_2$ (SEQ ID NO:34)

ZP1855 HGEGS FSSEL STILD ALAAR DFIAW LIATK IT↓D-NH$_2$ (SEQ ID NO:43)

ZP1848 HGEGT FSSEL ATILD ALAAR DFIAW LIATK ITD↓K$_6$-NH$_2$ (SEQ ID NO:36)

ZP1857 HGEGT FSSEL ATILD ALAAR DFIAW LIATK IT↓D-NH$_2$ (SEQ ID NO:45)

ZP1849 HGEGS FSSEL ATILD ALAAR DFIAW LIATK ITD↓K$_6$-NH$_2$ (SEQ ID NO:37)

ZP1858 HGEGS FSSEL ATILD ALAAR DFIAW LIATK IT↓D-NH$_2$ (SEQ ID NO:46)

Solutions Stressed by HCl

TABLE 11

GLP-2 analogues incubated 12 days at 40° C. in 0.1 M HCl.

| GLP-2 analogues | Measured MW (Da) | Theoretical MW (Da) | Difference Mass (Da) | Major/minor abundance Possible ID suggestion |
|---|---|---|---|---|
| ZP1559 (SEQ ID NO:54) | 3749.88 | 3749.80 | +0.08 | Major product |
|  | 3732.75 | Na | −17.13 | Minor, cyclic deamidation |
|  | 3751.88 | Na | +2.00 | Minor, 2 × deamidation |
| ZP1820 (SEQ ID NO:10) | 4070.13 | 4070.28 | −0.15 | Major product $A^1$-$A^{36}$ |
|  | 4071.25 | Na | +1.12 | Minor, deamidation |
|  | 3761.25 | 3761.17 | +0.08 | Minor, hydrolysis $A^4$-$A^{36}$ |
|  | 2526.75 | 2526.56 | +0.19 | Minor, hydrolysis $A^{16}$-$A^{36}$ |
|  | 3762.25 | 3762.16 | +0.09 | Minor, hydro. $A^4$-$A^{36}$, dea. |
| ZP1834 (SEQ ID NO:24) | 3302.00 | 3301.71 | +0.29 | Major product |
|  | 3303.00 | Na | +1.00 | Minor, deamidation |
|  | 3283.88 | Na | −18.12 | Minor, cyclic deamidation |
|  | 3302.88 | Na | +0.88 | Minor, deamidation |
|  | 2992.88 | 2992.60 | −309.12 | Major, hydro. $A^4$-$A^{30}$, dea. |
|  | 2993.88 | 2993.59 | −308.12 | Minor, hydrolysis $A^4$-$A^{30}$ |
|  | 2993.75 | 2993.59 | −308.25 | Minor, hydrolysis $A^4$-$A^{30}$ |
| ZP1846 (SEQ ID NO:34) | 4315.00 | 4315.41 | +0.59 | Major product $A^1$-$A^{39}$ |
|  | 3547.50 | 3547.82 | −0.32 | Minor, hydrolysis $A^1$-$A^{33}$ |
|  | 3934.88 | 3935.26 | −0.38 | Minor, hydrolysis $A^5$-$A^{33}$ |
|  | 2755.38 | 2755.70 | −0.32 | Minor, hydrolysis $A^{16}$-$A^{39}$ |
|  | 2158.25 | 2158.37 | −0.12 | Minor, hydrolysis $A^{22}$-$A^{39}$ |
|  | 3155.16 | Na | −1160.25 | No suggestion |
| ZP1855 (SEQ ID NO:43) | 3548.13 | 3546.84 | +1.29 | Major product/deamida. |
|  | 3548.13 | Na | +1.29 | Minor, deamidation |
|  | 3225.13 | 3223.71 | +1.42 | Minor, hydro. $A^4$-$A^{33}$, dea. |
|  | 3433.13 | 3432.79 | +0.34 | Minor, hydrolysis $A^1$-$A^{32}$ |
|  | 3354.50 | 3352.76 | +1.76 | Minor, hydro. $A^3$-$A^{33}$, dea. |
| ZP1857 (SEQ ID NO:45) | 3544.50 | 3544.86 | −0.36 | Major product $A^1$-$A^{33}$ |
|  | 3430.63 | 3430.81 | −0.18 | Minor, hydrolysis $A^1$-$A^{32}$ |
|  | 3351.38 | 3350.78 | +0.60 | Minor, hydrolysis $A^3$-$A^{33}$ |
|  | 3165.50 | 3164.71 | +0.79 | Minor, hydrolysis $A^5$-$A^{33}$ |
|  | 3222.50 | 3221.73 | +0.77 | Minor, hydrolysis $A^4$-$A^{33}$ |
|  | 2830.25 | 2829.56 | +0.69 | Minor, hydrolysis $A^8$-$A^{33}$ |
|  | 3545.13 | Na | +0.63 | Minor, recemization |
| ZP1849 (SEQ ID NO:37) | 4299.63 | 4299.41 | +0.22 | Major product, $A^1$-$A^{39}$ |
|  | 2755.88 | 2755.70 | +0.18 | Minor, hydrolysis, $A^{16}$-$A^{38}$ |
|  | 3532.00 | 3531.82 | +0.18 | Minor, hydrolysis, $A^1$-$A^{33}$ |
|  | 2158.38 | 2159.05 | −0.67 | Minor, hydrolysis, |
|  |  | 2158.37 | +0.01 | $A^1$-$A^{21}$ or $A^{22}$-$A^{39}$ |
|  | 3976.88 | 3976.29 | +0.59 | Minor, hydrolysis, $A^4$-$A^{39}$ |
|  | 4105.13 | 4105.33 | −0.20 | Minor, hydrolysis, $A^3$-$A^{39}$ |
|  | 3920.50 | 3919.27 | +1.23 | Minor, hydro., $A^5$-$A^{39}$, dea. |
|  | 1561.84 | 1561.73 | +0.11 | Minor, hydrolysis, $A^1$-$A^{15}$ |
| ZP1858 (SEQ ID NO:46) | 3532.13 | 3530.84 | +1.29 | Major product/deamida. |

Na = not available, no theoretical MW was calculated or suggested.

TABLE 11-continued

GLP-2 analogues incubated 12 days at 40° C. in 0.1 M HCl.

| GLP-2 analogues | Measured MW (Da) | Theoretical MW (Da) | Difference Mass (Da) | Major/minor abundance Possible ID suggestion |
|---|---|---|---|---|

*Mass difference is the measured MW from the theoretical MW for the main peak or for the suggested compound.

The results in Table 12 show that the measured molecular weight for the GLP-2 analogues tested and the Gly$^2$-GLP-2 reference, ZP1559 (SEQ ID NO:54), correspond to the theoretical molecular weight.

The most abundant degradation products are the cleavage between amino acids 3 and 4; Asp and Gly in ZP1559 (SEQ ID NO:54), ZP1820 (SEQ ID NO:10), and ZP1834 (SEQ ID NO:24). For the compounds ZP1846 (SEQ ID NO:34), ZP1848 (SEQ ID NO:36), and ZP1849 (SEQ ID NO:37), which are with C-terminal -K$_6$, degradation products corresponding to a loss of C-terminal -K$_6$ (Lys$_6$) in position 33-39 were detected. For the compounds ZP1855 (SEQ ID NO:43) and ZP1857 (SEQ ID NO:45), which are without C-terminal -K$_6$, degradation products corresponding to a loss of C-terminal Asp in position 33 were detected.

Minor degradation products detected were cleavage between amino acids 15 and 16 (Asp and Asn or Asp and Ala), amino acids 4 and 5 (Gly and Ser), amino acids 21 and 22 (Asp and Phe).

Solutions Stressed by $H_2O_2$

TABLE 12

GLP-2 analogues incubated 3 days at 40° C. in 0.5 % $H_2O_2$.

| GLP-2 analogues | Measured MW (Da) | Theoretical MW (Da) | Difference* Mass (Da) | Major/minor abundance Possible ID suggestion |
|---|---|---|---|---|
| ZP1559 (SEQ ID NO:54) | n.d. 3766.00 | 3749.80 Na | — +16.2 | No product intact Major, oxidation of M |
| ZP1820 (SEQ ID NO:10) | 4070.63 4052.38 4086.50 4068.75 | 4070.28 Na Na Na | -0.35 -18.25 +15.87 -1.88 | Major product Major, deamidation precursor Minor, oxidation of W Minor, 2 × deamidation |
| ZP1834 (SEQ ID NO:24) | 3301.75 3283.75 3317.88 3299.75 | 3301.71 Na Na Na | +0.04 -18.00 +16.13 -2.00 | Major product Major, deamidation precursor Minor, oxidation of W Minor, 2 × deamidation |
| ZP1846 (SEQ ID NO:34) | 4315.50 4331.88 | 4315.41 Na | +0.09 +16.38 | Major product Minor, oxidation of W |
| ZP1855 (SEQ ID NO:43) | 3547.00 3481.88 3410.00 3563.00 | 3546.84 Na Na Na | +0.16 -65.12 -137.00 +16.00 | Major product Minor, no suggest Minor, A$^2$-A$^{33}$ Minor, oxidation of W |
| ZP1848 (SEQ ID NO:36) | 4313.50 4329.63 | 4313.43 Na | +0.07 +16.13 | Major product Minor, oxidation of W |
| ZP1857 (SEQ ID NO:45) | 3545.00 3408.00 3561.00 3479.88 | 3544.86 Na Na Na | +0.14 -137.00 +16.00 -65.12 | Major product Minor, A$^2$-A$^{33}$ Minor, oxidation of W Minor, no suggest |
| ZP1849 (SEQ ID NO:37) | 4299.50 4315.75 | 4299.41 Na | +0.09 +16.25 | Major product Minor, oxidation of W |
| ZP1858 (SEQ ID NO:46) | 3531.00 3394.13 3547.00 3466.00 | 3530.84 Na Na Na | +0.16 -136.87 +16.00 -65.00 | Major product Minor, A$^2$-A$^{33}$ Minor, oxidation of W Minor, no suggest |

Na = not available, no theoretical MW was calculated or suggested.
*Mass difference is the measured MW from the theoretical MW for the main peak.

The results in Table 13 show that the measured molecular weight for the GLP-2 analogues tested and the Gly$^2$-GLP-2 reference, ZP1559 (SEQ ID NO:54), correspond to the theoretical molecular weight. For ZP1559 (SEQ ID NO:54), a major degradation product with a MW of +16 Da is observed, which could probably be the oxidized products of Met in position 10. For ZP1820 (SEQ ID NO:10) and ZP1834 (SEQ ID NO:24), a major degradation product with a MW of +18

Da is observed. They could probably be loss of water in the precursor to a deamidation. In addition, minor products with MW of −2 Da is observed and could be deamidation in two sites. Minor products with MW of +16 Da is observed in all compounds and could probably be oxidation of Trp. For the 5 compounds ZP1855 (SEQ ID NO:43), ZP1857 (SEQ ID NO:45), and ZP1858 (SEQ ID NO:46), which all are without C-terminal -$K_6$, minor degradation products with MW of −137 Da and of −65 Da are detected, corresponding to a loss of His in position 1 and an unidentified degradation product, respectively.

Solutions Stressed by NaOH

TABLE 13

GLP-2 analogues incubated 3 days at 40° C. in 0.01 M NaOH.

| GLP-2 analogues | Measured MW (Da) | Theoretical MW (Da) | Difference* Mass (Da) | Comments |
|---|---|---|---|---|
| ZP1559 (SEQ ID NO:54) | 3750.35 | 3749.80 | +0.58 | No change in MW |
| ZP1820 (SEQ ID NO:10) | 4070.63 | 4070.28 | +0.35 | No change in MW |
| ZP1834 (SEQ ID NO:24) | 3302.00 | 3301.71 | +0.29 | No change in MW |
| ZP1846 (SEQ ID NO:34) | 4315.63 | 4315.41 | +0.22 | No change in MW |
| ZP1855 (SEQ ID NO:43) | 3547.25 | 3546.84 | +0.41 | No change in MW |
| ZP1848 (SEQ ID NO:36) | 4313.88 | 4313.43 | +0.45 | No change in MW |
| ZP1857 (SEQ ID NO:45) | 3545.13 | 3544.86 | +0.27 | No change in MW |
| ZP1849 (SEQ ID NO:37) | 4299.88 | 4299.41 | +0.47 | No change in MW |
| ZP1858 (SEQ ID NO:46) | 3531.13 | 3530.84 | +0.29 | No change in MW | na = not available, no theoretical MW was calculated or suggested.
*Mass difference is the measured MW from the theoretical MW for the main peak.

The LC-MS analyses show the same molecular weight in all peaks for each compound. This means that the most abundant degradation products are probably racemization from L- to D-form of one or more of the amino acids in the sequence. The main peak can then hide one or several racemized products, thus no residual purity of intact peptide could be determined. No major degradation products from cleavage have been detected.

Solutions Stressed by $NH_4HCO_3$

TABLE 14

GLP-2 analogues incubated 6 days at 40° C. in 0.1 M $NH_4HCO_3$, pH 8

| GLP-2 analogues | Measured MW (Da) | Theoretical MW (Da) | Difference* Mass (Da) | Major/minor abundance Possible ID suggestion |
|---|---|---|---|---|
| ZP1559 (SEQ ID NO:54) | 3750.00 | 3749.80 | +0.20 | Major product |
|  | 3751.13 | Na | +1.13 | Minor, possible deamidation |
|  | 3751.13 | Na | +1.13 | Minor, Possible deamidation |
| ZP1820 (SEQ ID NO:10) | 4070.13 | 4070.28 | −0.15 | Major product |
|  | 4070.13 | Na | −0.15 | Minor, possible racemization |
| ZP1834 (SEQ ID NO:24) | 3302.00 | 3301.71 | +0.29 | Major product |
|  | 3302.00 | Na | +0.29 | Minor, possible racemization |

TABLE 14-continued

GLP-2 analogues incubated 6 days at 40° C. in 0.1 M NH₄HCO₃, pH 8

| GLP-2 analogues | Measured MW (Da) | Theoretical MW (Da) | Difference* Mass (Da) | Major/minor abundance Possible ID suggestion |
|---|---|---|---|---|
| ZP1846 (SEQ ID NO:34) | 4315.25 4315.63 | 4315.41 Na | −0.16 +0.38 | Major product Minor, possible racemization |
| ZP1855 (SEQ ID NO:43) | 3547.13 | 3546.84 | +0.29 | Major product |
| ZP1848 (SEQ ID NO:36) | 4313.75 | 4313.43 | +0.32 | Major product |
| ZP1857 (SEQ ID NO:45) | 3544.75 | 3544.86 | −0.11 | Major product |
| ZP1849 (SEQ ID NO:37) | 4299.50 | 4299.41 | +0.09 | Major product |
| ZP1858 (SEQ ID NO:46) | 3531.00 | 3530.84 | +0.16 | Major product |

Na = not available, no theoretical MW was calculated or suggested.
*Mass difference is the measured MW from the theoretical MW for the main peak.

The results in Table 14 show that the measured molecular weight for the GLP-2 analogues tested and the Gly2-GLP-2 reference, ZP1559 (SEQ ID NO:54), correspond to the theoretical MW. For ZP1559, minor degradation products with a MW of +1 Da are observed, which could probably be deamidated products. For ZP1820 (SEQ ID NO:10), ZP1834 (SEQ ID NO:24), and ZP1846 (SEQ ID NO:34), minor degradation products with the same MW as for the main compound are observed. They could probably be racemized products or deamidation. However, the MS resolution of the present instrument was not adequate to confirm or reject this. In addition, these products could be present in the other compounds, but not detected as they could be hidden under the main peak.

All the present GLP-2 analogues tested have better chemical stability compared with the reference compound Gly2-GLP-2; 1559 (SEQ ID NO:54), under stress conditions for hydrolysis, oxidation and deamidation. The compounds 1820 (SEQ ID NO:10) and 1834 (SEQ ID NO:24) are less stable than the remaining six candidates due to acid hydrolysis. Highest chemical stability was seen when amino acid $A^3$ was Glu rather than Asp. No significant difference in the chemical stability of the remaining six candidates were observed, except a slightly better stability without -$K_6$, which were mainly due to a labile site after Asp and the loss of -$K_6$ in candidates having the C-terminal -$K_6$.

Example 8

Screening for Intestinal Growth Effects of Compounds in C57BL Mice

The ability of the present compounds to stimulate intestinal growth was determined in male C57BL mice. Individual groups (n=6) of mice were given 30 nmol/kg of each compound, s.c, twice daily for ten consecutive days. For comparison purposes other groups of animals were given either an equimolar dose of [Gly2]GLP-2 (SEQ ID NO:54) or vehicle (phosphate buffered saline, pH 7.4) in the same dosing regimen. Twenty-four hours after the last dose of compound had been given the mice were sacrificed and the small intestine (from the pylorus to the cecum) and the colon (intestine distal to cecum) was emptied and weighed. To correct for slight difference in body weight (BW), the organ mass of the small intestine (SI) and colon were expressed relative to BW. The non-selective reference compound [Gly2]GLP-2 (SEQ ID NO:54) has been reported to stimulate gastrointestinal growth in both esophagus, stomach, small intestine and colon and to evaluate differences in growth pattern induced by compounds, the small intestine-colon sensitivity index of compound X was calculated as:

$$(SI/Colon)_x/(SI/Colon)_{[Gly2]GLP-2}\%$$

Compounds with a small intestine-colon sensitivity greater than or equal to 1.05 were considered relatively selective for the small intestine (Table 15).

Compounds with a small intestine-colon sensitivity smaller than or equal to 0.95 were considered relatively selective for the colon (Table 15).

TABLE 15

List of selective GLP-2 analogue compounds.

Position: 1 2 3 4 5 6 7 8 9 10 11 12 13 14 15 16 17 18 19 20 21 22 23 24 25 26 27 28 29 30 31 32 33    % [Gly2]GLP-2

Non-selective reference compound = [Gly2]GLP-2 (SEQ ID NO:54)

| # | Sequence | C-term | % | % | % |
|---|---|---|---|---|---|
|  | H G D G S F S D E M N T I L D N L A A R D F I N W L I Q T K I T D | OH | 100 | 100 | 100 |

Small intestine selective compounds (SEQ ID NOS:32-34, 36-41, 43, 45-57)

| # | Sequence | C-term | % | % | % |
|---|---|---|---|---|---|
| 1844 | H G E G T F S S E L S T I L D A L A A R D F I A W L I A T K I T D K6 | NH2 | 106 | 89 | 119 |
| 1845 | H G E G T F S D E L S T I L D A L A A R D F I A W L I A T K I T D K6 | NH2 | 105 | 98 | 107 |
| 1846 | H G E G S F S S E L S T I L D A L A A R D F I A W L I A T K I T D K6 | NH2 | 120 | 102 | 118 |
| 1848 | H G E G T F S S E L A T I L D A L A A R D F I A W L I A T K I T D K6 | NH2 | 109 | 93 | 117 |
| 1849 | H G E G S F S S E L A T I L D A L A A R D F I A W L I A T K I T D K6 | NH2 | 109 | 95 | 115 |
| 1850 | H G E G S F S D E L K T I L D A L A A R D F I A W L I A T K I T D K6 | NH2 | 103 | 89 | 116 |
| 1851 | H G E G T F S D E L K T I L D A L A A R D F I A W L I A T K I T D K6 | NH2 | 109 | 96 | 114 |
| 1852 | H G E G T F S S E L K T I L D A L A A R D F I A W L I A T K I T D K6 | NH2 | 106 | 97 | 109 |
| 1853 | H G E G T F S S E L S T I L D A L A A R D F I A W L I A T K I T D | NH2 | 101 | 96 | 105 |
| 1855 | H G E G S F S S E L S T I L D A L A A R D F I A W L I A T K I T D | NH2 | 106 | 88 | 120 |
| 1857 | H G E G T F S S E L A T I L D A L A A R D F I A W L I A T K I T D | NH2 | 117 | 90 | 130 |
| 1858 | H G E G S F S S E L A T I L D A L A A R D F I A W L I A T K I T D | NH2 | 104 | 96 | 108 |
| 1859 | H G E G S F S D E L K T I L D A L A A R D F I A W L I A T K I T D | NH2 | 83 | 73 | 114 |

Colon selective compounds (SEQ ID NOS:20, 21, 25-29, 31)

| # | Sequence | C-term | % | % | % |
|---|---|---|---|---|---|
| 1830 | H G D G S F S D E L S T I L D N L A A R D F I A W L I Q T K | NH2 | 100 | 106 | 94 |
| 1831 | H G D G S F T D E L S T I L D N L A A R D F I A W L I Q T K | NH2 | 90 | 102 | 88 |
| 1835 | H G D G S F S D E L K T I L D N L A A R D F I A W L I Q T K | NH2 | 96 | 105 | 91 |
| 1836 | H G D G S F T D E L K T I L D N L A A R D F I A W L I Q T K | NH2 | 94 | 105 | 90 |
| 1839 | H G D G S F S D E L A T I L D N L A A R D F I A W L I Q T K I T D K6 | NH2 | 112 | 133 | 84 |
| 1840 | H G D G S F S D E L A T I L D N L A A R D F I A W L I Q T K I T D | NH2 | 113 | 131 | 86 |
| 1841 | H G D G S F S D E L A T I L D N L A A R D F I A W L I Q T K | NH2 | 113 | 126 | 90 |
| 1843 | H G D G S F T D E L A T I L D N L A A R D F I A W L I Q T K | NH2 | 111 | 130 | 85 |

Results

The intestinal growth effects of the present compounds according to the invention were determined based on the ability of the peptides to dose-dependently increase SI mass relative to the effect of equimolar doses of the non-selective reference compound [Gly$_2$]GLP-2 (SEQ ID NO:54).

The findings from this study demonstrate that GLP-2 variants having amino acid substitutions at positions 8, 16, 24 and/or 28 of the wild-type GLP-2 sequence have increased biological activity compared to [Gly2]GLP-2 (SEQ ID NO:54) in C57BL mice.

Example 9

Dose-Response Effect of Selected Compounds on Intestinal Growth in C57BL Mice 1820 (SEQ ID NO:10), 1855 (SEQ ID NO:43), 1846 (SEQ ID NO:34), 1858 (SEQ ID NO:46), 1849 (SEQ ID NO:37), 1848 (SEQ ID NO:36), and 1857 (SEQ ID NO:45) were selected as lead compounds since these compounds both increased small intestine mass relative to [Gly2]GLP-2 (SEQ ID NO:54) (Example 8) and had increased chemical stability relative to [Gly2]GLP-2 (SEQ ID NO:54) under stressful conditions (Example 7). The dose-response effect of 1820 (SEQ ID NO:10), 1855 (SEQ ID NO:43), ZP1846 (SEQ ID NO:34), 1858 (SEQ ID NO:46), 1849 (SEQ ID NO:37), 1848 (SEQ ID NO:36), and 1857 (SEQ ID NO:45) on small intestinal mass was determined in male C57BL mice. Individual groups (n=6) of mice were given 5, 15, 45, 135 or 405 nmol/kg of each compound, s.c, twice daily for three consecutive days. For comparison purposes other groups of animals were given either equimolar doses of [Gly2]GLP-2 (SEQ ID NO:54) or vehicle (phosphate buffered saline, pH 7.4) in the same dosing regimen. Twenty-four hours after the last-dose of compound had been given the mice were sacrificed and the small intestine (from the pylorus to the cecum emptied and weighed to determine the effect on small intestinal mass.

Results

The effect of 1820 (SEQ ID NO:10), 1855 (SEQ ID NO:43), 1846 (SEQ ID NO:34), 1858 (SEQ ID NO:46), 1849 (SEQ ID NO:37), 1848 (SEQ ID NO:36), and 1857 (SEQ ID NO:45) on small intestine mass, relative to the effect of the reference compound, [Gly2]GLP-2 (SEQ ID NO:54) is shown in FIGS. 1 to 5. At each of the doses tested the effect of [Gly$_2$]GLP-2 (SEQ ID NO:54) on small intestine mass is standardised at 100%. The intestinal growth effects of the compounds 1820 (SEQ ID NO:10), 1855 (SEQ ID NO:43), 1846 (SEQ ID NO:34), 1858 (SEQ ID NO:46), 1849 (SEQ ID NO:37), 1848 (SEQ ID NO:36), and 1857 (SEQ ID NO:45) according to the invention were determined based on the ability of the peptides to dose-dependently increase SI mass relative to the effect of equimolar doses of [Gly$_2$]GLP-2 (SEQ ID NO:54). Based on these findings we can conclude that GLP-2 analogues containing 8 substitutions (G2, E3, T5, L10, A11, A16, A24, A28 with regard to GLP-2 1809 (SEQ ID NO:1)) give rise to a significant increase in the weight of the small intestine compared to mice treated with [Gly2]GLP-2 (SEQ ID NO:54).

In particular, substitution of Asp3 for Glu and Asn16 for Ala and Gln28 for Ala effect the increase in the weight of the small intestine in a selective manner compared to the colon (1839 (SEQ ID NO:27) or 1840 (SEQ ID NO:28) in comparison with 1809 (SEQ ID NO:1)). Thus, substitution of the three amino acids Asp3, Asn16 and Gln28 results in a selective increase of the small intestine weight relative to the colon mass.

Furthermore, substitution of the Asp8 for Serine results in an additional increase in the selectivity, thus resulting in a supplementary increase in the weight of the small intestine without significant effecting the weight of the colon (1818 (SEQ ID NO:8), 1820 (SEQ ID NO:10), 1844 (SEQ ID NO:32), 1846 (SEQ ID NO:34), 1848 (SEQ ID NO:36), 1849 (SEQ ID NO:37), 1852 (SEQ ID NO:40), 1853 (SEQ ID NO:41), 1855 (SEQ ID NO:43), 1858 (SEQ ID NO:46)).

FIGS. 1 to 4 show the results of experiments in which the dose response effect of exemplified compounds 1846 (SEQ ID NO:34), 1855 (SEQ ID NO:43), 1848 (SEQ ID NO:36), 1857 (SEQ ID NO:45), 1849 (SEQ ID NO:37) on the SI-BW to colon-BW ratio is shown relative to reference compound [Gly$_2$]GLP-2 (SEQ ID NO:54). At each of the doses tested the effect of [Gly$_2$]GLP-2 (SEQ ID NO:54) on small intestine mass is standardised at 100%. All of the exemplified compounds share modifications at positions 8, 16 and/or 28 and show increased selectivity for causing growth of the small intestine relative to the colon.

Example 10

Dose Response Effect of 1846 (SEQ ID NO:34), 1848 (SEQ ID NO:36), 1855 (SEQ ID NO:43), and 1857 (SEQ ID NO:45) on Small Intestinal Atrophy in Mice Administered 5-FU The rapid rate of proliferation of the small intestinal stem cells, makes them a susceptible target to the cytotoxic effects of the chemotherapeutic agents used in anti-cancer therapies. Consequently, clinical use of the chemotherapeutic agent 5-fluorouracil (5-FU) is frequently associated with small intestinal injury (atrophy and diarrhea in cancer patients. We have previously shown that i.p. administration of 50 mg/kg 5-FU once daily for four days induces significant small intestinal atrophy in C57BL mice. The effect of the lead compounds, 1846 (SEQ ID NO:34), 1848 (SEQ ID NO:36), 1855 (SEQ ID NO:43), and 1857 (SEQ ID NO:45) on 5-FU-induced small intestinal atrophy was investigated in mice. We have previously shown that i.p. administration of 50 mg/kg 5-FU once daily for four days induces significant small intestinal atrophy in C57BL mice. 1846 (SEQ ID NO:34), 1848 (SEQ ID NO:36), 1855 (SEQ ID NO:43), or 1857 (SEQ ID NO:45) were administered twice daily for three days prior to 5-FU and for four days together with 5-FU administration. The lead compounds were each administered at five different doses (5, 15, 45, 135 and 405 nmol/kg) that have been previously shown to effectively stimulate small intestine growth in healthy mice (Example 9). For comparison purposes a group of animals were treated with 405 nmol/kg [Gly2]GLP-2 (SEQ ID NO:54). To determine the effect of 5-FU on the small intestine a group of animals were given 5-FU I alone and left untreated (5-FU controls) and another group of animals were only given vehicle (PBS controls).

Results

5-FU induced a significant decrease in SI-BW and SI length in C57BL mice, relative to PBS controls. The dose-response effect of 1846 (SEQ ID NO:34), 1848 (SEQ ID NO:36), 1855 (SEQ ID NO:43), or 1857 (SEQ ID NO:45) on SI-BW and SI length in mice administered 5-FU is shown in FIGS. 6 to 9. The effect of 405 nmol/kg [Gly2]GLP-2 (SEQ ID NO:54) is also shown. 1846 (SEQ ID NO:34), 1848 (SEQ ID NO:36), 1855 (SEQ ID NO:43), or 1857 (SEQ ID NO:45) dose-dependently prevented 5-FU-induced SI atrophy and maintained SI-BW at levels similar to PBS controls. ZP1848 (SEQ ID NO:36), ZP1855 (SEQ ID NO:43), and ZP1857 (SEQ ID NO:45), given at an equimolar dose, were significantly more efficacious than 405 nmol/kg [Gly2]GLP-2 (SEQ ID NO:54) on SI-BW. 1848 (SEQ ID NO:36) and 1857 (SEQ ID NO:45), were significantly more efficacious than 405 nmol/kg [Gly2]GLP-2 (SEQ ID NO:54) on SI-length.

Example 11

Dose Response Effect of 1846 (SEQ ID NO:34) on Small Intestinal Atrophy and Diarrhea in SD Rats Administered 5-FU The effect of the clinical candidate, 1846 (SEQ ID NO:34), on 5-FU-induced small intestinal atrophy and diarrhea was investigated in SD rats. We have previously shown that i.p. administration of 75 mg/kg 5-FU once daily for four days induces significant small intestinal atrophy and diarrhea in SD rats. 1846 (SEQ ID NO:34) (16, 80 and 400 nmol/kg/d; n=20 rats/dose group) was administered twice daily for three days prior to 5-FU and for four days together with 5-FU administration. 5-FU controls and PBS controls were included in the study. Twenty-four hours after the last dose of 1846 (SEQ ID NO:34) was given a subset of animals were sacrificed to determine the effect of 1846 (SEQ ID NO:34) on small intestinal atrophy. To determine the effect of 1846 (SEQ ID NO:34) on diarrhea all the animals were observed twice daily (morning and evening), during the dosing period and for an additional six days. At each observation period each animal was given a score (0, no diarrhea, 1 (mild), fecal staining around the anus, 2 (moderate), fecal staining on the hind limbs and tail and 3 (severe) fecal staining on the front limbs and abdomen) that indicated whether or not the animal had diarrhea and the severity of the diarrhea Results 5-FU induced a significant decrease in SI-BW and SI length and induced diarrhea, in SD rats, relative to PBS controls. The dose-response effect of 1846 (SEQ ID NO:34) on 5-FU induced small intestinal atrophy and diarrhea is shown in FIGS. 10 and 11. 1846 (SEQ ID NO:34) dose-dependently prevented 5-FU induced small intestinal atrophy and maintained SI-BW and SI length at levels similar to the controls. At the highest dose (400 nmol/kg) administered, 1846 (SEQ ID NO:34), decreased the incidence and severity of diarrhea in rats administered 5-FU Example 12

Dose Response Effect of 1846 (SEQ ID NO:34) on Crypt-Villus Length and Muscularis Thickness in the Small Intestine of SD Rats The effect of the clinical candidate, 1846 (SEQ ID NO:34), on crypt-villus length and muscularis thickness in the small intestine of SD rats was investigated. 1846 (SEQ ID NO:34) (0.62, 3.41 or 6.2 mg/kg/day, n=6 rats/dose group) was administered as an i.v. bolus, once daily for five consecutive days. Twenty-four hours after the last dose had been administered the rats were sacrificed and a 1 cm biopsy was excised from the jejunum (30 cm distal from the gastric duodenal junction) and from the ileum (30 cm proximal from the ileocaecal junction) for histological processing.

Results

The dose-response effect of 1846 (SEQ ID NO:34) on crypt-villus length and muscularis thickness in the jejunum and ileum is shown in FIG. 12. 1846 (SEQ ID NO:34) dose-dependently increased mean crypt-villus length in the jejunum and ileum muscularis thickness in the ileum.

Example 13

Effect of 1848 (SEQ ID NO:36) on Markers of Small Intestinal Inflammation in an Indomethacin-Induced Model of Crohn's Disease Crohn's disease is a chronic disease that causes episodic inflammation of the small intestine. The effect of the GLP-2 analogue 1848 (SEQ ID NO:36) on small intestinal inflammation in an indomethacin-induced model of Crohn's disease was investigated. We have previously shown that administration of indomethacin (s.c, once daily for 2 days) induces small intestinal inflammation characterized by ulcerations and, increases in the pro-inflammatory cytokine, tumour necrosis factor alpha (TNF-$\alpha$).

To determine the effect of ZP1848 (SEQ ID NO:36) on ulceration 1848 (SEQ ID NO:36) (8, 40 and 200 nmol/kg, s.c, twice daily (9:00 and 16:00)) was given for 4 days prior to the first dose of indomethacin and for an additional two days together with indomethacin. The corticosteroid, prednisolone (10 mg/kg, p.o) was used as a positive control since corticosteroids are commonly used in the treatment of active inflammation in Crohn's disease. In addition a group of animals were given both 1848 (SEQ ID NO:36) (200 nmol/kg) and prednisolone to determine the effects of a combination treatment. Twenty four hours after the last dose of 1848 (SEQ ID NO:36) had been given the animals were sacrificed the small intestine was gently flushed clean and fixed. To determine the extent of ulceration the intestine was cut open along the antimesenteric margin, suspended on a polypropylene plate and surface-stained with Alcian Green 3BX. Starting at the pylorus, the small intestine was scanned and the shape (circular vs. linear) and size (circular ulcers: diameter, linear ulcers: length×width) of all ulcers was measured using a standard ruler (resolution: 0.5 mm). An ulcer was defined as an area, which lacked epithelial surface. Finally the total damaged area was calculated for each animal by summation of the areas of all individual ulcers.

To determine the effect of 1848 (SEQ ID NO:36) on the concentrations of TNF-$\alpha$ in the small intestine 1848 (SEQ ID NO:36) and Indomethacin were given as described above. At sacrifice, however the small intestine was separated into three segments of equal length (proximal, mid and distal). TNF-$\alpha$ concentrations were measured in each of the individual segments using a commercially available ELISA kit.

Results

Indomethacin caused a strong induction of small intestinal ulcers, compared to the control group ((estimated extent of ulceration 333±21 mm$^2$ vs. 10 mm$^2$. The effect of 1846 (SEQ ID NO:34) on the estimated extent of ulceration (mm$^2$) is shown in FIG. 13. Treatment with 1848 (SEQ ID NO:36) (8 nmol/kg, 40 nmol/kg and 200 nmol/kg, significantly decreased the extent of ulceration (230±12 mm$^2$, 216±17 mm$^2$, and 178±17 mm$^2$ respectively, p<0.001 vs. indomethacin). At the highest dose (200 nmol/kg) used ZP1848 (SEQ ID NO:36) was more effective than the positive control, prednisolone (p<0.05).

Indomethacin caused an approx. 2.9-fold increase in tissue levels of TNF-$\alpha$ in the proximal segment (97±14 pg/mg protein) compared to control animals (34±7 pg/mg protein, p<0.05 vs. indomethacin). The effect of 1846 (SEQ ID NO:34) on small intestinal TNF-$\alpha$ concentrations is shown in FIG. 14. Treatment with 1848 (SEQ ID NO:36) (8, 40 or 200 nmol/kg), significantly reduced tissue levels of TNF-$\alpha$ (45±14 pg/mg protein, 44±9 pg/mg protein and 45±7 pg/mg protein, respectively) with no significant difference between the 3 doses.

Indomethacin caused an approx. 3.2-fold increase in tissue levels of TNF-$\alpha$ in the mid segment (108±9 pg/mg protein) compared to control animals (34±6 pg/mg protein, p<0.05 vs. indomethacin). 1848 (SEQ ID NO:36) (40 or 200 nmol/kg) significantly reduced tissue levels of TNF-$\alpha$ respectively, p<0.05 vs. indomethacin)

Indomethacin caused an approx. 1.7-fold increase in tissue levels of TNF-$\alpha$ in the distal segment (75±5 pg/mg protein) compared to control animals (45±3 pg/mg protein, p<0.05 vs. indomethacin). 1848 (SEQ ID NO:36) had an inhibitory effect on TNF-$\alpha$ levels in the distal segment but the effect was less pronounced compared to the other segments. Prednisolone alone did not significantly affect tissue levels of TNF-$\alpha$ in all 3 segments but prednisolone administration improved the inhibitory effect of 1848 (SEQ ID NO:36) (200 nmol/kg) on TNF-$\alpha$ levels exclusively in the distal segment.

Example 14

Formulation of ZP1846 (SEQ ID NO: 34), 10 Mg/ml in Histidine, Mannitol and Acetate Formulation 1. Fill 800 mL (WFI) water in to a 1 L beaker
2. Weigh 13.964 g L-histidine in a beaker and add to the 1 L beaker
3. Weigh 32.200 g Mannitol in a beaker and add to the 1 L beaker
4. Add 629 µL 100% acetic acid directly in to the 1 L beaker or weigh 12.58 g of a 5% (w/v) acetic acid solution and add to the beaker.
6. Fill to approximately 950 mL
7. Measure pH and adjust to pH 6.9-7.0 with 10% Acetic acid or 0.25 M Histidine if necessary 8. Weigh 11.312 g Drug Substance (peptide content 88.4%) and add to the beaker
9. Fill to 1.015 kg (=approximately 1000 mL) and measure pH, osmolarity and density.
10. Sterile filter the formulation through two sterile filters connected in series.
11. Dispense the formulation in 0.5 mL aliquots in a LAF bench into 2 mL pharmaceutically approved vials.
12. Partially place freeze-drying stoppers before loading into a lyophilizer that has been sterilized and pre-cooled to 4° C.
13. A lyophilization cycle is run over 40.5 hours consisting of freezing, annealing, primary drying and secondary drying phases. The vials are stoppered under nitrogen while in the lyophilizer chamber.
14. The vials are sorted and overseals and crimps are applied.

Example 15

Formulation of ZP1846 (SEQ ID NO:34), 10 Mg/ml in Histidine, Arginine, Mannitol and Trehalose
1. Fill 800 mL (WFI) water in to a 1 L beaker
2. Weigh 6.206 g L-Histidine in a beaker and add to the 1 L beaker
3. Weigh 3.484 g L-Arginine in a beaker and add to the 1 L beaker
4. Weigh 33.46 g Mannitol in a beaker and add to the 1 L beaker
5. Weigh 11.16 g Trehalose in a beaker and add to the 1 L beaker
6. Fill to approximately 950 mL
7. Measure pH and adjust to pH 6.9-7.0 with 10% Acetic acid or 0.25 M Histidine if necessary
8. Weigh 11.312 g Drug Substance (peptide content 88.4%) and add to the beaker
9. Fill to 1.015 kg (=approximately 1000 mL) and measure pH, osmolarity and density.
10. Sterile filter the formulation through two sterile filters connected in series.
11. Dispense the formulation in 0.5 mL aliquots in a LAF bench into 2 mL pharmaceutically approved vials.
12. Partially place freeze-drying stoppers before loading into a lyophilizer that has been sterilized and pre-cooled to 40° C.
13. A lyophilization cycle is run over 40.5 hours consisting of freezing, annealing, primary drying and secondary drying phases. The vials are stoppered under nitrogen while in the lyophilizer chamber.
14. The vials are sorted and overseals and crimps are applied While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents including patents, patent applications, and publications cited herein are expressly incorporated by reference.

The invention claimed is:

1. A glucagon-like peptide-2 (GLP-2) analog wherein said analog has the amino acid sequence:

H-HGEGSFSSELSTILDALAARDFIAWLIATKITDK$_6$-NH$_2$ (SEQ ID NO:34), or a pharmaceutically acceptable salt thereof.

2. A pharmaceutical composition comprising:
(a) the GLP-2 analog of claim 1, or a pharmaceutically acceptable salt thereof; and
(b) a pharmaceutically acceptable carrier.

* * * * *

UNITED STATES PATENT AND TRADEMARK OFFICE
CERTIFICATE OF CORRECTION

PATENT NO. : 7,563,770 B2
APPLICATION NO. : 11/429168
DATED : July 21, 2009
INVENTOR(S) : Bjarne D. Larsen et al.

Page 1 of 1

It is certified that error appears in the above-identified patent and that said Letters Patent is hereby corrected as shown below:

In the Specifications:

Column 34, Line 2, replace "residue washed" with --residue was washed--;

Line 22, replace "peptide-resin washed" with --peptide-resin was washed--.

Column 44, Line 51, replace "Gly2-GLP-2" with --$Gly^2$-GLP-2--.

Column 60, Line 13-14, replace "to 40°C" with --4°C--.

Signed and Sealed this
Twenty-third Day of April, 2013

Teresa Stanek Rea
*Acting Director of the United States Patent and Trademark Office*

SEQUENCE LISTING

```
<160> NUMBER OF SEQ ID NOS: 54

<210> SEQ ID NO 1
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 1

His Gly Glu Gly Thr Phe Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 2
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 2

His Gly Glu Gly Thr Phe Ser Asp Glu Leu Ala Thr Ile Leu Asp Ala
1               5                   10                  15

Leu Ala Ala Arg Ile Phe Ile Ala Trp Leu Ile Ala Thr Lys Lys Lys
            20                  25                  30

Lys Lys Lys
        35
```

```
<210> SEQ ID NO 3
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 3

His Gly Asp Gly Ser Pro Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 4
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 4

His Gly Glu Gly Ser Phe Ser Asp Glu Leu Ala Thr Ile Leu Asp Asn
1               5                   10                  15

Leu Ala Ala Arg Asp Phe Ile Ala Trp Leu Ile Gln Thr Lys Ile Thr
            20                  25                  30

Asp

<210> SEQ ID NO 5
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 5

His Gly Asp Gly Ser Phe Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 6
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 6

His Gly Asp Gly Ser Phe Ser Asp Glu Leu Ala Thr Ile Leu Asp Asn
1               5                   10                  15

Leu Ala Ala Arg Asp Phe Ile Ala Trp Leu Ile Ala Thr Lys Ile Thr
            20                  25                  30

Asp

<210> SEQ ID NO 7
<211> LENGTH: 33
<212> TYPE: PRT
<213> ORGANISM: Artificial Sequence
<220> FEATURE:
```

<223> OTHER INFORMATION: GLP-2 analogue

<400> SEQUENCE: 7

His Gly Glu Gly Ser Phe Ser Asp Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 8
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 8

His Gly Asp Gly Ser Phe Ser Ser Glu Leu Ala Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 9
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 9

His Gly Asp Gly Ser Phe Ser Asp Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 10
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 10

His Gly Asp Gly Ser Phe Thr Ser Glu Leu Ala Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 11
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 11

-continued

His Gly Asp Gly Ser Phe Ser Asp Glu Leu Lys Thr Ile Leu Asp Asn
1               5                   10                  15

Leu Ala Ala Arg Asp Phe Ile Ala Trp Leu Ile Gln Thr Lys Lys
            20                  25                  30

Lys Lys Lys
        35

<210> SEQ ID NO 12
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 12

His Gly Asp Gly Ser Phe Thr Asp Glu Leu Lys Thr Ile Leu Asp Asn
1               5                   10                  15

Leu Ala Ala Arg Asp Phe Ile Ala Trp Leu Ile Gln Thr Lys Lys
            20                  25                  30

Lys Lys Lys
        35

<210> SEQ ID NO 13
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 13

His Gly Asp Gly Ser Phe Thr Ser Glu Leu Lys Thr Ile Leu Asp Asn
1               5                   10                  15

Leu Ala Ala Arg Asp Phe Ile Ala Trp Leu Ile Gln Thr Lys Lys
            20                  25                  30

Lys Lys Lys
        35

<210> SEQ ID NO 14
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 14

His Gly Asp Gly Ser Phe Thr Asp Glu Leu Ala Thr Ile Leu Asp Asn
1               5                   10                  15

Leu Ala Ala Arg Asp Phe Ile Ala Trp Leu Ile Gln Thr Lys Lys
            20                  25                  30

Lys Lys Lys
        35

<210> SEQ ID NO 15
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 15

His Gly Asp Gly Ser Phe Ser Ser Glu Leu Ala Thr Ile Leu Asp Asn
1               5                   10                  15

-continued

Leu Ala Ala Arg Asp Phe Ile Ala Trp Leu Ile Gln Thr Lys
            20                  25                  30

<210> SEQ ID NO 16
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 16

His Gly Asp Gly Ser Phe Ser Asp Glu Leu Asn Thr Ile Leu Asp Asn
1               5                   10                  15

Leu Ala Ala Arg Asp Phe Ile Ala Trp Leu Ile Gln Thr Lys Ile Thr
            20                  25                  30

Asp Lys Lys Lys Lys Lys Lys
        35

<210> SEQ ID NO 17
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 17

His Gly Asp Gly Ser Phe Thr Asp Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 18
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 18

His Gly Asp Gly Ser Phe Thr Ser Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

<210> SEQ ID NO 19
<211> LENGTH: 35
<212> TYPE: PRT
<213> ORGANISM: Artificial Sequence
<220> FEATURE:
<223> OTHER INFORMATION: GLP-2 analogue

<400> SEQUENCE: 19

His Gly Asp Gly Ser Phe Ser Ser Glu Leu Ser Thr Ile Leu Asp Asn
1               5                   10                  15

Leu Ala Ala Arg Asp Phe Ile Ala Trp Leu Ile Gln Thr Lys Lys Lys
            20                  25                  30

Lys Lys Lys
        35

```
<210> SEQ ID NO 20
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 20

His Gly Asp Gly Ser Phe Ser Asp Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 21

His Gly Asp Gly Ser Phe Thr Asp Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 22

His Gly Asp Gly Ser Phe Thr Ser Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 23

His Gly Asp Gly Ser Phe Ser Ser Glu Leu Ser Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 24

His Gly Asp Gly Ser Phe Thr Ser Glu Leu Ala Thr Ile Leu Asp Asn
1               5                   10                  15

Leu Ala Ala Arg Asp Phe Ile Ala Trp Leu Ile Gln Thr Lys
            20                  25                  30
```

<210> SEQ ID NO 25
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 25

His Gly Asp Gly Ser Phe Ser Asp Glu Leu Lys Thr Ile Leu Asp Asn
1               5                   10                  15
Leu Ala Ala Arg Asp Phe Ile Ala Trp Leu Ile Gln Thr Lys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 26

His Gly Asp Gly Ser Phe Thr Asp Glu Leu Lys Thr Ile Leu Asp Asn
1               5                   10                  15
Leu Ala Ala Arg Asp Phe Ile Ala Trp Leu Ile Gln Thr Lys
            20                  25                  30

<210> SEQ ID NO 27
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 27

His Gly Asp Gly Ser Phe Ser Asp Glu Leu Ala Thr Ile Leu Asp Asn
1               5                   10                  15
Leu Ala Ala Arg Asp Phe Ile Ala Trp Leu Ile Gln Thr Lys Ile Thr
            20                  25                  30
Asp Lys Lys Lys Lys Lys Lys
        35

<210> SEQ ID NO 28
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 28

His Gly Asp Gly Ser Phe Ser Asp Glu Leu Ala Thr Ile Leu Asp Asn
1               5                   10                  15
Leu Ala Ala Arg Asp Phe Ile Ala Trp Leu Ile Gln Thr Lys Ile Thr
            20                  25                  30
Asp

<210> SEQ ID NO 29
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 29

```
His Gly Asp Gly Ser Phe Ser Asp Glu Leu Ala Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 30

His Gly Asp Gly Ser Phe Thr Ser Glu Leu Lys Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: GLP-2 analogue

<400> SEQUENCE: 31

His Gly Asp Gly Ser Phe Thr Asp Glu Leu Ala Thr Ile Leu Asp Asn
1               5                   10                  15

Leu Ala Ala Arg Asp Phe Ile Ala Trp Leu Ile Gln Thr Lys
            20                  25                  30

<210> SEQ ID NO 32
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 32

His Gly Glu Gly Thr Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 33
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 33

His Gly Glu Gly Thr Phe Ser Asp Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 34
```

```
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 34

His Gly Glu Gly Ser Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 35
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 35

His Gly Glu Gly Ser Phe Ser Asp Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 36
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 36

His Gly Glu Gly Thr Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 37
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 37

His Gly Glu Gly Ser Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 38
<211> LENGTH: 39
<212> TYPE: PRT
<213> ORGANISM: Artificial Sequence
```

```
<220> FEATURE:
<223> OTHER INFORMATION: GLP-2 analogue

<400> SEQUENCE: 38

His Gly Glu Gly Ser Phe Ser Asp Glu Leu Lys Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 39
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 39

His Gly Glu Gly Thr Phe Ser Asp Glu Leu Lys Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 40
<211> LENGTH: 39
<212> TYPE: PRT
<213> ORGANISM: Artificial Sequence
<220> FEATURE:
<223> OTHER INFORMATION: GLP-2 analogue

<400> SEQUENCE: 40

His Gly Glu Gly Thr Phe Ser Ser Glu Leu Lys Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 41
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 41

His Gly Glu Gly Thr Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 42
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 42
```

His Gly Glu Gly Thr Phe Ser Asp Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 43
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 43

His Gly Glu Gly Ser Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 44
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 44

His Gly Glu Gly Ser Phe Ser Asp Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 45
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 45

His Gly Glu Gly Thr Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 46
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 46

His Gly Glu Gly Ser Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp

<210> SEQ ID NO 47
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 47

His Gly Glu Gly Ser Phe Ser Asp Glu Leu Lys Thr Ile Leu Asp Ala
1               5                   10                  15
Leu Ala Ala Arg Asp Phe Ile Ala Trp Leu Ile Ala Thr Lys Ile Thr
            20                  25                  30
Asp

<210> SEQ ID NO 48
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 48

His Gly Glu Gly Thr Phe Ser Asp Glu Leu Lys Thr Ile Leu Asp Ala
1               5                   10                  15
Leu Ala Ala Arg Asp Phe Ile Ala Trp Leu Ile Ala Thr Lys Ile Thr
            20                  25                  30
Asp

<210> SEQ ID NO 49
<211> LENGTH: 33
<212> TYPE: PRT
<213> ORGANISM: Artificial Sequence
<220> FEATURE:
<223> OTHER INFORMATION: GLP-2 analogue

<400> SEQUENCE: 49

His Gly Glu Gly Thr Phe Ser Ser Glu Leu Lys Thr Ile Leu Asp Ala
1               5                   10                  15
Leu Ala Ala Arg Asp Phe Ile Ala Trp Leu Ile Ala Thr Lys Ile Thr
            20                  25                  30
Asp

<210> SEQ ID NO 50
<211> LENGTH: 33
<212> TYPE: PRT
<213> ORGANISM: Homo sapien

<400> SEQUENCE: 50

His Ala Asp Gly Ser Phe Ser Asp Glu Met Asn Thr Ile Leu Asp Asn
1               5                   10                  15
Leu Ala Ala Arg Asp Phe Ile Asn Trp Leu Ile Gln Thr Lys Ile Thr
            20                  25                  30
Asp

<210> SEQ ID NO 51
<211> LENGTH: 73
<212> TYPE: PRT
<213> ORGANISM: Artificial sequence
<220> FEATURE:
<223> OTHER INFORMATION: GLP-2 analogue -continued

```
<220> FEATURE:
<221> NAME/KEY: MISC_FEATURE
<222> LOCATION: (1)..(20)
<223> OTHER INFORMATION: Xaa = Ala, Leu, Ser, Thr, Tyr, Asn, Gln, Asp,
      Glu, Lys, Arg, His, Met, Orn or is absent
<220> FEATURE:
<221> NAME/KEY: MISC_FEATURE
<222> LOCATION: (22)..(22)
<223> OTHER INFORMATION: Xaa = Gly, Ala or Sar
<220> FEATURE:
<221> NAME/KEY: MISC_FEATURE
<222> LOCATION: (23)..(23)
<223> OTHER INFORMATION: Xaa = Glu or Asp
<220> FEATURE:
<221> NAME/KEY: MISC_FEATURE
<222> LOCATION: (25)..(25)
<223> OTHER INFORMATION: Xaa = Ser or Thr
<220> FEATURE:
<221> NAME/KEY: MISC_FEATURE
<222> LOCATION: (26)..(26)
<223> OTHER INFORMATION: Xaa = Phe or Pro
<220> FEATURE:
<221> NAME/KEY: MISC_FEATURE
<222> LOCATION: (27)..(27)
<223> OTHER INFORMATION: Xaa = Ser or Thr
<220> FEATURE:
<221> NAME/KEY: MISC_FEATURE
<222> LOCATION: (28)..(28)
<223> OTHER INFORMATION: Xaa = Asp or Ser
<220> FEATURE:
<221> NAME/KEY: MISC_FEATURE
<222> LOCATION: (29)..(29)
<223> OTHER INFORMATION: Xaa = Glu or Asp
<220> FEATURE:
<221> NAME/KEY: MISC_FEATURE
<222> LOCATION: (30)..(30)
<223> OTHER INFORMATION: Xaa = Met, Leu, Nle, or an oxidatively stable
      Met-replacement amino acid
<220> FEATURE:
<221> NAME/KEY: MISC_FEATURE
<222> LOCATION: (31)..(31)
<223> OTHER INFORMATION: Xaa = Asn, Ala, Lys, or Ser
<220> FEATURE:
<221> NAME/KEY: MISC_FEATURE
<222> LOCATION: (32)..(32)
<223> OTHER INFORMATION: Xaa = Thr or Lys
<220> FEATURE:
<221> NAME/KEY: MISC_FEATURE
<222> LOCATION: (33)..(33)
<223> OTHER INFORMATION: Xaa = Ile, Glu or Gln
<220> FEATURE:
<221> NAME/KEY: MISC_FEATURE
<222> LOCATION: (34)..(34)
<223> OTHER INFORMATION: Xaa = Leu, Met, or Nle
<220> FEATURE:
<221> NAME/KEY: MISC_FEATURE
<222> LOCATION: (35)..(35)
<223> OTHER INFORMATION: Xaa = Asp or Glu
<220> FEATURE:
<221> NAME/KEY: MISC_FEATURE
<222> LOCATION: (36)..(36)
<223> OTHER INFORMATION: Xaa = Asn or Ala
<220> FEATURE:
<221> NAME/KEY: MISC_FEATURE
<222> LOCATION: (37)..(37)
<223> OTHER INFORMATION: Xaa = Leu or Glu
<220> FEATURE:
<221> NAME/KEY: MISC_FEATURE
<222> LOCATION: (38)..(38)
<223> OTHER INFORMATION: Xaa = Ala or Aib
<220> FEATURE:
<221> NAME/KEY: MISC_FEATURE
<222> LOCATION: (39)..(39)
<223> OTHER INFORMATION: Xaa = Ala or Thr
<220> FEATURE:
<221> NAME/KEY: MISC_FEATURE
<222> LOCATION: (40)..(40)
<223> OTHER INFORMATION: Xaa = Arg or Lys
<220> FEATURE:
```

```
<221> NAME/KEY: MISC_FEATURE
<222> LOCATION: (41)..(41)
<223> OTHER INFORMATION: Xaa = Asp or Ile
<220> FEATURE:
<221> NAME/KEY: MISC_FEATURE
<222> LOCATION: (44)..(44)
<223> OTHER INFORMATION: Xaa = Asn, Ala, or Glu
<220> FEATURE:
<221> NAME/KEY: MISC_FEATURE
<222> LOCATION: (48)..(48)
<223> OTHER INFORMATION: Xaa = Gln, Ala, or Asn
<220> FEATURE:
<221> NAME/KEY: MISC_FEATURE
<222> LOCATION: (51)..(51)
<223> OTHER INFORMATION: Xaa = Pro Ile, or is absent
<220> FEATURE:
<221> NAME/KEY: MISC_FEATURE
<222> LOCATION: (52)..(52)
<223> OTHER INFORMATION: Xaa = Thr or is absent
<220> FEATURE:
<221> NAME/KEY: MISC_FEATURE
<222> LOCATION: (53)..(53)
<223> OTHER INFORMATION: Xaa = Asp, Asn or is absent
<220> FEATURE:
<221> NAME/KEY: MISC_FEATURE
<222> LOCATION: (54)..(73)
<223> OTHER INFORMATION: Xaa = Ala, Leu, Ser, Thr, Tyr, Asn, Gln, Asp,
      Glu, Lys, Arg, His, Met, Orn or is absent

<400> SEQUENCE: 51

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa His Xaa Xaa Gly Xaa Xaa Xaa Xaa Xaa Xaa Xaa
            20                  25                  30

Xaa Xaa Xaa Xaa Xaa Xaa Xaa Xaa Xaa Phe Ile Xaa Trp Leu Ile Xaa
        35                  40                  45

Thr Lys Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa
65                  70

<210> SEQ ID NO 52
<211> LENGTH: 73
<212> TYPE: PRT
<213> ORGANISM: Artificial sequence
<220> FEATURE:
<223> OTHER INFORMATION: GLP-2 analogue
<220> FEATURE:
<221> NAME/KEY: MISC_FEATURE
<222> LOCATION: (1)..(20)
<223> OTHER INFORMATION: Xaa = Ala, Leu, Ser, Thr, Tyr, Asn, Gln, Asp,
      Glu, Lys, Arg, His, Met, Orn or is absent
<220> FEATURE:
<221> NAME/KEY: MISC_FEATURE
<222> LOCATION: (23)..(23)
<223> OTHER INFORMATION: Xaa = Glu or Asp
<220> FEATURE:
<221> NAME/KEY: MISC_FEATURE
<222> LOCATION: (25)..(25)
<223> OTHER INFORMATION: Xaa = Ser or Thr
<220> FEATURE:
<221> NAME/KEY: MISC_FEATURE
<222> LOCATION: (27)..(27)
<223> OTHER INFORMATION: Xaa = Ser or Thr
<220> FEATURE:
<221> NAME/KEY: MISC_FEATURE
<222> LOCATION: (28)..(28)
<223> OTHER INFORMATION: Xaa = Asp or Ser
<220> FEATURE:
<221> NAME/KEY: MISC_FEATURE
<222> LOCATION: (29)..(29)
<223> OTHER INFORMATION: Xaa = Glu or Asp
<220> FEATURE:
```

```
<221> NAME/KEY: MISC_FEATURE
<222> LOCATION: (30)..(30)
<223> OTHER INFORMATION: Xaa = Met, Leu, Nle, or an oxidatively stable
      Met-replacement amino acid
<220> FEATURE:
<221> NAME/KEY: MISC_FEATURE
<222> LOCATION: (31)..(31)
<223> OTHER INFORMATION: Xaa = Asn, Ala, Lys or Ser
<220> FEATURE:
<221> NAME/KEY: MISC_FEATURE
<222> LOCATION: (32)..(32)
<223> OTHER INFORMATION: Xaa = Thr or Lys
<220> FEATURE:
<221> NAME/KEY: MISC_FEATURE
<222> LOCATION: (33)..(33)
<223> OTHER INFORMATION: Xaa = Ile, Glu, or Gln
<220> FEATURE:
<221> NAME/KEY: MISC_FEATURE
<222> LOCATION: (34)..(34)
<223> OTHER INFORMATION: Xaa = Leu, Met or Nle
<220> FEATURE:
<221> NAME/KEY: MISC_FEATURE
<222> LOCATION: (35)..(35)
<223> OTHER INFORMATION: Xaa = Asp or Glu
<220> FEATURE:
<221> NAME/KEY: MISC_FEATURE
<222> LOCATION: (36)..(36)
<223> OTHER INFORMATION: Xaa = Asn or Ala
<220> FEATURE:
<221> NAME/KEY: MISC_FEATURE
<222> LOCATION: (37)..(37)
<223> OTHER INFORMATION: Xaa = Leu or Glu
<220> FEATURE:
<221> NAME/KEY: MISC_FEATURE
<222> LOCATION: (39)..(39)
<223> OTHER INFORMATION: Xaa = Ala or Thr
<220> FEATURE:
<221> NAME/KEY: MISC_FEATURE
<222> LOCATION: (44)..(44)
<223> OTHER INFORMATION: Xaa = Asn or Ala
<220> FEATURE:
<221> NAME/KEY: MISC_FEATURE
<222> LOCATION: (48)..(48)
<223> OTHER INFORMATION: Xaa = Gln, Ala, or Asn
<220> FEATURE:
<221> NAME/KEY: MISC_FEATURE
<222> LOCATION: (51)..(51)
<223> OTHER INFORMATION: Xaa = Pro, Ile or is absent
<220> FEATURE:
<221> NAME/KEY: MISC_FEATURE
<222> LOCATION: (52)..(52)
<223> OTHER INFORMATION: Xaa = Thr or is absent
<220> FEATURE:
<221> NAME/KEY: MISC_FEATURE
<222> LOCATION: (53)..(53)
<223> OTHER INFORMATION: Xaa = Asp or is absent
<220> FEATURE:
<221> NAME/KEY: MISC_FEATURE
<222> LOCATION: (54)..(73)
<223> OTHER INFORMATION: Xaa = Ala, Leu, Ser, Thr, Tyr, Asn, Gln, Asp,
      Glu, Lys, Arg, His, Met, Orn or is absent

<400> SEQUENCE: 52

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa His Gly Xaa Gly Xaa Phe Xaa Xaa Xaa Xaa Xaa Xaa
            20                  25                  30

Xaa Xaa Xaa Xaa Xaa Ala Xaa Arg Asp Phe Ile Xaa Trp Leu Ile Xaa
        35                  40                  45

Thr Lys Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa
65                  70
```

```
<210> SEQ ID NO 53
<211> LENGTH: 73
<212> TYPE: PRT
<213> ORGANISM: Artificial sequence
<220> FEATURE:
<223> OTHER INFORMATION: GLP-2 analogue
<220> FEATURE:
<221> NAME/KEY: MISC_FEATURE
<222> LOCATION: (1)..(20)
<223> OTHER INFORMATION: Xaa = Ala, Leu, Ser, Thr, Tyr, Asn, Gln, Asp,
      Glu, Lys, Arg, His, Met, Orn or is absent
<220> FEATURE:
<221> NAME/KEY: MISC_FEATURE
<222> LOCATION: (23)..(23)
<223> OTHER INFORMATION: Xaa = Glu or Asp
<220> FEATURE:
<221> NAME/KEY: MISC_FEATURE
<222> LOCATION: (25)..(25)
<223> OTHER INFORMATION: Xaa = Ser or Thr
<220> FEATURE:
<221> NAME/KEY: MISC_FEATURE
<222> LOCATION: (27)..(27)
<223> OTHER INFORMATION: Xaa = Ser or Thr
<220> FEATURE:
<221> NAME/KEY: MISC_FEATURE
<222> LOCATION: (28)..(28)
<223> OTHER INFORMATION: Xaa = Asp or Ser
<220> FEATURE:
<221> NAME/KEY: MISC_FEATURE
<222> LOCATION: (30)..(30)
<223> OTHER INFORMATION: Xaa = Met, Leu, Nle, or an oxidatively stable
      Met-replacement amino acid
<220> FEATURE:
<221> NAME/KEY: MISC_FEATURE
<222> LOCATION: (31)..(31)
<223> OTHER INFORMATION: Xaa = Asn, Ala, Lys, or Ser
<220> FEATURE:
<221> NAME/KEY: MISC_FEATURE
<222> LOCATION: (36)..(36)
<223> OTHER INFORMATION: Xaa = Asn or Ala
<220> FEATURE:
<221> NAME/KEY: MISC_FEATURE
<222> LOCATION: (44)..(44)
<223> OTHER INFORMATION: Xaa = Asn or Ala
<220> FEATURE:
<221> NAME/KEY: MISC_FEATURE
<222> LOCATION: (48)..(48)
<223> OTHER INFORMATION: Xaa = Gln or Ala
<220> FEATURE:
<221> NAME/KEY: MISC_FEATURE
<222> LOCATION: (51)..(51)
<223> OTHER INFORMATION: Xaa = Pro or is absent
<220> FEATURE:
<221> NAME/KEY: MISC_FEATURE
<222> LOCATION: (52)..(52)
<223> OTHER INFORMATION: Xaa = Thr or is absent
<220> FEATURE:
<221> NAME/KEY: MISC_FEATURE
<222> LOCATION: (53)..(53)
<223> OTHER INFORMATION: Xaa = Asp or is absent
<220> FEATURE:
<221> NAME/KEY: MISC_FEATURE
<222> LOCATION: (54)..(73)
<223> OTHER INFORMATION: Xaa = Ala, Leu, Ser, Thr, Tyr, Asn, Gln, Asp,
      Glu, Lys, Arg, His, Met, Orn or is absent

<400> SEQUENCE: 53

Xaa Xaa Xaa Xaa Xaa Xaa Xaa Xaa Xaa Xaa Xaa Xaa Xaa Xaa Xaa
 1               5                  10                  15

Xaa Xaa Xaa Xaa His Gly Xaa Gly Xaa Phe Xaa Xaa Glu Xaa Xaa Thr
             20                  25                  30

Ile Leu Asp Xaa Leu Ala Ala Arg Asp Phe Ile Xaa Trp Leu Ile Xaa
             35                  40                  45

Thr Lys Xaa Xaa Xaa Xaa Xaa Xaa Xaa Xaa Xaa Xaa Xaa Xaa Xaa Xaa
```

```
                50                  55                  60
Xaa Xaa Xaa Xaa Xaa Xaa Xaa Xaa Xaa
 65                  70

<210> SEQ ID NO 54
<211> LENGTH: 33
<212> TYPE: PRT
<213> ORGANISM: Artificial sequence
<220> FEATURE:
<223> OTHER INFORMATION: GLP-2 analogue

<400> SEQUENCE: 54

His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
                20                  25                  30

Asp
```